(12) United States Patent
Côté et al.

(10) Patent No.: US 11,274,095 B2
(45) Date of Patent: Mar. 15, 2022

(54) MODULATORS OF METHYL MODIFYING ENZYMES, COMPOSITIONS AND USES THEREOF

(71) Applicant: Constellation Pharmaceuticals, Inc., Cambridge, MA (US)

(72) Inventors: Alexandre Côté, Cambridge, MA (US); Victor S. Gehling, Somerville, MA (US); Avinash Khanna, Cambridge, MA (US); Ludivine Moine, Cambridge, MA (US); Jacob I. Stuckey, Framingham, MA (US)

(73) Assignee: Constellation Pharmaceuticals, Inc., Cambridge, MA (US)

( * ) Notice: Subject to any disclaimer, the term of this patent is extended or adjusted under 35 U.S.C. 154(b) by 158 days.

(21) Appl. No.: 16/856,454

(22) Filed: Apr. 23, 2020

(65) Prior Publication Data
US 2020/0317651 A1    Oct. 8, 2020

Related U.S. Application Data

(63) Continuation of application No. 16/387,851, filed on Apr. 18, 2019, now Pat. No. 10,689,371.

(60) Provisional application No. 62/659,408, filed on Apr. 18, 2018.

(51) Int. Cl.
*C07D 405/14* (2006.01)
*C07D 405/12* (2006.01)
*A61P 35/00* (2006.01)

(52) U.S. Cl.
CPC ............ *C07D 405/14* (2013.01); *A61P 35/00* (2018.01); *C07D 405/12* (2013.01)

(58) Field of Classification Search
CPC ...... C07D 405/12; C07D 405/14; A61P 35/00
See application file for complete search history.

(56) References Cited

U.S. PATENT DOCUMENTS

| | | |
|---|---|---|
| 5,221,599 A | 6/1993 | Katoh et al. |
| 5,296,497 A | 3/1994 | Hartog et al. |
| 5,385,917 A | 1/1995 | Ueno et al. |
| 5,514,505 A | 5/1996 | Limburg et al. |
| 5,626,791 A | 5/1997 | Fenkl et al. |
| 5,629,200 A | 5/1997 | Furukawa et al. |
| 6,051,575 A | 4/2000 | Blythin et al. |
| 10,689,371 B2 | 6/2020 | Cote et al. |
| 2004/0092740 A1 | 5/2004 | Dumas et al. |
| 2005/0245529 A1 | 11/2005 | Stenkamp et al. |
| 2008/0194803 A1 | 8/2008 | Sinclair et al. |
| 2009/0030197 A1 | 1/2009 | Chew et al. |
| 2009/0047278 A1 | 2/2009 | Owa et al. |
| 2009/0143353 A1 | 6/2009 | Kawakami et al. |
| 2015/0361067 A1 | 12/2015 | Collins et al. |
| 2016/0222047 A1 | 8/2016 | Zhong et al. |
| 2017/0073335 A1 | 3/2017 | Kanno et al. |
| 2018/0200238 A1 | 7/2018 | Watanabe et al. |
| 2019/0343816 A1 | 11/2019 | Yamano et al. |

FOREIGN PATENT DOCUMENTS

| | | |
|---|---|---|
| BR | PI0704074 A2 | 1/2010 |
| CA | 2100642 A1 | 1/1994 |
| CN | 101851218 A | 10/2010 |
| CN | 106727549 A | 5/2017 |
| DE | 10148617 A1 | 4/2003 |
| DE | 10219294 A1 | 11/2003 |
| EP | 372657 A1 | 6/1990 |
| JP | S63-017850 A | 1/1988 |
| JP | H02-255673 A | 10/1990 |
| JP | H02-255674 A | 10/1990 |
| JP | H02-269352 A | 11/1990 |
| JP | H02-282354 A | 11/1990 |
| JP | H03-130280 A | 6/1991 |
| JP | H04-046175 A | 2/1992 |
| JP | H10-287654 A | 10/1998 |
| JP | 2006145294 A | 6/2006 |
| JP | 2010254629 A | 11/2010 |
| JP | 2019168611 A | 10/2019 |
| RU | 2509770 C2 | 3/2014 |

(Continued)

OTHER PUBLICATIONS

Gaikwad et al., The use of bioisosterism in drug design and molecular modification. Am J PharmTech Res. 2(4): 1-23 (2012).

(Continued)

*Primary Examiner* — Erich A Leeser

(74) *Attorney, Agent, or Firm* — McCarter & English, LLP; Steven G. Davis; Michael J. DeGrazia

(57) ABSTRACT

Provided are novel compounds of Formula (I):

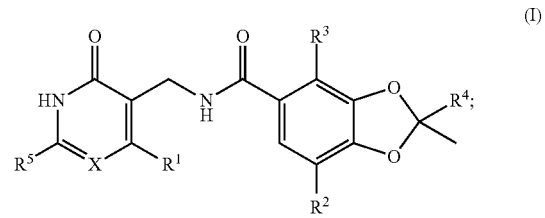

and pharmaceutically acceptable salts thereof, which are useful for treating a variety of diseases, disorders or conditions, associated with methyl modifying enzymes. Also provided are pharmaceutical compositions comprising the novel compounds of Formula (I), pharmaceutically acceptable salts thereof, and methods for their use in treating one or more diseases, disorders or conditions, associated with methyl modifying enzymes.

34 Claims, No Drawings

Specification includes a Sequence Listing.

(56) References Cited

FOREIGN PATENT DOCUMENTS

| | | |
|---|---|---|
| WO | 9726884 A1 | 7/1997 |
| WO | 9921422 A1 | 5/1999 |
| WO | 2000018761 A1 | 4/2000 |
| WO | 2002016333 A2 | 2/2002 |
| WO | 2002016352 A1 | 2/2002 |
| WO | 2002006229 A3 | 7/2002 |
| WO | 2002055072 A1 | 7/2002 |
| WO | 2002074307 A1 | 9/2002 |
| WO | 2002/081443 A1 | 10/2002 |
| WO | 2002085895 A1 | 10/2002 |
| WO | 2003029223 A1 | 4/2003 |
| WO | 2003035635 A1 | 5/2003 |
| WO | 2003059258 A2 | 7/2003 |
| WO | 2003062392 A2 | 7/2003 |
| WO | 2003075858 A2 | 9/2003 |
| WO | 2003086386 A1 | 10/2003 |
| WO | 2002016327 | 11/2003 |
| WO | 2003059898 A3 | 2/2004 |
| WO | 2004013120 A1 | 2/2004 |
| WO | 2004022023 A1 | 3/2004 |
| WO | 2004026274 A1 | 4/2004 |
| WO | 2005011686 A1 | 2/2005 |
| WO | 2005030704 A1 | 4/2005 |
| WO | 2005049008 A1 | 6/2005 |
| WO | 2005049627 A1 | 6/2005 |
| WO | 2005100321 A1 | 10/2005 |
| WO | 2005/110410 A2 | 11/2005 |
| WO | 2005112932 A2 | 12/2005 |
| WO | 2006003068 A2 | 1/2006 |
| WO | 2006/014136 A1 | 2/2006 |
| WO | 2006040318 A2 | 4/2006 |
| WO | 2006046914 A1 | 5/2006 |
| WO | 2006058648 A2 | 6/2006 |
| WO | 2006090930 A1 | 8/2006 |
| WO | 2006096807 A1 | 9/2006 |
| WO | 2006103449 A2 | 10/2006 |
| WO | 2006110447 A2 | 10/2006 |
| WO | 2006125119 A1 | 11/2006 |
| WO | 2006127205 A2 | 11/2006 |
| WO | 2006129609 A1 | 12/2006 |
| WO | 2006130403 A1 | 12/2006 |
| WO | 2007011820 A2 | 1/2007 |
| WO | 2007/014154 A2 | 2/2007 |
| WO | 2007019083 A1 | 2/2007 |
| WO | 2007081630 A2 | 7/2007 |
| WO | 2007085136 A1 | 8/2007 |
| WO | 2007107758 A1 | 9/2007 |
| WO | 2007138037 A1 | 12/2007 |
| WO | 2008027648 A2 | 3/2008 |
| WO | 2008029168 A2 | 3/2008 |
| WO | 2008052256 A1 | 5/2008 |
| WO | 2008054252 A1 | 5/2008 |
| WO | 2008141081 A1 | 11/2008 |
| WO | 2009054914 A1 | 4/2009 |
| WO | 2009136995 A2 | 11/2009 |
| WO | 2010008761 A1 | 1/2010 |
| WO | 2010019772 A2 | 2/2010 |
| WO | 2010137738 A1 | 12/2010 |
| WO | 2011004018 A1 | 1/2011 |
| WO | 2011006653 A1 | 1/2011 |
| WO | 2011084657 A1 | 7/2011 |
| WO | 2011091757 A1 | 8/2011 |
| WO | 2011/159297 A1 | 12/2011 |
| WO | 2011156775 A2 | 12/2011 |
| WO | 2012013725 A1 | 2/2012 |
| WO | 2012016879 A1 | 2/2012 |
| WO | 2012036278 A1 | 3/2012 |
| WO | 2012045196 A1 | 4/2012 |
| WO | 2012126922 A1 | 9/2012 |
| WO | 2013025484 A1 | 2/2013 |
| WO | 2013025584 A1 | 2/2013 |
| WO | 2013065835 A1 | 5/2013 |
| WO | 2013142712 A1 | 9/2013 |
| WO | 2014034898 A1 | 3/2014 |
| WO | 2014066435 A1 | 5/2014 |
| WO | 2014160401 A1 | 10/2014 |
| WO | 2014177464 A2 | 11/2014 |
| WO | 2015034271 A1 | 3/2015 |
| WO | 2015069110 A1 | 5/2015 |
| WO | 2015141616 A1 | 9/2015 |
| WO | 2016038540 A1 | 3/2016 |
| WO | 2017018499 A1 | 2/2017 |
| WO | 2017121648 A1 | 7/2017 |
| WO | 2017139414 A1 | 8/2017 |
| WO | 2018013789 A1 | 1/2018 |
| WO | 2018170513 A1 | 9/2018 |
| WO | 2018218070 A2 | 11/2018 |
| WO | 2019084271 A1 | 5/2019 |
| WO | 2019086890 A1 | 5/2019 |
| WO | 2019124537 A1 | 6/2019 |
| WO | 2019140322 A1 | 7/2019 |
| WO | 2019191558 A1 | 10/2019 |
| WO | 2019204490 A1 | 10/2019 |

OTHER PUBLICATIONS

Venkatesan et al., Bioisoterism Review—an biological modification. World Journal of Pharmacy and Pharmaceutical Sciences. 6(9): 1918-49 (2017).

Kung et al., Design and Synthesis of Pyridone-Containing 3,4-Dihydroisoquinoline-1(2H)-ones as a Novel Class of Enhancer of Zeste Homolog 2 (EZH2) Inhibitors J Med Chem. Sep. 22, 2016;59(18):8306-25.

Copending U.S. Appl. No. 17/057,225, filed Nov. 20, 2020.

SEQUENCE LISTING

<160> NUMBER OF SEQ ID NOS: 3

<210> SEQ ID NO 1
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (11)..(11)
<223> OTHER INFORMATION: LysMe3

<400> SEQUENCE: 1

Arg Lys Gln Leu Ala Thr Lys Ala Ala Arg Xaa Ser Ala Pro Ala Thr
1               5                   10                  15

Gly Gly Val Lys Lys Pro
            20

<210> SEQ ID NO 2
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (11)..(11)
<223> OTHER INFORMATION: LysMe1

<400> SEQUENCE: 2

Arg Lys Gln Leu Ala Thr Lys Ala Ala Arg Xaa Ser Ala Pro Ala Thr
1               5                   10                  15

Gly Gly Val Lys Lys Pro
            20

<210> SEQ ID NO 3
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Arg Lys Gln Leu Ala Thr Lys Ala Ala Arg Lys Ser Ala Pro Ala Thr
1               5                   10                  15

Gly Gly Val Lys Lys Pro
            20

MODULATORS OF METHYL MODIFYING ENZYMES, COMPOSITIONS AND USES THEREOF

RELATED APPLICATIONS

This application is a continuation of U.S. application Ser. No. 16/387,851, filed Apr. 18, 2019, which claims the benefit of priority to U.S. Provisional Application No. 62/659,408, filed Apr. 18, 2018, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Jun. 25, 2019, is named 124033-00203_SL.txt and is 1.513 bytes in size.

BACKGROUND

Eukaryotic chromatin is composed of macromolecular complexes called nucleosomes. A nucleosome has 147 base pairs of DNA wrapped around a protein octamer having two subunits of each of histone protein H2A, H2B, H3, and H4. Histone proteins are subject to post-translational modifications which in turn affect chromatin structure and gene expression. One type of post-translational modification found on histones is methylation of lysine and arginine residues. Histone methylation plays a critical role in the regulation of gene expression in eukaryotes. Methylation affects chromatin structure and has been linked to both activation and repression of transcription (Zhang and Reinberg, Genes Dev. 15:2343-2360, 2001). Enzymes that catalyze attachment and removal of methyl groups from histones are implicated in gene silencing, embryonic development, cell proliferation, and other processes.

One class of histone methylases is characterized by the presence of a SET domain, comprising about 130 amino acids. EZH2 is an example of a human SET-domain containing methylase. EZH2 associates with EED (Embryonic Ectoderm Development) and SUZ12 (suppressor of zeste 12 homolog) to form a complex known as PRC2 (Polycomb Group Repressive Complex 2) having the ability to tri-methylate histone H3 at lysine 27 (Cao and Zhang, Mol. Cell 15:57-67, 2004). PRC2 complexes can also include RBAP46 and RBAP48 subunits. Another example is the related methylase EZH1.

The oncogenic activities of EZH2 have been shown by a number of studies in various different cancer types. ~15-20% GCB-DLBCLs harbor a gain-of-function mutation in EZH2 (Y641 residue) and these cells are hypersensitive to EZH2 inhibition both in vitro and in vivo (McCabe et al, 2012; Bradley et al, 2014). In cell line experiments, overexpression of EZH2 induces cell invasion, growth in soft agar, and motility, while knockdown of EZH2 inhibits cell proliferation and cell invasion (Kleer et al., 2003, Proc. Nat. Acad. Sci. USA 100:11606-11611; Varambally et al., (2002), "The polycomb group protein EZH2 is involved in progression of prostate cancer," Nature 419, 624-629). It has been shown that EZH2 represses the expression of several tumor suppressors, including E-cadherin, DAB2IP and RUNX3 among others. In xenograft models, EZH2 knockdown inhibits tumor growth and metastasis. It has been shown that down modulation of EZH2 in murine models blocks prostate cancer metastasis (Min et al., "An oncogene-tumor suppressor cascade drives metastatic prostate cancer by coordinately activating Ras and nuclear factor-kappaB," Nat Med. 2010 March; 16(3):286-94). Recently, it was demonstrated that EZH2 is over-expressed in neuroendocrine tumors and inhibition of EZH2 in mouse tumors restore androgen dependence (Ku et al, Science, 355, 2017). EZH2 overexpression is associated with aggressiveness of certain cancers such as breast cancer (Kleer et al., Proc. Nat. Acad. Sci. USA 100:11606-11611, 2003). Recent studies also suggest that prostate cancer specific oncogenic fusion gene TMPRSS2-ERG induces repressive epigenetic programs via direct activation of EZH2 (Yu et al., "An Integrated Network of Androgen Receptor, Polycomb, and TMPRSS2-ERG Gene Fusions in Prostate Cancer Progression," Cancer Cell. 2010 May 18; 17(5):443-454).

Given their role in the regulation of diverse biological processes, methyl modifying enzymes, in particular EZH2 and mutant forms thereof, are attractive targets for modulation.

SUMMARY

It has now been found that compounds described herein, and pharmaceutically acceptable compositions thereof, modulate the activity of EZH2 (See e.g., Table 5). Such compounds include those of structural Formula I:

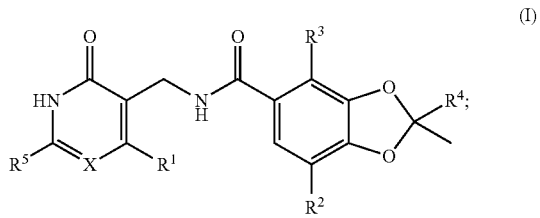

or a pharmaceutically acceptable salt thereof, wherein each of $R^1$, $R^2$, $R^3$, $R^4$, $R^5$, X and X are defined herein.

In one aspect, it has also been found that certain compounds described herein have increased residence time (e.g., >100 hours) and enhanced permeability. An increase in residence time (i.e., slower off rate) and/or permeability has been found to correlate with improved cellular potency.

The disclosed compounds, pharmaceutically acceptable salts, and pharmaceutically acceptable compositions, are useful for treating a variety of conditions associated with methyl modifying enzymes. These conditions include e.g., one or more cancers.

DETAILED DESCRIPTION

1. General Description of Compounds
Provided are compounds of Formula I:

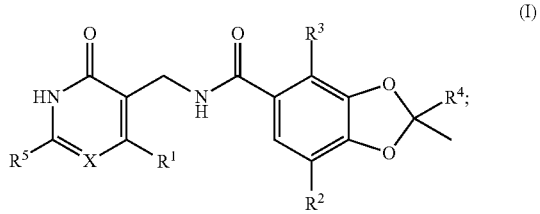

or a pharmaceutically acceptable salt thereof, wherein:
- $R^1$ is halo, —S($C_1$-$C_4$)alkyl, —S($C_3$-$C_7$)cycloalkyl, or —S[halo($C_1$-$C_4$)alkyl];
- X is CH or N;
- $R^2$ is hydrogen, halo, ($C_1$-$C_4$)alkyl, or halo($C_1$-$C_4$)alkyl;
- $R^3$ is halo, ($C_1$-$C_4$)alkyl, or halo($C_1$-$C_4$)alkyl;
- $R^4$ is ($C_3$-$C_7$)cycloalkyl or 4-7 membered heterocyclyl, each of which are optionally substituted with 1 to 3 groups selected from halo, ($C_1$-$C_4$)alkyl, halo($C_1$-$C_4$)alkyl, ($C_1$-$C_4$)alkoxy, halo($C_1$-$C_4$)alkoxy, and —$NR^aR^b$;
- $R^a$ is hydrogen, ($C_1$-$C_4$)alkyl, or halo($C_1$-$C_4$)alkyl;
- $R^b$ is ($C_1$-$C_4$)alkyl, halo($C_1$-$C_4$)alkyl, or 4-7 membered heterocyclyl, wherein said heterocyclyl is optionally substituted with 1 to 3 groups selected from halo, ($C_1$-$C_4$)alkyl, halo($C_1$-$C_4$)alkyl, ($C_1$-$C_4$)alkoxy, and halo($C_1$-$C_4$)alkoxy; or
- $R^a$ and $R^b$ together with the nitrogen atom to which they are attached form a 4-7 membered heterocyclyl optionally substituted with 1 to 3 groups selected from halo, ($C_1$-$C_4$)alkyl, halo($C_1$-$C_4$)alkyl, and —$OR^c$;
- $R^c$ is ($C_1$-$C_4$)alkyl, halo($C_1$-$C_4$)alkyl, or ($C_3$-$C_7$)cycloalkyl; and
- $R^5$ is halo, ($C_1$-$C_4$)alkyl, or halo($C_1$-$C_4$)alkyl.

2. Definitions

When used in connection to describe a chemical group that may have multiple points of attachment, a hyphen (-) designates the point of attachment of that group to the variable to which it is defined. For example, —S($C_3$-$C_7$)cycloalkyl and —S[halo($C_1$-$C_4$)alkyl] mean that the point of attachment for this group occurs on the sulfur atom.

The terms "halo" and "halogen" as used herein refer to an atom selected from fluorine (fluoro, —F), chlorine (chloro, —Cl), bromine (bromo, —Br), and iodine (iodo, —I).

The term "alkyl," as used herein, refers to a monovalent saturated, straight- or branched-chain hydrocarbon radical, having unless otherwise specified, 1-10 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, and the like.

The term "haloalkyl" includes mono, poly, and perhaloalkyl groups where the halogens are independently selected from fluorine, chlorine, bromine, and iodine.

"Alkoxy" is an alkyl group which is attached to another moiety via an oxygen linker (—O(alkyl)). Non-limiting examples include methoxy, ethoxy, propoxy, and butoxy.

"Haloalkoxy" is a haloalkyl group which is attached to another moiety via an oxygen atom such as, e.g., but are not limited to —$OCHCF_2$ or —$OCF_3$.

The term "cycloalkyl" refers to a 3- to 12-membered (e.g., 3- to 7-membered) monocyclic, bicyclic (e.g., a bridged or spiro bicyclic ring), or polycyclic (e.g., tricyclic), hydrocarbon ring system that is completely saturated. Monocyclic cycloalkyl groups include, without limitation, cyclopropyl, cyclobutyl, cyclopentyl, cyclohexyl, cycloheptyl, and cyclooctyl. Bridged bicyclic cycloalkyl groups include, without limitation, bicyclo[3.2.1]octane, bicyclo[2.2.1]heptane, bicyclo[3.1.0]hexane, bicyclo[1.1.1]pentane, and the like. Spiro bicyclic cycloalkyl groups include, e.g., spiro[3.6]decane, spiro[4.5]decane, and the like. Fused cycloalkyl rings include, e.g., decahydronaphthalene, octahydropentalene, and the like. Where specified as being optionally substituted or substituted, substituents on a cycloalkyl (e.g., in the case of an optionally substituted cycloalkyl) may be present on any substitutable position and, include, e.g., the position at which the cycloalkyl group is attached.

The term "heterocyclyl" means a 3-12 membered (e.g., a 4-, 5-, 6- and 7-membered) saturated or partially unsaturated heterocyclic ring containing 1 to 4 heteroatoms independently selected from N, O, and S. It can be monocyclic, bicyclic (e.g., a bridged, fused, or spiro bicyclic ring), or tricyclic. The terms "heterocycle", "heterocyclyl", "heterocyclyl ring", "heterocyclic group", "heterocyclic moiety", and "heterocyclic radical", are used interchangeably herein. A heterocyclyl ring can be attached to its pendant group at any heteroatom or carbon atom that results in a stable structure. Examples of such saturated or partially unsaturated heterocyclic radicals include, without limitation, tetrahydrofuranyl, tetrahydrothienyl, terahydropyranyl, pyrrolidinyl, pyridinonyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, oxetanyl, azetidinyl and tetrahydropyrimidinyl. A heterocyclyl group may be mono- or bicyclic. The term "heterocyclyl" also includes, e.g., unsaturated heterocyclic radicals fused to another unsaturated heterocyclic radical or aryl or heteroaryl ring, such as for example, tetrahydronaphthyridine, indolinone, dihydropyrrolotriazole, imidazopyrimidine, quinolinone, dioxaspirodecane. Where specified as being optionally substituted or substituted, substituents on a heterocyclyl (e.g., in the case of an optionally substituted heterocyclyl) may be present on any substitutable position and, include, e.g., the position at which the heterocyclyl group is attached.

The term "spiro" refers to two rings that shares one ring atom (e.g., carbon).

The term "fused" refers to two rings that share two adjacent ring atoms with one another.

The term "bridged" refers to two rings that share three or more ring atoms with one another.

As used herein, "geometric isomer" refers to isomers that differ in the orientation of substituent atoms in relationship to a cycloalkyl ring, i.e., cis or trans isomers. When a disclosed compound is named or depicted by structure without indicating a particular cis or trans geometric isomer form, it is to be understood that the name or structure encompasses one geometric isomer free of other geometric isomers, mixtures of geometric isomers, or mixtures enriched in one geometric isomer relative to its corresponding geometric isomer.

Unless otherwise specified, when the stereochemistry of a disclosed compound is named or depicted by structure, the named or depicted stereoisomer is at least 60%, 70%, 80%, 90%, 99% or 99.9% by weight pure relative to all of the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer. Enantiomers may be resolved by methods known to those skilled in the art, for example by formation of diastereoisomeric salts which may be separated, for example, by crystallization; formation of diastereoisomeric derivatives or complexes which may be separated, for example, by crystallization, supercritical fluid or liquid chromatography; selective reaction of one enantiomer with an enantiomer-specific reagent, for example enzymatic esterification; or supercritical fluid or liquid chromatography in a chiral environment, for example on a chiral support for example silica with a bound chiral ligand or in the presence of a chiral solvent. Specific enantiomers may also be synthesized by asymmetric synthesis using optically active reagents, substrates, catalysts or solvents, or by converting one enantiomer into the other by asymmetric transformation.

Unless otherwise specified, when a disclosed compound is named or depicted by structure without indicating the stereochemistry, and the compound has at least one chiral center or at least one geometric isomer, or both, the name or structure encompasses one enantiomer or geometric isomer of the compound free from the corresponding optical isomer or geometric isomer, a racemic mixture of the compound and mixtures enriched in one enantiomer or geometric isomer relative to its corresponding optical isomer or geometric isomer.

Unless otherwise specified, when only some of the stereochemical centers in a disclosed compound are depicted or named by structure, the named or depicted configuration is enriched relative to the remaining configurations, for example, by a molar excess of at least 60%, 70%, 80%, 90%, 99% or 99.9%. For example, the substructure:

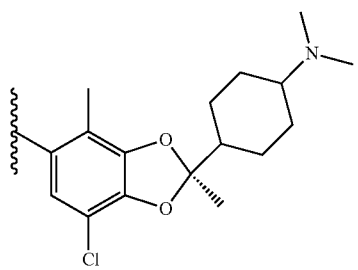 [SMILES: *c1cc(Cl)c2c(c1C)O[C@@](C)(C1CCC(N(C)C)CC1)O2]

means that that the configuration about the chiral carbon is stereochemically enriched as R (e.g., by a molar excess of at least 60%, 70%, 80%, 90%, 99% or 99.9%) and that the geometry about the cyclohexyl may be cis or trans, or a mixture thereof.

In certain instances, a disclosed compound is depicted by structure without indicating the stereochemistry, but is identified as being stereochemically enriched (e.g., "single enantiomer; single geometric isomer" or "single enantiomer" in instances where geometric isomers are not possible). For example, unless specified otherwise, Example 1

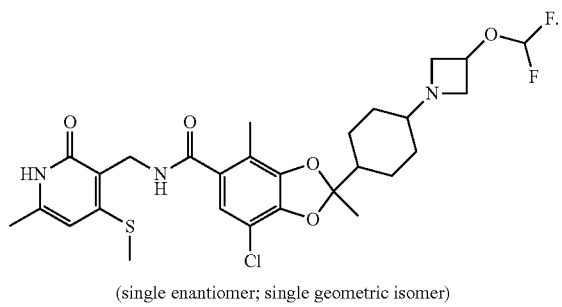

(single enantiomer; single geometric isomer)

means that the configuration about the chiral dioxolanyl carbon is stereochemically enriched as R (e.g., by a molar excess of at least 60%, 70%, 80%, 90%, 99% or 99.9%) or is stereochemically enriched as S (e.g., by a molar excess of at least 60%, 70%, 80%, 90%, 99% or 99.9%) and that the geometric configuration about the cyclohexyl ring is enriched as cis (e.g., by a molar excess of at least 60%, 70%, 80%, 90%, 99% or 99.9%) or is enriched as trans (e.g., by a molar excess of at least 60%, 70%, 80%, 90%, 99% or 99.9%).

The term "patient," as used herein, means an animal, such as a mammal, and such as a human. The terms "subject" and "patient" may be used interchangeably.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The terms "treatment," "treat," and "treating" refer to reversing, alleviating, or inhibiting the progress of a disease or disorder, or one or more symptoms thereof, as described herein. Treatment may also be continued after symptoms have resolved, for example to delay recurrence.

Disease, disorder, and condition are used interchangeably herein.

The term "effective amount" or "therapeutically effective amount" refers to an amount of a compound described herein that will elicit a biological or medical response of a subject e.g., a dosage of between 0.01-100 mg/kg body weight/day. The terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The term "inhibit," "inhibition" or "inhibiting" includes a decrease in the baseline activity of a biological activity or process.

The compounds described herein may be present in the form of pharmaceutically acceptable salts. For use in medicines, the salts of the compounds described herein refer to non-toxic "pharmaceutically acceptable salts." Pharmaceutically acceptable salt forms include pharmaceutically acceptable acidic/anionic or basic/cationic salts. Suitable pharmaceutically acceptable acid addition salts of the compounds described herein include e.g., salts of inorganic acids (such as hydrochloric acid, hydrobromic, phosphoric, nitric, and sulfuric acids) and of organic acids (such as, acetic acid, benzenesulfonic, benzoic, methanesulfonic, and p-toluenesulfonic acids).

3. Description of Exemplary Compounds

In a first embodiment, the present disclosure provides a compound of Formula I:

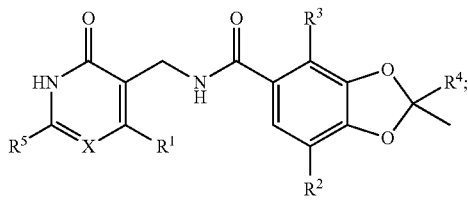
(I)

or a pharmaceutically acceptable salt thereof, wherein the variables are as above for Formula I.

In a second embodiment, in the compounds of Formula I,
$R^1$ is halo or —S($C_1$-$C_4$)alkyl;
$R^2$ is halo;
$R^3$ is ($C_1$-$C_4$)alkyl;
$R^4$ is ($C_3$-$C_7$)cycloalkyl or ($C_4$-$C_7$)heterocyclyl, each of which are optionally substituted with 1 to 2 groups selected from halo($C_1$-$C_4$)alkyl and —$NR^aR^b$;
$R^a$ is hydrogen or ($C_1$-$C_4$)alkyl;
$R^b$ is ($C_1$-$C_4$)alkyl or ($C_4$-$C_7$)heterocyclyl, wherein said heterocyclyl is optionally substituted with halo($C_1$-$C_4$) alkyl; or
$R^a$ and $R^b$ together with the nitrogen atom to which they are attached form a 4-7 membered nitrogen containing heterocyclyl optionally substituted with 1 to 3 groups selected from halo and —$OR^c$;
$R^c$ is ($C_1$-$C_4$)alkyl, halo($C_1$-$C_4$)alkyl, or ($C_3$-$C_7$)cycloalkyl; and
$R^5$ is halo or ($C_1$-$C_4$)alkyl.

In a third embodiment, the compound of Formula I is of Formula II:

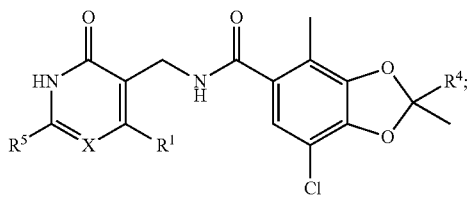
(II)

or a pharmaceutically acceptable salt thereof, wherein the remaining variables are as described above for Formula I or the second embodiment.

In a fourth embodiment, $R^1$ in the compound of Formula I or Formula II is chloro, wherein the remaining variables are as described above for Formula I or the second embodiment.

In a fifth embodiment, $R^1$ in the compound of Formula I or Formula II is —$SCH_3$, wherein the remaining variables are as described above for Formula I or the second embodiment.

In a sixth embodiment, $R^4$ in the compound of Formula I or Formula II is cyclohexyl or piperidinyl, each of which are optionally substituted with 1 to 2 groups selected from halo($C_1$-$C_4$)alkyl and —$NR^aR^b$, wherein the remaining variables are as described above for Formula I or the second, fourth, or fifth embodiment.

In a seventh embodiment, the compound of Formula I or Formula II is of the Formula III:

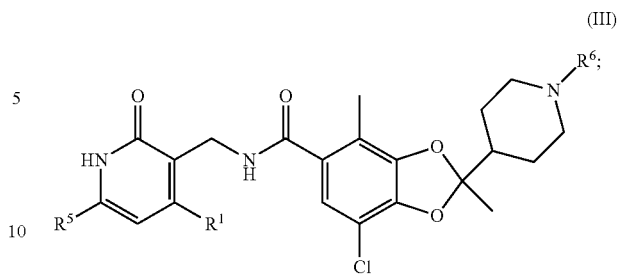
(III)

or a pharmaceutically acceptable salt thereof, wherein $R^6$ is halo($C_1$-$C_4$)alkyl, and wherein the remaining variables are as described above for Formula I or the second, fourth, or fifth embodiment.

In an eighth embodiment, the compound of Formula I, Formula II, or Formula III is of the Formula IV:

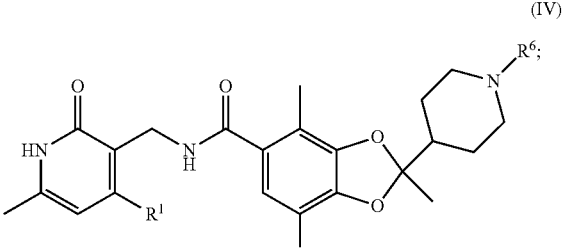
(IV)

or a pharmaceutically acceptable salt thereof, wherein the remaining variables are as described above for Formula I or the second, fourth, fifth, or seventh embodiment.

In a ninth embodiment, the compound of Formula I or Formula II is of the Formula V:

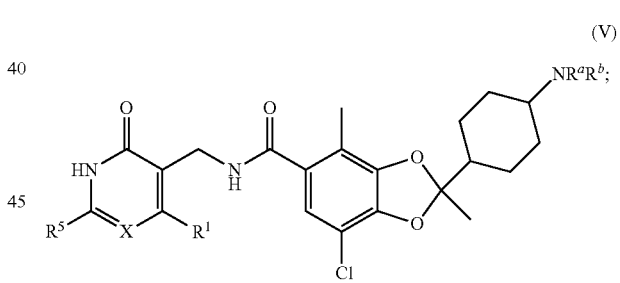
(V)

or a pharmaceutically acceptable salt thereof, wherein the remaining variables are as described above for Formula I or the second, fourth, or fifth embodiment.

In a tenth embodiment, the compound of Formula I, Formula II, or Formula V is of the Formula VI or VII:

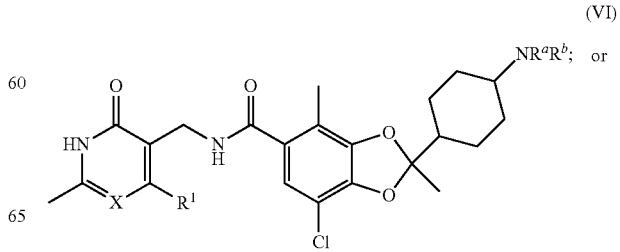
(VI)

(VII)

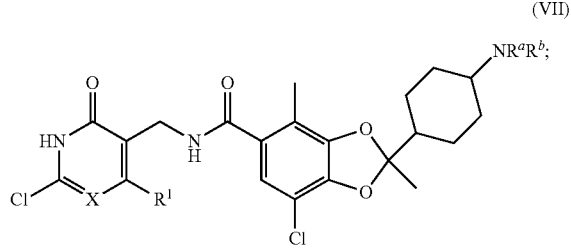

or a pharmaceutically acceptable salt thereof, wherein the remaining variables and features are as described above for Formula I or the second, fourth, or fifth embodiment.

In an eleventh embodiment, $R^b$ in the compounds of Formula I, Formula II, Formula V, Formula VI, and Formula VII is $(C_1\text{-}C_4)$alkyl or oxatanyl, wherein said oxetanyl is optionally substituted with halo$(C_1\text{-}C_4)$alkyl; or $R^a$ and $R^b$ together with the nitrogen atom to which they are attached form an azetidinyl optionally substituted with halo or —$OR^c$, wherein the remaining variables and features are as described above for Formula I or the second, fourth, or fifth embodiment.

In a twelfth embodiment, $R^a$ in the compounds of Formula I, Formula II, Formula V, Formula VI, and Formula VII is hydrogen or methyl; and $R^b$ is methyl or oxatanyl, wherein said oxetanyl is optionally substituted with —$CH_2F$ or —$CF_3$, wherein the remaining variables and features are as described above for Formula I or the second, fourth, fifth, or eleventh embodiment.

In a thirteenth embodiment, $R^a$ and $R^b$ in the compounds of Formula I, Formula II, Formula V, Formula VI, and Formula VII together with the nitrogen atom to which they are attached form an azetidinyl optionally substituted with 1 to 2 fluoro or —$OR^c$; and $R^c$ is —$CH_3$, —$CHF_2$, or cyclopropyl, wherein the remaining variables and features are as described above for Formula I or the second, fourth, fifth, or eleventh embodiment.

In a fourteenth embodiment, the configuration of the 1,3-dioxolanyl and the $NR^aR^b$ group in any one of Formula I, II, V, VI, and VII are oriented trans about the cyclohexyl, wherein the remaining features are as described above for Formula I or the second, fourth, fifth, sixth, eleventh, twelfth, or thirteenth embodiments. Alternatively, the configuration of the 1,3-dioxolanyl and the $NR^aR^b$ group of Formula I, II, V, VI, and VII, are oriented cis about the cyclohexyl, wherein the remaining features are as described above for Formula I or the second, fourth, fifth, sixth, eleventh, twelfth, or thirteenth embodiment.

In a fifteenth embodiment, the stereochemical configuration of the chiral center of the 1,3-dioxolanyl in any one of Formula I, II, III, IV, V, VI, and VII is R, wherein the remaining features are as described above for Formula I or the second, fourth, fifth, sixth, eleventh, twelfth, thirteenth, or fourteenth embodiment. Alternatively, the stereochemical configuration of the chiral center of the 1,3-dioxolanyl in any one of Formula I, II, III, IV, V, VI, and VII is S, wherein the remaining features are as described above for Formula I or the second, fourth, fifth, sixth, eleventh, twelfth, thirteenth, or fourteenth embodiment.

Specific examples of compounds are provided in the EXEMPLIFICATION section and are included as part of a fourteenth embodiment herein. Pharmaceutically acceptable salts as well as the neutral forms of these compounds are also included. In one aspect, the present disclosure includes racemic forms of any compound described herein.

4. Uses, Formulation and Administration

In some embodiments, the present disclosure provides a composition comprising a compound described herein or a pharmaceutically acceptable derivative thereof and a pharmaceutically acceptable carrier. The amount of compound in a provided composition is such that is effective to measurably modulate a histone methyl modifying enzyme, or a mutant thereof, in a biological sample or in a patient.

In certain embodiments, a composition described herein is formulated for administration to a patient in need of such composition. Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered orally, intraperitoneally or intravenously. Sterile injectable forms of the compositions described herein may be aqueous or oleaginous suspension. These suspensions may be formulated according to techniques known in the art using suitable dispersing or wetting agents and suspending agents.

In some embodiments, the compositions are administered orally.

A specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound described herein in the composition will also depend upon the particular compound in the composition.

Compounds and compositions described herein are generally useful for the modulating of activity of one or more enzymes involved in epigenetic regulation and in particular EZH1 and EZH2 and, even more specifically EZH2 and mutant forms thereof. In some embodiments, compounds described herein down-regulate or suppress the activity of EZH2. In some embodiments, compounds described herein are antagonists of EZH2 activity. In some embodiments, compounds described herein down-regulate or suppress the activity of EZH1. In some embodiments, compounds described herein are antagonists of EZH1 activity.

In some embodiments, compounds and compositions described herein are useful in treating diseases and/or disorders associated with overexpression of EZH1 or EZH2 and/or expression of a mutant form of EZH2, such as those mutant forms that alter EZH2 substrate activity. The study of EZH2 deletions, missense and frameshift mutations suggest that EZH2 functions as a tumor suppressor in blood disorders such as myelodysplastic syndromes (MDS) and myeloid malignancies (Ernst et al., Nat Genet. 2010 August; 42(8):722-6; Nikoloski et al., Nat Genet. 2010 Aug; 42(8): 665-7). In some embodiments, compounds and compositions described herein are useful in treating diseases and/or disorders associated with the presence of EZH2 having a Y641N, Y641C, Y641F, Y641H, Y641S, A677G, or A687 mutation. In a particular aspect of this embodiment, the EZH2 has a Y641N mutation.

In some embodiments, the present disclosure provides a method of treating a subject suffering from a disease and/or disorder associated with overexpression of EZH1 or EZH2 and/or expression of a mutant form of EZH2 comprising the step of administering a compound described herein, or a pharmaceutically acceptable salt or composition thereof. In some embodiments, the above method additionally comprises the preliminary step of determining if the subject is overexpressing EZH2 or expressing a mutant form of EZH2.

In some embodiments, the disease or disorder associated with the presence of a mutant form of EZH2 is a human B cell lymphoma. In some embodiments, the disease and/or disorder associated with the presence of Y641N EZH2 is follicular lymphoma or diffuse large-B-cell lymphoma. In some embodiments, compounds or compositions described herein are useful in treating blood disorders, such as myelodysplastic syndromes, leukemia, anemia and cytopenia. Sneeringer et al., "Coordinated activities of wild-type plus mutant EZH2 drive tumor-associated hypertrimethylation of lysine 27 on histone H3 (H3K27) in human B-cell lymphomas," Sneeringer et al., Proc. Natl Acad. Sci. 2010 December; 109(48):20980-20985.

In some embodiments, compounds and compositions described herein are useful in treating diseases and/or disorders associated with cellular proliferation. In some embodiments, compounds and compositions described herein are useful in treating diseases and/or disorders associated with misregulation of cell cycle or DNA repair. In some embodiments, compounds and compositions described herein are useful in treating cancer.

In one aspect, cancers that may be treated by the compounds, compositions and methods described herein include, but are not limited to Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, clear cell carcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma.

In one aspect, the cancer treated by the compounds, compositions, and methods described herein is selected from adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NKcell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor Tlymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In one aspect, the cancer treated by the compounds, compositions, and methods described herein is selected from adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, acute myeloid leukemia (AML), diffuse large B-cell lymphoma (DLBCL), ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, and Wilms' tumor.

In one aspect, the cancer treated by the compounds, compositions, and methods described herein are selected from breast cancer, prostate cancer, colon cancer, renal cell carcinoma, glioblastoma multiforme cancer, bladder cancer, melanoma, bronchial cancer, lymphoma and liver cancer.

Also provided is the use of a compound described herein, or a pharmaceutically acceptable salt thereof, or a composition comprising a disclosed compound or pharmaceutically acceptable salt thereof, for the manufacture of a medicament for treating a condition described herein. Also provided is a compound described herein, or a pharmaceutically acceptable salt thereof, or a composition comprising a disclosed compound or pharmaceutically acceptable salt thereof, for use in treating a condition described herein.

Exemplification

The representative examples that follow are intended to help illustrate the invention, and are not intended to, nor should they be construed to, limit the scope of the invention.

Preparation of Intermediates

Intermediate 1: 3-(aminomethyl)-6-methyl-4-(methylthio)pyridin-2(1H)-one (hydrochloride salt)

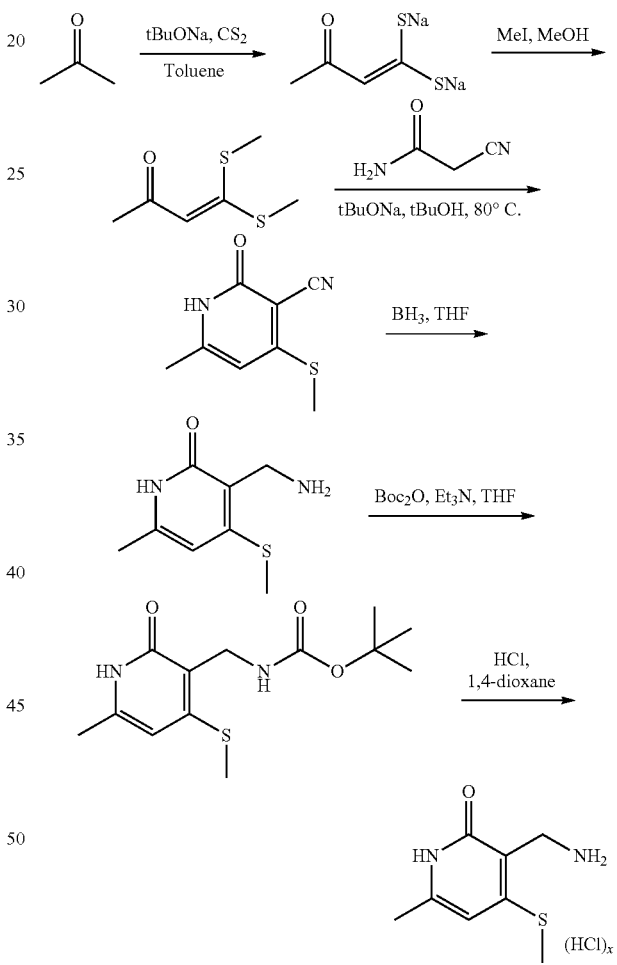

Intermediate 1

Step 1: Synthesis of sodium 3-oxobut-1-ene-1,1-bis(thiolate)

A mixture of sodium tert-butoxide (16.6 g, 172 mmol) in toluene (30 mL) was degassed under vacuum and purged with nitrogen (3 cycles). Acetone (5.0 g, 6.4 mL, 86 mmol) was then added at 0° C. followed by the slow addition of carbon disulfide (6.6 g, 5.24 mL, 86 mmol). The resulting mixture was stirred at 0° C. for 4 h, then filtered. The filter cake was dried under vacuum to give the title compound (15.4 g, crude) as a yellow solid, which was used in the next step without further purification.

Step 2: Synthesis of 4,4-bis(methylthio)but-3-en-2-one

To a solution of sodium 3-oxobut-1-ene-1,1-bis(thiolate) (15.4 g, 86.4 mmol) in methanol (90 mL) was slowly added iodomethane (24.5 g, 10.7 mL, 173 mmol). The mixture was stirred at 70° C. for 1 h then concentrated to dryness. Water (30 mL) was added and the desired product was extracted with ethyl acetate (60 mL×3). The combined organic layers were dried over sodium sulfate and concentrated under reduced pressure to give the title compound (6.8 g, 42% yield) as a brown oil, which was used in the next step without further purification. LCMS [M+H]$^+$ m/z: calc'd 163.0; found 163.0. $^1$H NMR (400 MHz, chloroform-d) δ 6.02 (s, 1H), 2.45 (s, 3H), 2.43 (s, 3H), 2.15 (s, 3H).

Step 3: Synthesis of 6-methyl-4-(methylthio)-2-oxo-1,2-dihydropyridine-3-carbonitrile To a solution of 4,4-bis(methylthio)but-3-en-2-one (2.9 g, 18 mmol) and 2-cyanoacetamide (1.5 g, 18 mmol) in tert-butanol (50 mL) was added sodium tert-butoxide (1.9 g, 20 mmol). The mixture was stirred at 80° C. for 12 h (two batches of the reaction were performed and combined at this stage). Water (20 mL) was added and the pH adjusted to 5-6 with 10% hydrochloric acid. The resulting mixture was filtered, and the filter cake was washed with petroleum ether (20 mL×2) then the cake was dried under vacuum to give the title compound (4.8 g, 74% yield) as an off-white solid, which was used in the next step without further purification. LCMS [M+H]$^+$ m/z: calc'd 181.0; found 181.0. $^1$H NMR (400 MHz, Dimethylsulfoxide-d$_6$) δ 6.27 (s, 1H), 2.56 (s, 3H), 2.25 (s, 3H).

Step 4: Synthesis of 3-(aminomethyl)-6-methyl-4-(methylthio)pyridin-2(1H)-one

A mixture of 6-methyl-4-(methylthio)-2-oxo-1,2-dihydropyridine-3-carbonitrile (3.6 g, 20 mmol) in tetrahydrofuran (50 mL) was degassed under vacuum and purged with nitrogen (3 cycles). Borane dimethylsulfide complex (10 M, 8.0 mL, 80 mmol) was then slowly added at 0° C. before the reaction mixture was warmed to 70° C. and stirred for 2 h. Methanol (15 mL) was slowly added at 0° C. to quench the reaction before the mixture was concentrated under reduced pressure to give the title compound (3.8 g, crude), as a light yellow solid, which was used in the next step without further purification. LCMS [M+H]$^+$ m/z: calc'd 185.1; found 185.0.

Step 5: Synthesis of tert-butyl ((6-methyl-4-(methylthio)-2-oxo-1,2-dihydropyridin-3-yl)methyl)carbamate To a solution of 3-(aminomethyl)-6-methyl-4-(methylthio)pyridin-2(1H)-one (3.6 g, 20 mmol) in tetrahydrofuran (80 mL) was added triethylamine (5.9 g, 8.1 mL, 59 mmol). The mixture was stirred for 30 min before di-tert-butyl dicarbonate (6.4 g, 29 mmol) was added and the reaction stirred at 25° C. for 12 h. The reaction mixture was then concentrated to dryness under reduced pressure, before water (35 mL) was added and the desired product extracted with a 5:1 mixture of petroleum ether/ethyl acetate (30 mL×3). The combined organic layers were dried over sodium sulfate and concentrated to give the title compound (5.8 g, crude) as a white solid, which was used in the next step without further purification. LCMS [M+H]$^+$ m/z: calc'd 285.12; found 284.9. $^1$H NMR (400 MHz, Dimethylsulfoxide-d$_6$) δ 6.05 (s, 1H), 4.03-4.00 (m, 2H), 2.42 (s, 3H), 2.15 (s, 3H), 1.39 (s, 9H).

Step 6: Synthesis of 3-(aminomethyl)-6-methyl-4-(methylthio)pyridin-2(1H)-one (hydrochloride salt)

To a solution of hydrogen chloride in 1,4-dioxane (4 M, 100 mL, 400 mmol) at 25° C. was added tert-butyl ((6-methyl-4-(methylthio)-2-oxo-1,2-dihydropyridin-3-yl) methyl)carbamate (5.0 g, 17.6 mmol). The reaction mixture was stirred at 25° C. for 2 h then concentrated to dryness under reduced pressure. The residue was washed with dichloromethane (30 mL×2) and ethyl acetate (30 mL) to give the title compound (4.5 g, crude, HCl salt) as a yellow solid, which was used in the next step without further purification. LCMS [M+H]$^+$ m/z: calc'd 185.1; found 185.0. $^1$H NMR (400 MHz, D$_2$O) δ 6.31 (s, 1H), 4.03 (s, 2H), 2.41 (s, 3H), 2.18 (s, 3H).

Intermediate 2: 5-(aminomethyl)-2-methyl-6-(methylthio)pyrimidin-4(3H)-one (hydrochloride salt)

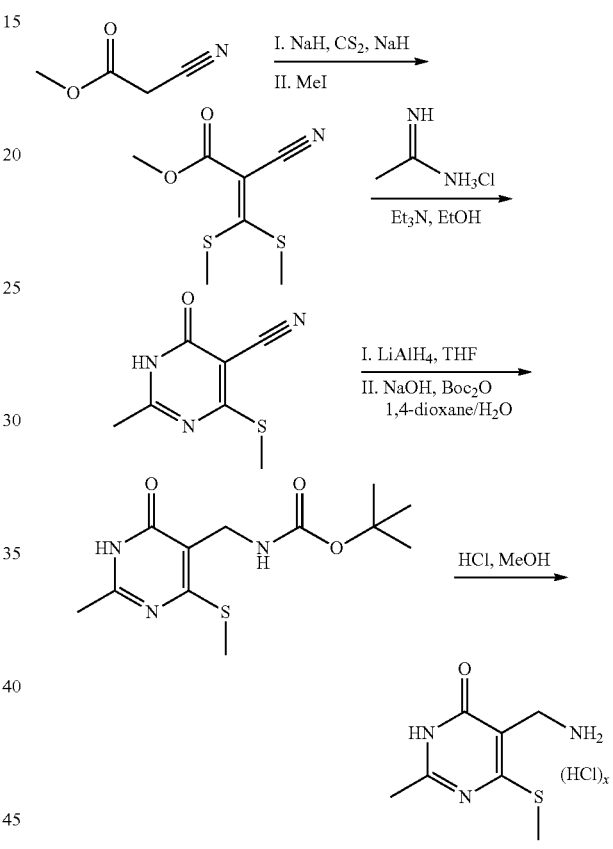

Intermediate 2

Step 1: Synthesis of methyl 2-cyano-3,3-bis(methylthio)acrylate

A suspension of sodium hydride (60% dispersion in mineral oil) (4.23 g, 106 mmol) in tetrahydrofuran (400 mL) was cooled to 0° C. before methyl cyanoacetate (8.90 mL, 101 mmol) was added dropwise. The reaction mixture was stirred vigorously for 15 minutes before carbon disulfide (6.1 mL, 101 mmol) was added dropwise while keeping the reaction temperature below 20° C. (the white semi-solid turned yellow). Next iodomethane (15.7 mL, 252 mmol) was added dropwise and the reaction mixture was stirred at room temperature for 15 minutes. The reaction was then concentrated under reduced pressure and the residue poured into ice water. The resulting precipitate was filtered and dried under vacuum to give the title compound (11.9 g, 58% yield) as a yellow/brown solid, which was used in the next step without further purification. $^1$H NMR (400 MHz, Chloroform-d) δ 3.83 (s, 3H), 2.76 (s, 3H), 2.61 (s, 3H).

Step 2: Synthesis of 2-methyl-4-(methylthio)-6-oxo-1,6-dihydropyrimidine-5-carbonitrile Methyl 2-cyano-3,3-bis(methylthio)acrylate (11.9 g, 58.5 mmol) was dissolved in ethanol (1000 mL). Acetamidine hydrochloride (5.53 g, 58.5 mmol) and triethylamine (36.7 mL, 263 mmol) were added to the mixture and stirred at reflux overnight. Then the reaction was concentrated under reduced pressure and the residue washed with 10% hydrochloric acid. The precipitate was filtered, and the filter cake was washed with water and diethyl ether before being dried under vacuum to give the title compound (5g, 47% yield) as a solid, which was used in the next step without further purification. LCMS [M+H]$^+$ m/z: calc'd 182.03; found 182.10. $^1$H NMR (400 MHz, Dimethylsulfoxide-d$_6$) δ 2.57 (s, 3H), 2.37 (s, 3H).

Step 3: Synthesis of tert-butyl ((2-methyl-4-(methylthio)-6-oxo-1,6-dihydropyrimidin-5-yl)methyl)carbamate To a suspension of 2-methyl-4-(methylthio)-6-oxo-1,6-dihydropyrimidine-5-carbonitrile (1.5 g, 8.27 mmol) in tetrahydrofuran (50 mL) at 0° C. was added a solution of lithium aluminum hydride in tetrahydrofuran (2 M, 6.2 mL, 12.4 mmol). The reaction was slowly warmed to room temperature and once completed quenched with an aqueous solution of sodium hydroxide (1 M, 33 mL, 33.1 mmol). To this mixture were sequentially added 1,4-dioxane (50 mL) and di-tert-butyldicarbonate (3.61 g, 16.6 mmol). The biphasic mixture was stirred vigorously until complete protection of the amine. The biphasic mixture was acidified to neutral pH with acetic acid, separated and the aqueous layer was extracted with dichloromethane. The combined organic layers were dried over magnesium sulfate, filtered and concentrated to dryness under reduced pressure. The residue was triturated with dichloromethane and the filtrate (containing the desired product) concentrated to dryness under reduced pressure. The resulting solid was purified by reverse phase flash chromatography (C18 column, gradient 5% to 95% acetonitrile in water buffered with 0.1% trifluoroacetic acid) then by normal phase flash chromatography (silica gel, gradient 30% to 90% ethyl acetate in dichloromethane) to give the title compound (2.57g, 26% yield, >99% purity) as a white solid. LCMS [M-(C$_4$H$_8$)+H]$^+$ m/z: calc'd 230.1; found 230.0. $^1$H NMR (400 MHz, Chloroform-d) δ 13.20 (s, 1H), 5.37 (t, J=5.5 Hz, 1H), 4.26 (d, J=5.6 Hz, 2H), 2.51 (s, 3H), 2.44 (s, 3H), 1.44 (s, 9H).

Step 4. Synthesis of 5-(aminomethyl)-2-methyl-6-(methylthio)pyrimidin-4(3H)-one (hydrochloride salt)

To a suspension of tert-butyl ((2-methyl-4-(methylthio)-6-oxo-1,6-dihydropyrimidin-5-yl)methyl)carbamate (300 mg, 1.05 mmol) in 1,4-dioxane (7.2 mL) at 23° C. was added a solution of hydrogen chloride in 1,4-dioxane (4 M, 2.10 mL, 8.40 mmol). The reaction as stirred at 23° C. for 3 h, then more of the solution of hydrogen chloride in 1,4-dioxane (4 M, 2.10 mL, 8.40 mmol) was added. After 14 h, the reaction was then concentrated to dryness under reduced pressure to give the title compound (254 mg, 94% yield) as a white solid, which was used in the next step without further purification. LCMS [M+Na]$^+$ (free base) m/z: calc'd 208.1; found 208.1.

Intermediate 3: 3-(aminomethyl)-6-chloro-4-(methylthio)pyridin-2(1H)-one (hydrochloride salt)

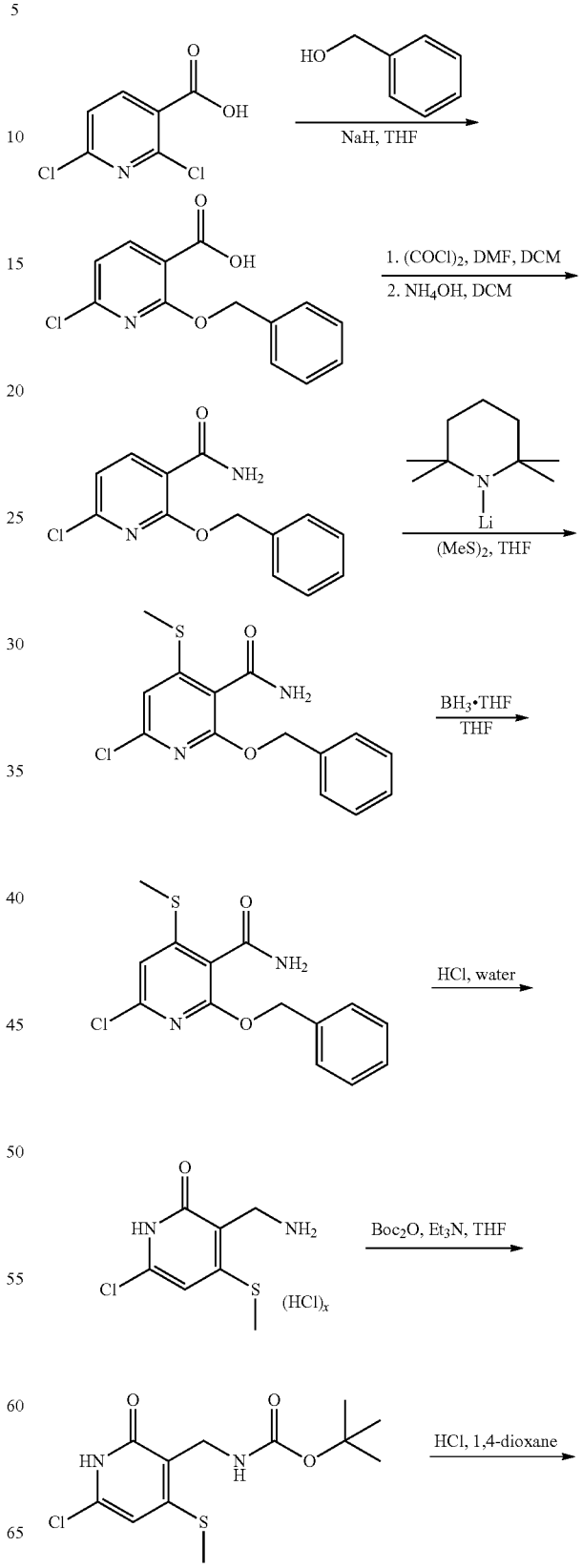

-continued

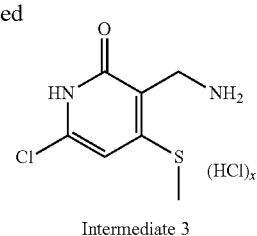

Intermediate 3

Step 1: Synthesis of 2-(benzyloxy)-6-chloronicotinic acid

To a suspension of sodium hydride (60% dispersion in mineral oil) (11.5 g, 286 mmol) in tetrahydrofuran (500 mL) was added benzyl alcohol (14 mL, 143 mmol) at 0° C. The reaction mixture was stirred for 20 min then a solution of 2,6-dichloropyridine-3-carboxylic acid (25 g, 130 mmol) in tetrahydrofuran (500 mL) was added and the reaction mixture was stirred for 4 hours at 23° C. The reaction was then quenched with 10% hydrochloric acid (300 mL), treated with a solid NaHCO$_3$ until pH ~8, acidified with acetic acid (50% in water), and finally extracted with ethyl acetate (200 mL×3). The combined organic layers were washed with brine (200 mL), dried over magnesium sulfate, filtered, and concentrated to dryness. The residue was purified by flash chromatography (silica gel, gradient 5% to 50% ethyl acetate in dichloromethane) to give the title compound (33.68 g, 98% yield).

Step 2: Synthesis of 2-(benzyloxy)-6-chloronicotinamide

To a solution of 2-(benzyloxy)-6-chloronicotinic acid (33.68 g, 128.2 mmol) in dichloromethane (500 mL) at 0° C. was added N,N-dimethylformamide (1 mL) followed by oxalyl chloride (11.9 mL, 141 mmol). The reaction was stirred at 23° C. for 2 hours then concentrated to dryness. The residue was dissolved in dichloromethane (200 mL) and slowly added to a concentrated solution of ammonium hydroxide (50 mL) at 0° C. After 1 h, the organic layer was collected and the aqueous phase extracted with dichloromethane (50 mL×3). The combined organic layers were dried over magnesium sulfate, filtered, and concentrated to dryness under reduced pressure. The residue was purified by flash chromatography (silica gel, gradient 0% to 50% ethyl acetate in dichloromethane) to give the title compound as a solid (quantitative yield).

Step 3: Synthesis of 2-(benzyloxy)-6-chloro-4-(methylthio)nicotinamide

To a solution of 2,2,6,6-tetramethylpiperidine (29.45 mL, 175.1 mmol) in tetrahydrofuran (300 mL) at −78° C. was added a solution of n-butyllithium in hexane (2.5 M, 70 mL, 175.1 mmol). The reaction mixture was warmed to 0° C. for 30 min, then cooled back to −78° C. A solution of 2-(benzyloxy)-6-chloronicotinamide (11.5 g, 43.8 mmol) in tetrahydrofuran (100 mL) was then added while keeping the internal temperature below −60° C. The reaction mixture was stirred for 1 h at −78° C. then dimethyldisulfide (15.77 mL, 175.1 mmol) was added. The reaction was stirred at −78° C. for an extra 2 h, then quenched at −78° C. with a solution of acetic acid in water (50% v/v). The desired product was extracted with ethyl acetate (100 mL×3) and the combined organic layers were washed with water (20 mL), a saturated aqueous sodium bicarbonate solution (20 mL), brine (20 mL), dried over magnesium sulfate, filtered and concentrated to dryness under reduced pressure. The residue was purified by flash chromatography (silica gel, gradient 0% to 20% ethyl acetate in dichloromethane) to afford the title compound (4.86 g, 36% yield).

Step 4: Synthesis of (2-(benzyloxy)-6-chloro-4-(methylthio)pyridin-3-yl)methanamine To a solution of 2-(benzyloxy)-6-chloro-4-(methylthio) nicotinamide (4.86 g, 15.7 mmol) in tetrahydrofuran (100 mL) at 23° C. was added a solution of borane in tetrahydrofuran (1 M, 63 mL, 63 mmol). The reaction mixture was stirred at reflux for 15 h then quenched by slow addition of methanol at room temperature. The reaction mixture was concentrated to dryness under reduced pressure and the residue purified by flash chromatography (silica gel, gradient 0% to 30% methanol in dichloromethane) to give the title compound (710 mg, 15% yield) as a white solid.

Step 5: Synthesis of 3-(aminomethyl)-6-chloro-4-(methylthio)pyridin-2(1H)-one (hydrochloride salt)

To a flask containing (2-(benzyloxy)-6-chloro-4-(methylthio)pyridin-3-yl)methanamine (710 mg, 2.41 mmol) was added concentrated hydrochloric acid (12 M, 5.0 mL, 60 mmol). The reaction mixture was stirred at 23° C. for 2 h then concentrated to dryness under reduced pressure. The residue was recrystalized from a mixture of methanol and diethyl ether to give the title compound (400 mg, 69% yield) as a white solid.

Step 6: Synthesis of tert-butyl ((6-chloro-4-(methylthio)-2-oxo-1,2-dihydropyridin-3-yl)methyl)carbamate To a suspension of 3-(aminomethyl)-6-chloro-4-(methylthio)pyridin-2(1H)-one hydrochloride salt (1.575 g, 6.53 mmol) in dichloromethane (50 mL) was added di-tert-butyldicarbonate (2.85 g, 13.1 mmol) followed by N,N-diisopropylethylamine (3.4 mL, 19.6 mmol) at room temperature. The reaction was stirred at room temperature for 3 h (until everything was dissolved) then quenched with water. The organic layer was separated, dried over magnesium sulfate, filtered, and concentrated to dryness under reduced pressure. The residue was purified by flash chromatography (silica gel, gradient 0 to 10% methanol in dichloromethane) to give the title compound as a white solid (1.5 g, 75% yield). LCMS [M+H]$^+$ m/z: calc'd 305.1; found 305.1.

Step 7: Synthesis of 3-(aminomethyl)-6-chloro-4-(methylthio)pyridin-2(1H)-one (hydrochloride salt)

To a suspension of tert-butyl ((6-chloro-4-(methylthio)-2-oxo-1,2-dihydropyridin-3-yl)methyl)carbamate (300 mg, 984 μmol) in 1,4-dioxane (4.9 mL) was added a solution of hydrogen chloride in 1,4-dioxane (4 M, 1.96 mL, 7.87 mmol) at room temperature. The reaction as stirred at room temperature for 3 h, then more of the solution of hydrogen chloride in 1,4-dioxane (4 M, 1.96 mL, 7.87 mmol) was added. After 14 h, the reaction was concentrated to dryness under reduced pressure to give the title compound (253 mg, quantitative yield) as a white solid, which was used in the next step without further purification. LCMS [M+Na]$^+$ (free base) m/z: calc'd 227.0; found 227.0.

Intermediate 4: methyl 7-chloro-2,4-dimethyl-2-(4-oxocyclohexyl)benzo[d][1,3]dioxole-5-carboxylate

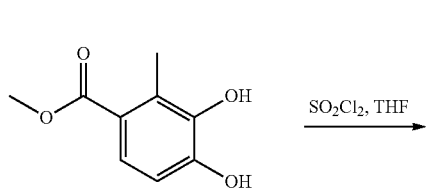

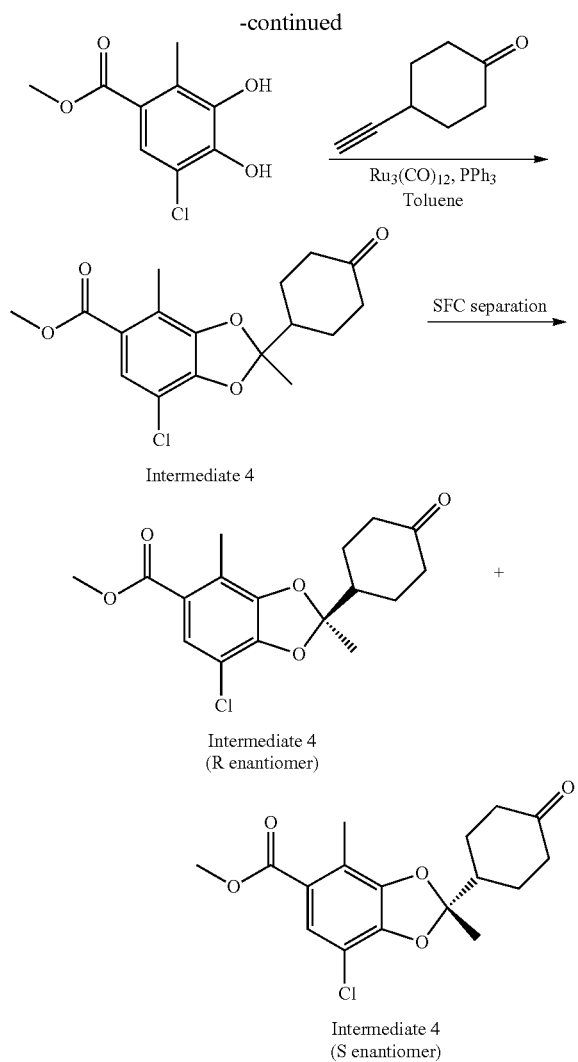

Intermediate 4

Intermediate 4 (R enantiomer)

Intermediate 4 (S enantiomer)

Step 1: Synthesis of methyl 5-chloro-3,4-dihydroxy-2-methylbenzoate

To a solution of methyl 3,4-dihydroxy-2-methylbenzoate (5.11 g, 27.9 mmol) in tetrahydrofuran (199 mL) at −20° C. was added sulfuryl chloride (2.45 mL, 30.6 mmol) dropwise. The reaction mixture was stirred at −20° C. for 3 h then quenched with a saturated aqueous solution of ammonium chloride (50 mL). The desired product was extracted with ethyl acetate (25 mL×3). The combined organic layers were washed with brine (25 mL), dried over sodium sulfate, filtered, and concentrated to dryness under reduced pressure. The residue was purified by flash chromatography (silica gel, gradient 0% to 60% ethyl acetate in heptane) to give the title compound (4.117 g, 68% yield) as a beige solid. LCMS [M+H]+ m/z: calc'd 217.0; found 217.1 (Cl isotope pattern).

Step 2: Synthesis of methyl 7-chloro-2,4-dimethyl-2-(4-oxocyclohexyl)-2H-1,3-benzodioxole-5-carboxylate A mixture of methyl 5-chloro-3,4-dihydroxy-2-methylbenzoate (1.2 g, 5.53 mmol), triruthenium dodecacarbonyl (176 mg, 276 µmol), and triphenylphosphine (145 mg, 553 µmol) was degassed under vacuum and purged with nitrogen (3 cycles). Toluene (8.1 mL) was added and the reaction mixture was heated to reflux for 30 min. A solution of 4-ethynylcyclohexan-1-one (1.34 g, 11.0 mmol) in toluene (17 mL) was then added dropwise and the reaction stirred for 23 h at reflux. Finally, the reaction mixture was cooled to room temperature and concentrated to dryness under reduced pressure. The residue was purified by flash chromatography (silica gel, gradient 0 to 60% ethyl acetate in heptane) to give the title compound (1.327 g, 70% yield) as a yellow oil. LCMS [M+Na]+ m/z: calc'd 361.1; found 361.1 (Cl isotope pattern).

Step 3: Separation of methyl (R)-7-chloro-2,4-dimethyl-2-(4-oxocyclohexyl)benzo[d][1,3]dioxole-5-carboxylate and methyl (S)-7-chloro-2,4-dimethyl-2-(4-oxocyclohexyl)benzo[d][1,3]dioxole-5-carboxylate The racemic mixture of methyl-7-chloro-2,4-dimethyl-2-(4-oxocyclohexyl)benzo[d][1,3]dioxole-5-carboxylate (4.4 g, 13 mmol) was resolved by preparative SFC [Column: ChiralPak AY from Daicel chemical industries (250 mm×50 mm I.D., 10 µm). Mobile phase A: CO$_2$/Mobile phase B: 0.1% NH$_4$OH in methanol. Isocratic (85% mobile phase A and 15% mobile phase B). Flow rate: 80 mL/min. Column temperature: 40° C]. Intermediate 4 (Peak 1) (undesired enantiomer/distomer): Retention time=6.2 min. Recovery=1.4 g, 4.05 mmol, 31% yield, 90% ee, 98% purity (yellow solid). $^1$H NMR (400 MHz, Chloroform-d) δ 7.48 (s, 1H), 3.78 (s, 3H), 2.44-2.36 (m, 2H), 2.35-2.25 (m, 6H), 2.19 (tdd, J=2.8, 5.6, 13.1 Hz, 2H), 1.70-1.57 (m, 5H). Intermediate 4 (Peak 2) (desired enantiomer/eutomer): Retention time=7.0 min. Recovery=1.1 g, 3.08 mmol, 23.75% yield, 99% ee, 95% purity (yellow solid). $^1$H NMR (400 MHz, Chloroform-d) δ 7.49 (s, 1H), 3.78 (s, 3H), 2.44-2.36 (m, 2H), 2.36-2.25 (m, 6H), 2.20 (tdd, J=2.8, 5.6, 13.1 Hz, 2H), 1.72-1.59 (m, 5H). SFC analytical method: [Column: ChiralPak AY-3 (150×4.6 mm I.D., 3 µm). Mobile phase A: CO$_2$/Mobile phase B: 0.05% Et$_2$NH in iPrOH. Gradient: from 5 to 40% of mobile phase B (over 5.5 min). Flow rate: 2.5 mL/min. Column temperature: 40° C.]. Intermediate 4 (Peak 1—undesired enantiomer/ distomer): Retention time=2.853 min. Intermediate 4 (Peak 2—desired enantiomer/eutomer): Retention time=2.979 min.

Intermediate 5: methyl 7-chloro-2,4-dimethyl-2-(trans-4-((3-(trifluoromethyl)oxetan-3-yl)amino)cyclohexyl)benzo[d][1,3]dioxole-5-carboxylate

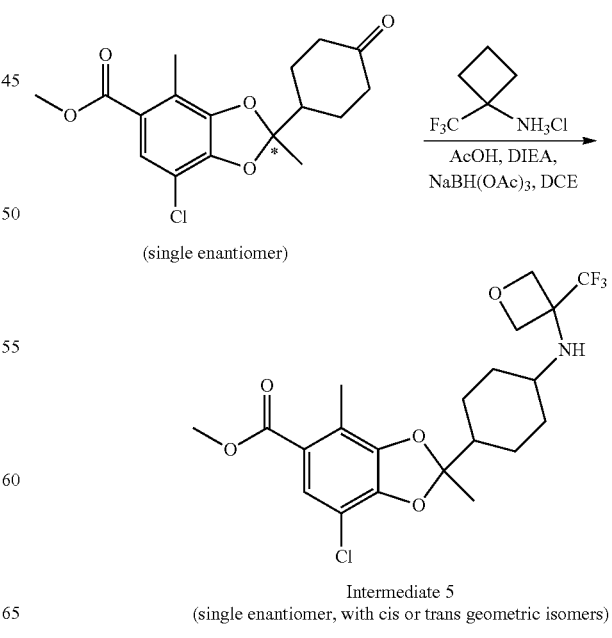

Intermediate 5 (single enantiomer, with cis or trans geometric isomers)

A mixture of 1-chloro-N-[3-(trifluoromethyl)oxetan-3-yl] hydrogenamine (678 mg, 3.82 mmol) and N,N-diisopropylethylamine (698 μL, 4.01 mmol) in dichloroethane (9.54 mL) was stirred at room temperature for 30 min before acetic acid (218 μL, 3.82 mmol) followed by methyl-7-chloro-2,4-dimethyl-2-(4-oxocyclohexyl)benzo[d][1,3]dioxole-5-carboxylate (650 mg, 1.91 mmol) were added to this reaction mixture. After 5 min at room temperature the mixture turned clear (yellow/brown) and sodium triacetoxyborohydride (404 mg, 1.91 mmol) was added. The reaction was stirred for 3 h at room temperature then quenched with a saturated aqueous solution of sodium bicarbonate (30 mL). The desired product was extracted with dichloromethane (30 mL×3) and the combined organic layers dried over sodium sulfate, filtered and concentrated to dryness under reduced pressure. The residue was purified by reverse phase flash chromatography (C18 column, acetonitrile/water 1:1 with 0.1% trifluoroacetic acid) to give two geometric isomers (cis and trans). The first eluting peak corresponds to the Geometric isomer 1.

Analytical LCMS Method (for Geometric Isomers)

[Column: Zorbax SB-C8 (75×4.6 mm I.D., 3.5 μm). Mobile phase A: 0.1% trifluoroacetic acid in acetonitrile/Mobile phase B: trifluoroacetic acid in water. Gradient: from 5 to 100% of mobile phase B (over 3.0 min) followed by 100% of mobile phase B (4.5 min). Flow rate: 1.5 mL/min. Column temperature: 20° C.] Geometric isomer 1 (desired): Retention time=4.073 min (278 mg, 31%). Geometric isomer 2 (undesired): Retention time=4.277 min (253 mg 29%).

Enantiomers of the Geometric isomer 1 (desired based on LCMS method) were separated by preparative SFC [Column: Chiralcel OX-H (250×21 mm I.D.). Mobile phase A: CO$_2$/Mobile phase B: 0.25% isopropylamine in a 1:1 isopropanol/Hexane mixture. Isocratic (85% mobile phase A and 15% mobile phase B). Flow rate: 80 g/min. Column temperature: 25° C.]. Intermediate 5 (Peak 1): Retention time=1.84 min. LCMS [M+H]$^+$ m/z: calc'd 464.15; found 464. Intermediate 5 (Peak 2): Retention time=2.1 min. LCMS [M+H]$^+$ m/z: calc'd 464.15; found 464.2.

Intermediate 6: 3-(aminomethyl)-4-chloro-6-methylpyridin-2(1H)-one

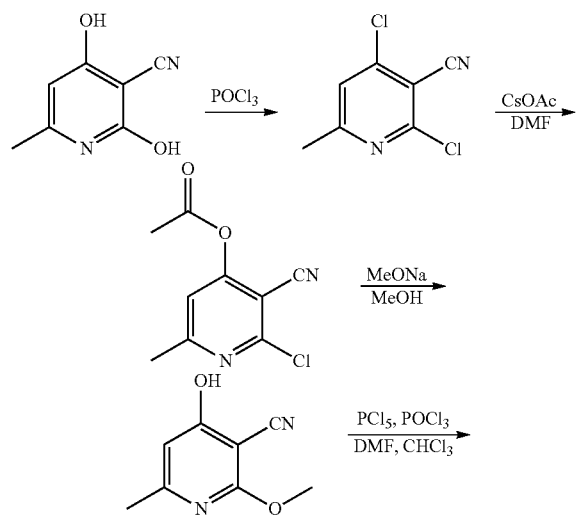

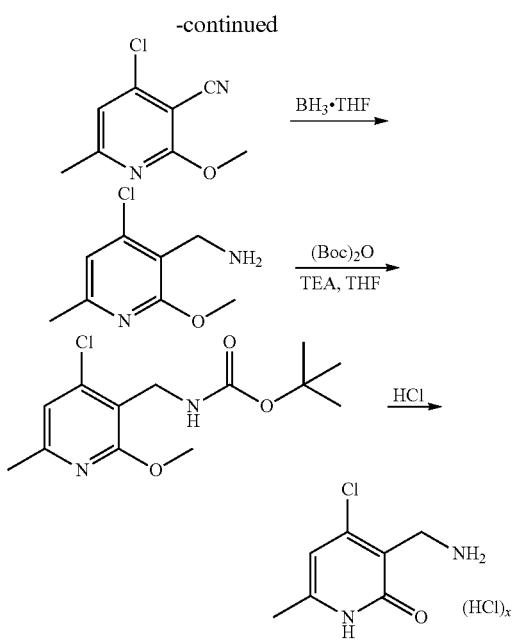

Step 1: Synthesis of 2,4-dichloro-6-methylnicotinonitrile

A solution of 2,4-dihydroxy-6-methylnicotinonitrile (80 g, 533.3 mmol) in phosphorus oxychloride (150 mL) was stirred at 120° C. for 2 h then quenched with an aqueous saturated sodium bicarbonate solution (until pH=8). It was partitioned between water (2000 mL) and ethyl acetate (1000 mL), the organic layer was dried over sodium sulfate, filtered and concentrated to dryness under reduced pressure to give the title compound (85 g, 86% yield) as a brown solid, which was used in the next step without further purification. LCMS [M+H]$^+$ m/z: calc'd 186.98; found 186.6.

Step 2: Synthesis of 2-chloro-4-hydroxy-6-methylnicotinonitrile

To a solution of 2,4-dichloro-6-methylnicotinonitrile (10 g, 53 mmol) in N,N-dimethylformamide (50 mL) was added cesium acetate (30.8 g, 160 mmol) at room temperature. The reaction was stirred at 80° C. overnight then quenched with water (800 mL). The desired product was extracted with ethyl acetate (800 mL) and the organic layer was dried over sodium sulfate, filtered and concentrated to dryness under reduced pressure. The title compound (8.8 g, 98% yield) was obtained as a brown solid and used in the next step without further purification. LCMS [M+H]$^+$ m/z: calc'd 169.01; found 168.8.

Step 3: Synthesis of 4-hydroxy-2-methoxy-6-methylnicotinonitrile

A mixture of 2-chloro-4-hydroxy-6-methylnicotinonitrile (8.8 g, 52.2 mmol) and sodium methoxide (14.1 g, 261 mmol) in methanol (50 mL) was stirred at 60° C. overnight. The mixture was quenched with a 1 M solution of hydrochloric aciduntil pH=5. It was partitioned between water (500 mL) and ethyl acetate (500 mL), the organic layer was dried over sodium sulfate and concentrated to give the title compound (8.0 g, 93% yield) as a brown solid, which was used in the next step without further purification. LCMS [M+H]$^+$ m/z: calc'd 165.1; found 164.8.

Step 4: 4-chloro-2-methoxy-6-methylnicotinonitrile

A mixture of 4-hydroxy-2-methoxy-6-methylnicotinonitrile (8.0 g, 48.7 mmol), phosphorus pentachloride (20.3 g, 97.5 mmol), phosphorus oxychloride (14.9 g, 9.09 mL, 97.5 mmol) and N,N-dimethylformamide (5 mL) in chloroform (100 mL) was stirred at 60° C. for 30 min. The reaction was quenched with saturated aqueous sodium bicarbonate solution (until pH=8). It was partitioned between water (1000 mL) and ethyl acetate (1000 mL), the organic layer was dried over sodium sulfate and concentrated to dryness to give the title compound (8.0 g, 90% yield) as a brown solid, which was used in next step directly without further purification. LCMS [M+H]+ m/z: calc'd 183.0; found 182.8.

Step 5: Synthesis of (4-chloro-2-methoxy-6-methylpyriin-3-yl)methanamine

To a solution of 4-chloro-2-methoxy-6-methylnicotinonitrile (8.0 g, 43.8 mmol) in tetrahydrofuran (50 mL) was added borane dimethylsulfide complex (10 M, 5.3 mL, 53 mmol). The mixture was stirred at 60° C. for 2 h, then quenched with methanol (10 mL) at 0° C. The mixture was concentrated to dryness under reduced pressure to give the title (7.0 g, 93% yield) as a brown solid, which was used in next step directly without further purification. LCMS [M+H]+ m/z: calc'd 187.1; found 187.1.

Step 6: test-butyl ((4-chloro-2-methoxy-6-methylpyridin-3-yl)methyl)carbamate

A mixture of (4-chloro-2-methoxy-6-methylpyridin-3-yl)methanamine (7.0 g, 37.5 mmol), di-tert-butyl dicarbonate (15.2 g, 75.0 mmol) and triethylamine (11.4 g, 15.7 mL, 113 mmol) in tetrahydrofuran (50 mL) was stirred at 20° C. for 16 h then quenched with water (500 mL). The desired product was extracted with ethyl acetate (500 mL) and the organic layer was dried over sodium sulfate, filtered and concentrated to dryness under reduced pressure. The residue was purified by flash column (silica gel column, petroleum ether: ethyl acetate 40:1) to give the title compound (3.0 28% yield) as a colorless oil. LCMS [M+H]+ m/z: calc'd 287.1; found 286.9.

Step 7: 3-(aminomethyl-4-chloro-6-methylpyridin-2(1H)-one

To a solution of hydrogen chloride in water (4 M, 10 mL, 10 mmol) was added tert-butyl ((4-chloro-2-methoxy-6-methylpyridin-3-yl)methyl)carbamate (3.0 g, 10.5 mmol) at room temperature. The reaction was heated at 100° C. for 2 h, then concentrated to dryness under reduced pressure to give the title compound (1.7 g, 94% yield) as a yellow solid. LCMS [M+H]+ m/z: calc'd 173.04; found 173.1. 1H NMR (400 MHz, Methanol-d4): δ 6.38 (s, 1H), 4.15 (s, 2H), 2.32 (s, 3H).

Intermediate 7: methyl 7-chloro-2-(4-(3,3-difluoroazetidin-1-yl)cyclohexyl)-2,4-dimethylbenzo[d][1,3]dioxole-5-carboxylate

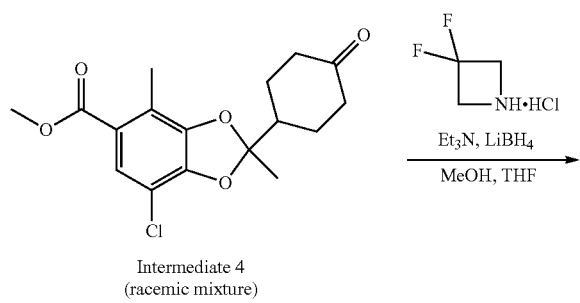

Intermediate 4
(racemic mixture)

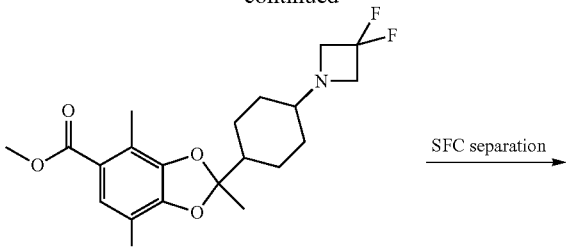

Intermediate 7
(single geometric isomers)

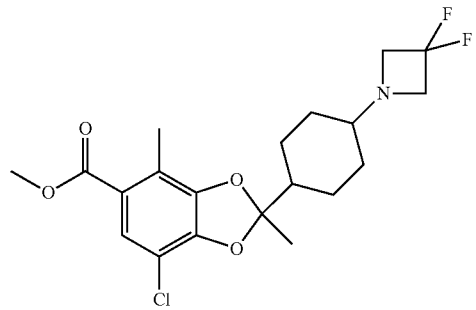

(single enantiomer; single geometric isomer 1 and isomer 2)

Step 1: Synthesis of methyl 7-chloro-2-(4-(3,3-difluoroazetidin-1-yl)cyclohexyl)-2,4-dimethylbenzo[d][1,3]dioxole-5-carboxylate A solution of methyl 7-chloro-2,4-dimethyl-2-(4-oxocyclohexyl)benzo[d][1,3]dioxole-5-carboxylate (Intermediate 4—racemic mixture) 550 mg, 1.62 mmol), 3,3-difluoroazetidine hydrochloride salt (839 mg, 6.48 mmol) and triethylamine (895 µL, 6.64 mmol) in methanol (5 mL) and tetrahydrofuran (5 mL) was stirred overnight at room temperature. Next day, the reaction was cooled down to −78° C. and a solution of lithium borohydride (2 M in tetrahydrofuran, 1.21 mL, 2.43 mmol) was added dropwise. The thick yellow mixture was gradually warmed to room temperature then quenched with a saturated aqueous solution of sodium carbonate at 0° C. The desired product was extracted with dichloromethane (thrice) and the combined organic layers were dried over sodium sulfate, filtered and concentrated to dryness under reduced pressure. The residue was purified twice by flash chromatography (silica gel KP-NH column, gradient 0 to 20% ethyl acetate in heptane) to give the title compound (354 mg, 53% yield) as a racemic mixture of a single geometric isomer (cis or trans). LCMS [M+H]+ m/z: calc'd 416.9; found 416.2.

Step 2: Separation of methyl (2R)-7-chloro-2-(4-(3,3-difluoroazetidin-1-yl)cyclohexyl)-2,4-dimethylbenzo[d][1,3]dioxole-5-carboxylate and methyl (2S)-7-chloro-2-(4-(3,3-difluoroazetidin-1-yl)cyclohexyl)-2,4-dimethylbenzo[d][1,3]dioxole-5-carboxylate The racemic mixture of methyl 7-chloro-2-(4-(3,3-difluomazetidin-1-yl)cyclohexyl)-2,4-dimethylbenzo[d][1,3]dioxole-5-carboxylate (560 mg) was resolved by preparative SFC [Column: Chiralpak AD-H from Daicel chemical industries. Mobile phase A: CO2/Mobile phase B: 0.25% isopropylamine in a mixture of hexane and ethanol (1:1). Isocratic (90% mobile phase A and 10% mobile phase B). Flow rate: 80g/min. Column temperature: 25° C.]. SFC analytical method: Column: Chiralpak AD-H from from Daicel chemical industries (100 mm×4.6 mm. Mobile phase A: CO2/Mobile phase B: 0.1% isopropylamine in a mixture of hexane and ethanol (3:1). Isocratic (85% mobile phase A and 15% mobile phase B). Flow rate: 4 mL/min. Column temperature: 40° C. Intermediate 7 (Peak 1): Retention time=1.02 min (SFC analytical method). Recovery=173 mg, 15% yield, 96% ee. $^1$H NMR (400 MHz, Chloroform-d) δ 7.48 (s, 1H), 3.78 (s, 3H), 2.44-2.36 (m, 2H), 2.35-2.25 (m, 6H), 2.19 (tdd, J=2.8, 5.6, 13.1 Hz, 2H), 1.70-1.57 (m, 5H). Intermediate 7 (Peak 2): Retention time=1.16 min (SFC analytical method). Recovery=150 mg, 13% yield, 97% ee. LCMS [M+H]$^+$ m/z: calc'd 416.86; found 416.2.

Intermediate 8: perfluorophenyl 7-chloro-2,4-dimethyl-2-(1-(2,2,2-trifluoroethyl)piperidin-4-yl)benzo[d][1,3]dioxole-5-carboxylate

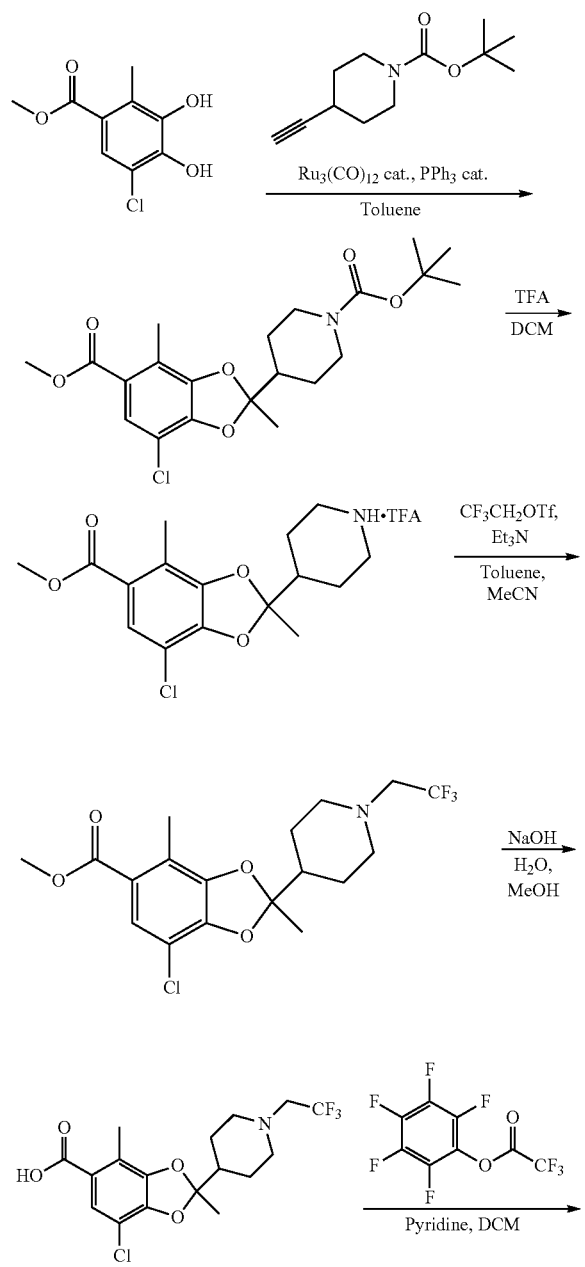

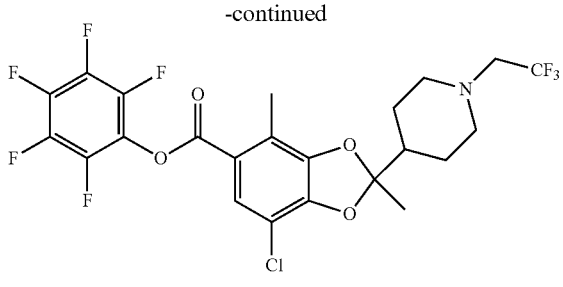

Intermediate 8
(racemic mixture)

Step 1: Synthesis of tert-butyl 4-(7-chloro-5-(methoxycarbonyl)-2,4-dimethylbenzo[d][1,3]dioxol-2-yl)piperidine-1-carboxylat In a 100 mL pear flask equipped with a condenser, a mixture of methyl 5-chloro-3,4-dihydroxy-2-methylbenzoate (1.219 g, 5.58 mmol), triphenylphosphine (146 mg, 0.558 mmol) and triruthenium dodecacarbonyl (178 mg, 0.279 mmol) was purged with nitrogen/vacuum cycles (4 cycles) then toluene (12 mL) was added, purged with nitrogen/vacuum cycles then stirred at 120° C. for 30 min. A mixture of tert-butyl 4-ethynylpiperidine-1-carboxylate (2.32 g, 11.1 mmol) in toluene (10 mL) was added to the dark mixture. The resulting orange solution was stirred for another 2 hours at 120° C. The reaction mixture was concentrated under reduced pressure then purified by flash chromatography (silica gel, gradient 0 to 100% ethyl acetate in heptane) to give the title compound (2.33 g, 98%) as a yellow oil. LCMS [M+Na]$^+$ m/z: calcd 448.2; found 448.2.

Step 2: Synthesis of methyl 7-chloro-2,4-dimethyl-2-(piperidin-4-yl)benzo[d][1,3]dioxole-5-carboxylate (trifluoroacetic acid salt)

To a yellow solution of tert-butyl 4-[7-chloro-5-(methoxycarbonyl)-2,4-dimethyl-2H-1,3-benzodioxol-2-yl]piperidine-1-carboxylate (2.33 g, 5.47 mmol) in dichloromethane (2 mL) was added TFA (1 mL). After 30 min, the reaction mixture was concentrated under reduced pressure to give the title compound (2.40 g, quant.) as a gum which was used in the next step without further purification. LCMS [M+H]$^+$ m/z: calc'd 326.79; found 326.2.

Step 3: Synthesis of methyl 7-chloro-2,4-dimethyl-2-(1-(2,2,2-trifluoroethyl)piperidin-4-yl)benzo[d][1,3]dioxole-5-carboxylate To a solution of methyl 7-chloro-2,4-dimethyl-2-(piperidin-4-yl)-2H-1,3-benzodioxole-5-carboxylate, trifluoroacetic acid salt (2.40 g, 5.45 mmol) in toluene (20 mL) and acetonitrile (10 mL) were added triethylamine (8 mL, 57.6 mmol) and 2,2,2-trifluoroethyl trifluoromethanesulfonate (3.0 g, 12.9 mmol). After 3 h, the reaction mixture was concentrated under reduced pressure. Water (50 mL) was added and the mixture was extracted with EtOAc (30 mL×3).The combined organic layers were washed with brine (50 mL×2), dried over sodium sulfate, filtered and concentrated under reduced pressure then purified by flash chromatography (silica gel, gradient 0 to 50% ethyl acetate in heptane) to give the title compound (2.04 g, 92%) as a yellowish oil. LCMS [M+H]$^+$ m/z: calc'd 408.81; found 408.2.

Step 4: Synthesis of 7-chloro-2,4-dimethyl-2-(1-(2,2,2-trifluoroethyl)piperidin-4-yl)benzo[d][1,3]dioxole-5-carboxylic acid To a solution of methyl 7-chloro-2,4-dimethyl-[(4-(2,2,2-trifluoroethyl)piperidin-4-yl]-2H-1,3-benzodioxole-5-carboxylate (691 mg, 1.69 mmol) in methanol (3 mL) was added 6 M sodium hydroxide in water (1 mL, 6.00 mmol) and heated at 60° C. After 25 min, the reaction mixture was concentrated under reduced pressure to remove most of the methanol. The mixture was then diluted with water, cooled to 0° C. then neutralized to pH=7 with 1 M hydrochloric acid. The mixture was extracted with dichloromethane (3 times) and the combined organic layers were dried over sodium sulfate, filtered, and concentrated under reduced pressure to give the title compound as a white solid which was used in the next step without further purification. LCMS [M+H]+ m/z: calc'd 394.79; found 394.2.

Step 5: Synthesis of perfluorophenyl 7-chloro-2,4-dimethyl-2-(1-(2,2,2-trifluoroethyl)piperidin-4-yl)benzo[d][1,3]dioxole-5-carboxylate To a stirred solution of 7-chloro-2,4-dimethyl-2-[1-(2,2,2-trifluoroethyl)piperidin-4-yl]-2H-1,3-benzodioxole-5-carboxylic acid (665 mg, 1.68 mmol) in dichloromethane (5 mL) was added pyridine (1 mL, 12.4 mmol) followed by addition of 2,3,4,5,6-pentafluorophenyl 2,2,2-trifluoroacetate (500 μL, 2.90 mmol). After 20 min, the reaction mixture was concentrated under reduced pressure to afford the title compound which was used in the next step without further purification. LCMS [M+H]+ m/z: calc'd 560.84; found 560.2.

Intermediate 9: 7-chloro-2-(4-(3-methoxyazetidin-1-yl)cyclohexyl)-2,4-dimethylbenzo[d][1,3]dioxole-5-carboxylic acid

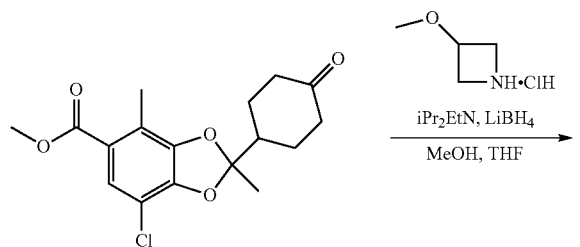

Intermediate 4
(Peak 2)

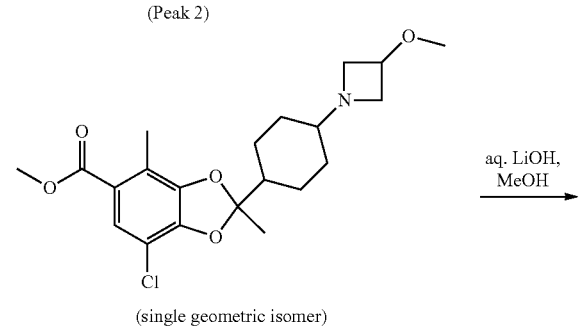

(single geometric isomer)

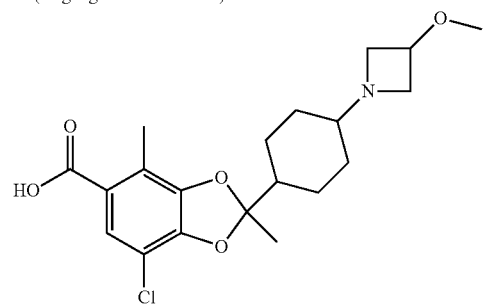

Intermediate 9
(single enantiomer; single geometric isomer)

Step 1: Synthesis of methyl 7-chloro-2-(4-(3-methoxyazetidin-1-yl)cyclohexyl)-2,4-dimethylbenzo[d][1,3]dioxole-5-carboxylate A solution of 3-methoxyazetidine hydrochloride salt (8 g, 64.75 mmol) and N,N-diisopropylethylamine (12 mL, 68.9 mmol) in methanol (30 mL) was stirred at room temperature for 30 min before a solution of another solution of methyl 7-chloro-2,4-dimethyl-2-(4-oxocyclohexyl)-1,3-benzodioxole-5-carboxylate (Intermediate 4—Peak 2) (4.1 g, 12.10 mmol) in tetrahydrofuran (30 mL) was added. The reaction mixture was stirred at room temperature for 1 h then cooled to −70° C. Lithium borohydride (500 mg, 22.96 mmol) was added and the reaction stirred at −70° C. for 30 min [or until complete consumption of the starting material was observed by TLC, ethyl acetate/methanol 5:1]. Next, two batches of the reaction were combined and quenched with a saturated aqueous solution of ammonium chloride (120 mL) at 0° C. and the desired product was extracted with dichloromethane (200 mL×3). The combined organic layers were dried over sodium sulfate, filtered and concentrated to dryness under reduced pressure. The residue was purified by flash chromatography (silica gel, gradient 0 to 14% methanol in dichloromethane) to give title compound (8.05 g, 67% yield, 83% purity) as a light yellow oil. A sample (50 mg) was purified further by preparative thin layer chromatography (silica gel, ethyl acetate:methanol 15:1). LCMS [M+H]+ m/z: calc'd. 410.2; found 410.1. $^1$H NMR (400 MHz, Methanol-$d_4$) δ 7.39 (s, 1H), 3.95-3.91 (m, 1H), 3.73 (s, 3H), 3.59-3.51 (m, 2H), 3.16 (s, 3H), 2.97 (br dd, J=6.4, 8.0 Hz, 2H), 2.26 (s, 3H), 2.11-2.02 (m, 1H), 1.91-1.73 (m, 5H), 1.54 (s, 3H), 1.22-1.12 (m, 2H), 0.98-0.86 (m, 2H).

Step 2: Synthesis of 7-chloro-2-(4-(3-methoxyazetidin-1-yl)cyclohexyl)-2,4-dimethylbenzo[d][1,3]dioxole-5-carboxylic acid To a solution of methyl 7-chloro-2-(4-(3-methoxyazetidin-1-yl)cyclohexyl)-2,4-dimethylbenzo[d][1,3]dioxole-5-carboxylate (4 g, 9.75 mmol) in methanol (48 mL) was added a solution of lithium hydroxide hydrate (4.03 g, 96.06 mmol) in water (12 mL). The reaction was stirred at 70° C. for 2 h then two batches were combined and concentrated under reduced pressure. Water (50 mL) was added and the pH adjusted to 6 with a saturated aqueous citric acid solution at 0° C. The desired product was extracted with a 3:1 mixture of dichloromethane and isopropanol (300 mL×5). The combined organic layers were dried over sodium sulfate, filtered and concentrated to dryness under reduced pressure to give the title compound (6.1 g, crude) as a off-white solid, which was used in the next step without further purification. LCMS [M+H]+ m/z: calc'd. 396.2; found 396.1. $^1$H NMR (400 MHz, Methanol-$d_4$) δ 7.07 (s, 1H), 4.05-4.10 (m, 2H), 3.76-3.88 (m, 1H), 3.67 (br dd, J=10, 3.6 Hz, 2H), 3.22 (s, 3H), 2.71-2.81 (m, 1H), 2.19 (s, 3H), 1.91-1.99 (m, 4H), 1.75-1.85 (m, 1H), 1.52 (s, 3H), 1.18-1.28 (m, 2H), 1.06-1.14 (m, 2H).

EXAMPLE #1

7-chloro-2-(4-(3-(difluoromethoxy)azetidin-1-yl)cyclohexyl)-2,4-dimethyl-N-((6-methyl-4-(methylthio)-2-oxo-1,2-dihydropyridin-3-yl)methyl)benzo[d][1,3]dioxole-5-carboxamide

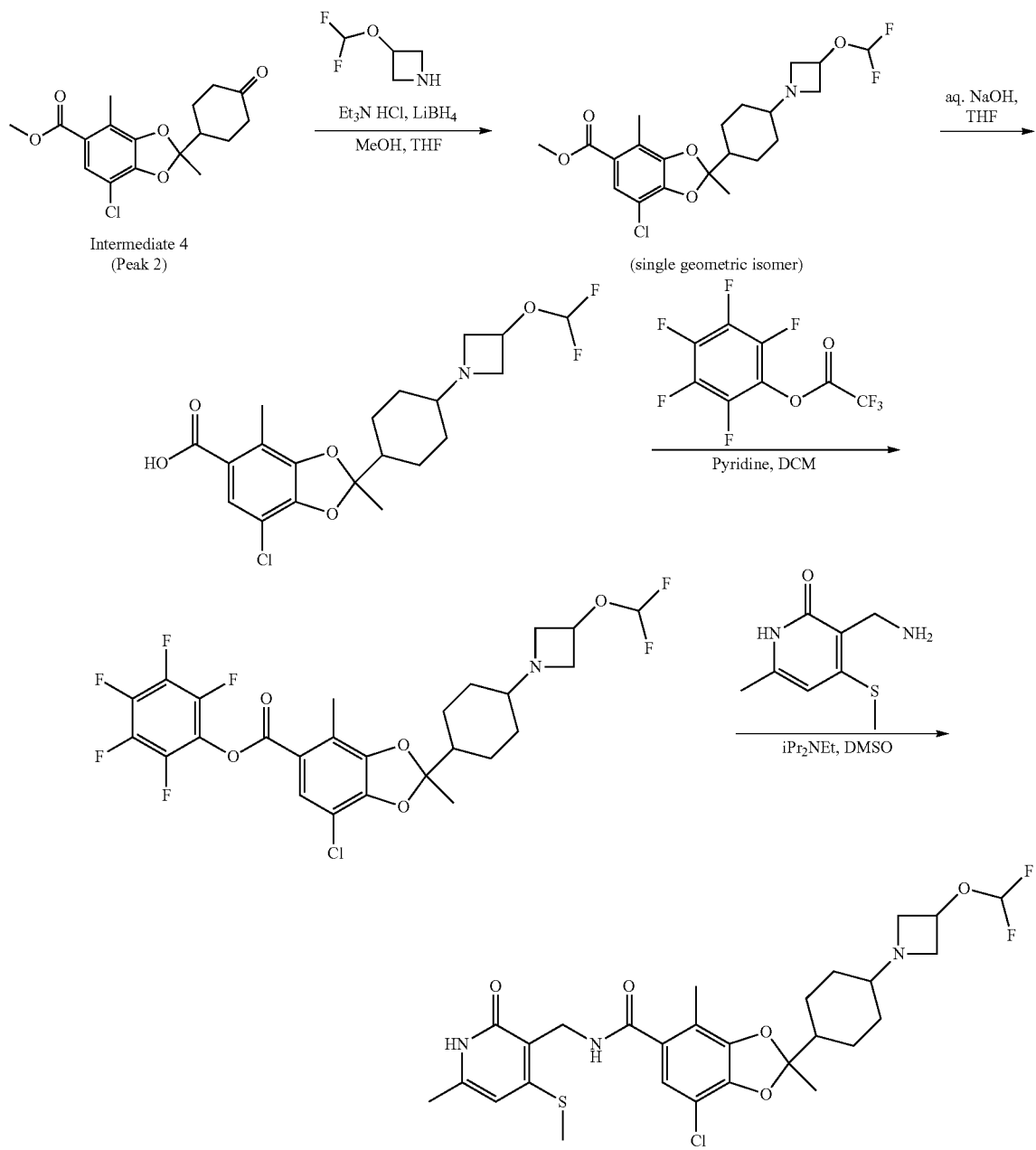

Example 1
(single enantiomer; single geometric isomer)

Step 1: Synthesis of methyl 7-chloro-2-(4-(3-(difluoromethoxy)azetidin-1-yl)cyclohexyl)-2,4-dimethylbenzo[d][1,3]dioxole-5-carboxylate A solution of methyl 7-chloro-2,4-dimethyl-2-(4-oxocyclohexyl)benzo[d][1,3]dioxole-5-carboxylate (Intermediate 4—Peak 2) (224 mg, 0.661 mmol), 3-(difluoromethoxy) azetidine (336 mg, 2.72 mmol) and triethylamine hydrochloride salt (373 mg, 2.71 mmol) in a mixture of methanol (2 mL) and tetrahydrofuran (2 mL) was stirred at room temperature for 1.5 h, then cooled to −78° C. A lithium borohydride solution in tetrahydrofuran (2 M, 500 μL, 1 mmol) was added dropwise at −78° C. before the reaction was allowed to warm to room temperature for 15 min. Next, the mixture was cooled to 0° C. then quenched with a saturated aqueous solution of sodium bicarbonate, diluted with dichloromethane and warmed to room temperature. The desired product was extracted from the aqueous layer with dichloromethane (thrice) and the combined organic layers dried using a hydrophobic filter and concentrated to dryness under reduced pressure. The residue was purified by flash chromatography (silica gel, gradient 10 to 100% ethyl acetate in heptane then 0 to 100% ethanol in ethyl acetate) to give a single geometric isomer (cis or trans) of the title compound (205 mg, 70% yield). LCMS [M+H]$^+$ m/z: calc'd 445.9; found 446.2.

Step 2: Synthesis of 7-chloro-2-(4-(3-(difluoromethoxy)azetidin-1-yl)cyclohexyl)-2,4-dimethylbenzo[d][1,3]dioxole-5-carboxylic acid To a solution of methyl 7-chloro-2-(4-(3-(difluoromethoxy)azetidin-1-yl)cyclohexyl)-2,4-dimethylbenzo[d][1,3]dioxole-5-carboxylate (205 mg, 0.460 mmol) in methanol (3 mL) was added a solution of sodium hydroxide in water (6 M, 1 mL, 6.00 mmol). The reaction was heated at 60° C. for 20 min, then diluted with water, cooled to 0° C., acidified to pH=2 with 1 M hydrochloric acid and then neutralized to pH=7 with a 1 M sodium hydroxide aqueous solution. The desired product was extracted with dichloromethane (thrice), dried using a hydrophobic filter and concentrated to dryness under reduced pressure to give the title compound (176 mg, 89% yield) as a white solid which was used in the next step without further purification. LCMS [M+H]$^+$ m/z: calc'd 431.9; found 432.2.

Step 3: Synthesis of perfluorophenyl 7-chloro-2-((1r,4R)-4-(3-(difluoromethoxy)azetidin-1-yl)cyclohexyl)-2,4-dimethylbenzo[d][1,3]dioxole-5-carboxylate To a solution of 7-chloro-2-(4-(3-(difluoromethoxy)azetidin-1-yl)cyclohexyl)-2,4-dimethylbenzo[d][1,3]dioxole-5-carboxylic acid (176 mg, 0.408 mmol) in dichloromethane (0.5 mL) was added pyridine (1.0 mL, 12.4 mmol) followed by the addition of 2,3,4,5,6-pentafluorophenyl 2,2,2-trifluoroacetate (150 μL, 0.871 mmol) at room temperature. After 20 min, the reaction mixture was concentrated to dryness under reduced pressure to give a mixture of the title compound (100% theoretical yield=243 mg) and by-products. The crude mixture was used in the next step without further purification. LCMS [M+H]$^+$ m/z: calc'd 597.91; found 598.2.

Step 4: Synthesis of 7-chloro-2-(4-(3-(difluoromethoxy)azetidin-1-yl)cyclohexyl)-2,4-dimethyl-N-((6-methyl-4-(methylthio)-2-oxo-1,2-dihydropyridin-3-yl)methyl)benzo[d][1,3]dioxole-5-carboxamide To a solution of perfluorophenyl 7-chloro-2-(4-(3-(difluoromethoxy)azetidin-1-yl)cyclohexyl)-2,4-dimethylbenzo[d][1,3]dioxole-5-carboxylate (≤243 mg, ≤0.406 mmol) in dimethylsulfoxide (1 mL) were added 3-(aminomethyl)-6-methyl-4-(methylthio)pyridin-2(1H)-one (hydrochloride salt) (Intermediate 1) (222 mg, 1.20 mmol) and N,N-diisopropylethylamine (0.30 mL, 1.71 mmol). The reaction mixture was stirred at 60° C. for 1 h, then concentrated to dryness under a strong flow of nitrogen overnight. The residue was purified twice by reverse phase flash chromatography (C18 column, gradient 0 to 100% acetonitrile in water with 0.1% of trifluoroacetic acid). The residue was diluted with dichloromethane and a saturated solution of sodium bicarbonate. The aqueous layer was washed with dichloromethane. The combined organic layers were dried over sodium sulfate and concentrated under reduced pressure to give the title compound (166 mg, 68% yield over two steps) as a single geometric isomer (cis or trans). LCMS [M+H]$^+$ m/z: calc'd 598.1; found 598.3. $^1$H NMR (400 MHz, Methanol-d$_4$) δ 6.88 (s, 1 H), 6.26 (s, 1 H), 6.38 (t, J=74.3 Hz, 2 H), 4.71 (quin, J=6.0 Hz, 1 H), 4.48 (s, 2 H), 3.69-3.60 (m, 2 H), 3.18-3.11 (m, 2 H), 2.52 (s, 3 H), 2.29 (s, 3 H), 2.18 (s, 3 H), 2.10 (tt, J=3.5, 11.2 Hz, 1 H), 1.98-1.86 (m, 4 H), 1.85-1.78 (m, 1 H), 1.60 (s, 3 H), 1.32-1.21 (m, 2 H), 1.06-0.92 (m, 2 H).

TABLE 1

The following compound was prepared in a similar manner as Example 1 using the appropriate starting material.

| Example | Structure | Analytical data |
| --- | --- | --- |
| 2 | 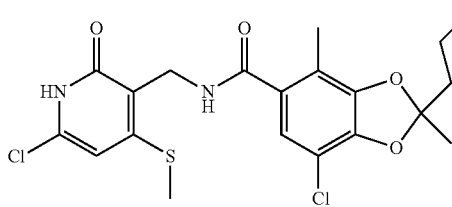 | LCMS [M + H]$^+$ m/z: calcd 618.1; found 618.1. $^1$H NMR (400 MHz, Chloroform-d) δ 6.91-6.88 (m, 1H), 6.58 (t, J = 5.4 Hz, 1H), 6.53 (s, 1H), 6.39-5.97 (m, 2H), 3.80 (d, J = 7.3 Hz, 2H), 3.14 (d, J = 6.4 Hz, 2H), 2.53-2.49 (m, 3H), 2.26 (s, 3H), 2.13 (br. s., 1H), 1.99-1.78 (m, 5H), 1.60 (s, 3H), 1.45 (d, J = 3.4 Hz, 1H), 1.28-1.18 (m, 2H), 1.15-1.01 (m, 2H). |

(single enantiomer; single geometric isomer)

Prepared from intermediate 3 and intermediate 4

(Peak 2)

EXAMPLE #3

(R)-7-chloro-N-((6-chloro-4-(methylthio)-2-oxo-1,2-dihydropyridin-3-yl)methyl)-2-(trans-4-(dimethylamino)cyclohexyl)-2,4-dimethylbenzo[d][1,3]dioxole-5-carboxamide

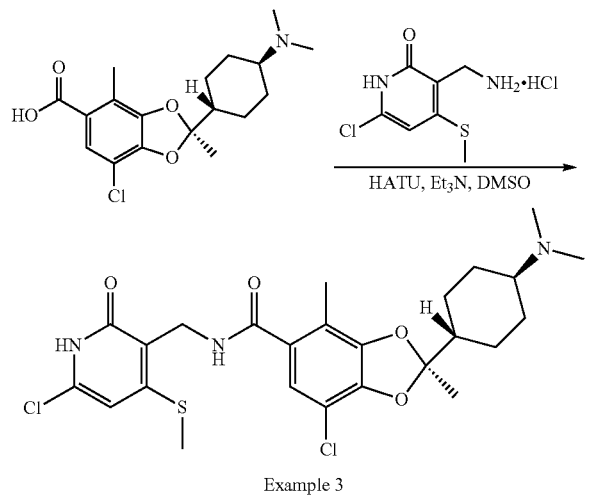

Example 3

To a solution of (R)-7-chloro-2-(trans-4-(dimethylamino)cyclohexyl)-2,4-dimethylbenzo[d][1,3]dioxole-5-carboxylic acid (prepared according to the procedure described in the patent application US2017/0073335 A1) (48 mg, 0.1356 mmol) in dimethylsulfoxide (0.5 mL) was added triethylamine (56.6 0.407 mmol) and O-(7-azabenzotriazol-1-yl)-N,N,N',N'-tetramethyluronium hexafluorophosphate (41.2 mg, 0.108 mmol) at room temperature. Since the formation of the activated ester was incomplete by LCMS ([M+H]+ m/z: 368.2) after 5 min, additional O-(7-azabenzotriazol-1-yl)-N,N,N',N'-tetramethyluronium hexafluorophosphate (16 mg, 0.042 mmol) in dimethylsulfoxide (1 mL) was added twice. After completing the activation of the acid, a suspension of 3-(aminomethyl)-6-chloro-4-(methylsulfanyl)-1,2-dihydropyridin-2-one hydrochloride salt (65.3 mg, 0.271 mmol) and triethylamine (56.6 µL, 0.407 mmol) in dimethylsulfoxide (0.5 mL) was added at room temperature. The reaction mixture was heated at 60° C. for 45 min, then diluted with dichloromethane and water. The organic layer was dried using a hydrophobic filter and concentrated to dryness under reduced pressure. The residue was purified by flash chromatography [silica gel KP-NH column, gradient 0 to 100% ethyl acetate in heptane, then 0 to 100% ethanol in dichloromethane, then 0 to 100% methanol (with 20% ammonium hydroxide) in ethyl acetate] to give the title compound (30 mg, 41% yield) as a white solid. LCMS [M+H]+ m/z: calc'd 540.5; found 540.2. $^1$H NMR (400 MHz, Methanol-$d_4$) δ 6.89 (s, 1H), 6.68 (s, 1H), 4.50 (s, 2H), 3.20 (tt, J=3.2, 11.9 Hz, 1H), 2.83 (s, 6H), 2.53 (s, 3H), 2.18 (s, 3H), 2.16-2.08 (m, 4H), 2.02-1.94 (m, 1H), 1.62 (s, 3H), 1.54 (dq, J=3.4, 12.4 Hz, 2H), 1.47-1.37 (m, 2H).

TABLE 2

The following compounds were prepared in a similar manner as Example 3 using the appropriate starting material.

| Example | Structure | Analytical data |
|---|---|---|
| 4 | (R enantiomer; trans geometric isomer)<br>Prepared from intermediate 1 | LCMS [M + H]+ m/z: calc'd 520.2; found 520.3. $^1$H NMR (400 MHz, Dimethylsulfoxide-$d_6$) δ 11.52 (br. s., 1H), 8.00 (t, J = 4.4 Hz, 1H), 6.85 (s, 1H), 6.08 (s, 1H), 4.27 (d, J = 4.4 Hz, 2H), 3.57 (s, 1H), 2.45 (s, 3H), 2.17 (s, 3H), 2.14 (s, 9H), 1.92-1.77 (m, 5H), 1.60 (s, 3H), 1.15 (t, J = 9.0 Hz, 4H) |
| 5 | (R enantiomer; trans geometric isomer)<br>Prepared from intermediate 2 | LCMS [M + H]+ m/z: calc'd 521.2; found 521.2. NMR (400 MHz, Dimethylsulfoxide-$d_6$) δ 12.60-12.19 (m, 2H), 8.05 (t, J = 4.4 Hz, 1H), 6.87 (s, 1H), 4.21 (d, J = 4.4 Hz, 2H), 2.47 (s, 3H), 2.29 (s, 2H), 2.19-2.12 (m, 9H), 2.09 (br. s., 1H), 1.94-1.76 (m, 5H), 1.60 (s, 3H), 1.15 (t, J = 9.6 Hz, 4H) |

EXAMPLE #6

(Enantiomer 1): 7-chloro-N-((6-chloro-4-(methylthio)-2-oxo-1,2-dihydropyridin-3-yl)methyl)-2-(4-(dimethylamino)cyclohexyl)-2,4-dimethylbenzo[d][1,3]dioxole-5-carboxamide

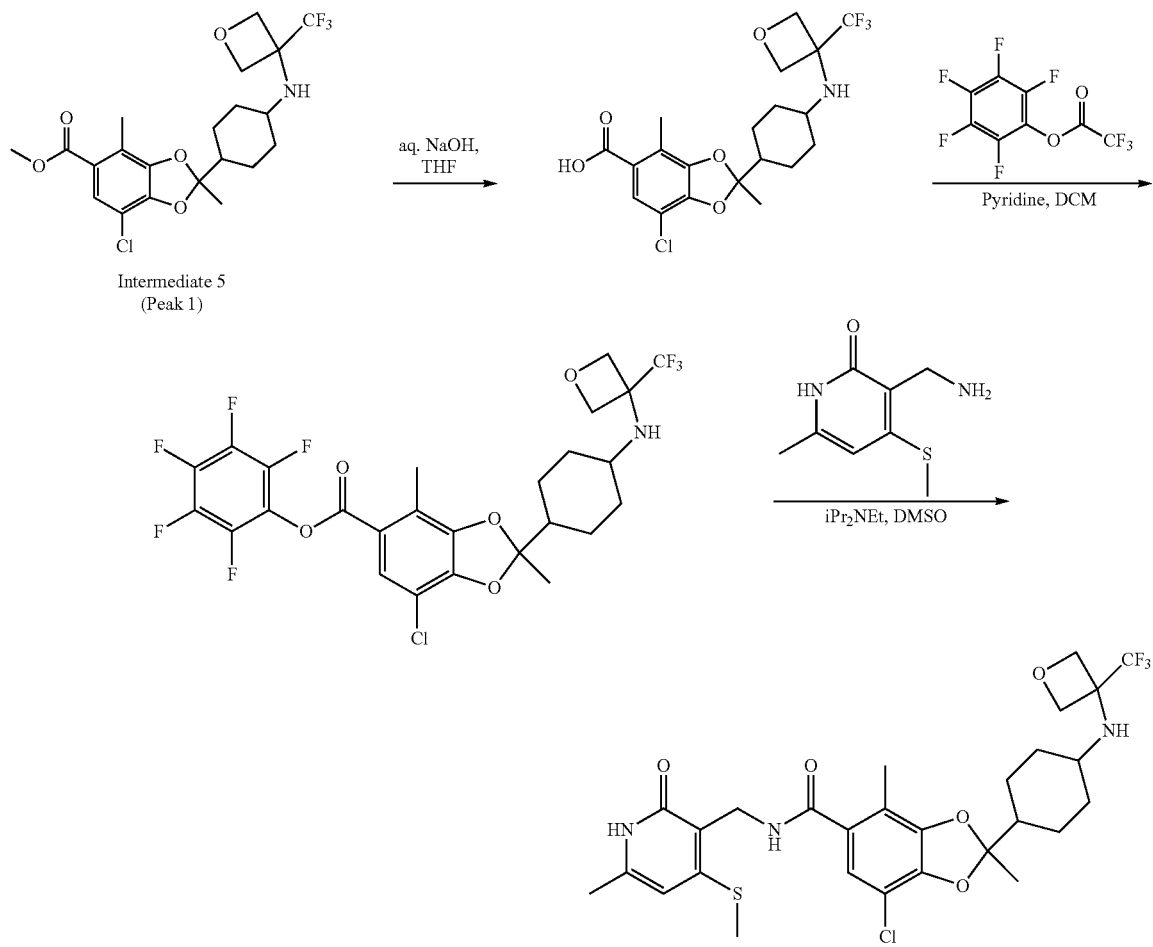

Example 6 (Enantiomer 1)
(Single enantiomer; single geometric isomer)

Step 1: Synthesis of 7-chloro-2,4-dimethyl-2-(4-((3-(trifluoromethyl)oxetan-3-yl)amino)cyclohexyl)benzo[d][1,3]dioxole-5-carboxylic acid To a solution of methyl 7-chloro-2,4-dimethyl-2-[4-{[3-(trifluoromethyl)oxetan-3-yl]amino}cyclohexyl]-2H-1,3-benzodioxole-5-carboxylate (Intermediate 5—Peak 1) (81 mg, 0.174 mmol) in methanol (1 mL) was added sodium hydroxide (72 mg, 1.79 mmol). The reaction mixture heated at 60° C. for 20 min, cooled to 0° C. and then acidified to pH=2 with 1 M hydrochloric acid. The desired product was then extracted with dichloromethane (thrice) and the combined organic layers dried using a hydrophobic filter. The filtrate was concentrated to dryness under reduced pressure to give the title compound (70 mg, 89% yield) as a white solid, which was used in the next step without further purification. LCMS [M+H]$^+$ m/z: calc'd 450.1; found 450.2.

Step 2: Synthesis of perfluorophenyl 7-chloro-2,4-dimethyl-2-(4-((3-(trifluoromethyl)oxetan-3-yl)amino)cyclohexyl)benzo[d][1,3]dioxole-5-carboxylate To a solution of 7-chloro-2,4-dimethyl-2-(4-((3-(trifluoromethyl)oxetan-3-yl)amino)cyclohexyl)benzo[d][1,3]dioxole-5-carboxylic acid (70 mg, 155 μmol) in dichloromethane (0.5 mL) was added pyridine (24.9 μL, 310 μmol) and 2,3,4,5,6-pentafluorophenyl 2,2,2-trifluoroacetate (39.8 μL, 232 μmol) at room temperature. After 15 min the reaction was concentrated under reduced pressure to give a mixture of the title compound and by-products (68 mg, crude). The crude mixture was used in the next step without further purification. LCMS [M+H]$^+$ m/z: calc'd 616.1; found 616.2.

Step 3: Synthesis of 7-chloro-2,4-dimethyl-N-((6-methyl-4-(methylthio)-2-oxo-1,2-dihydropyridin-3-yl)methyl)-2-(4-((3-(trifluoromethyl)oxetan-3-yl)amino)cyclohexyl)benzo[d][1,3]dioxole-5-carboxamide To a solution of 2,3,4,5,6-pentafluorophenyl 7-chloro-2,4-dimethyl-2-[4-{[3-(trifluoromethyl)oxetan-3-yl]amino}cyclohexyl]-2H-1,3-benzodioxole-5-carboxylate (≤68 mg, ≤110 μmol) in N,N-dimethylformamide (1 mL) was added 3-(aminomethyl)-6-methyl-4-(methylsulfanyl)-1,2-dihydropyridin-2-one (free base) (30.4 mg, 0.165 mmol) and N,N-diisopropylethylamine (0.1 mL, 574 μmol) at room temperature. The reaction was stirred at 50° C. for 30 min then directly added onto a C18 column for purification by reverse phase flash chromatography (C18 column, gradient 5 to 50% acetonitrile in water with 0.1% trifluoroacetic acid) to give the trifluoroacetic acid salt of the title compound. The salt was dissolved in dichloromethane and the organic layer washed with a saturated aqueous solution of sodium bicarbonate. Finally, the organic layer was concentrated to dryness under reduced pressure to give the title compound (free base) (42 mg, 62% yield) as a white solid. LCMS [M+H]+ m/z: calcd 616.19; found 616.3. ¹H NMR (400 MHz, Chloroform-d) δ 12.62-12.44 (m, 1H), 7.16 (t, J=5.1 Hz, 1H), 6.91 (s, 1H), 6.04 (s, 1H), 4.76 (s, 3H), 4.62-4.46 (m, 4H), 2.72-2.63 (m, 1H), 2.49 (s, 3H), 2.32 (s, 3H), 2.27 (s, 3H), 1.92 (d, J=5.9 Hz, 4H), 1.80 (br. s., 1H), 1.60 (s, 3H), 1.36-1.10 (m, 6H).

TABLE 3

The following compounds were prepared in a similar manner as Example 6 using the appropriate starting material.

| Example | Structure | Analytical data |
| --- | --- | --- |
| 6 (Enantiomer 2) | 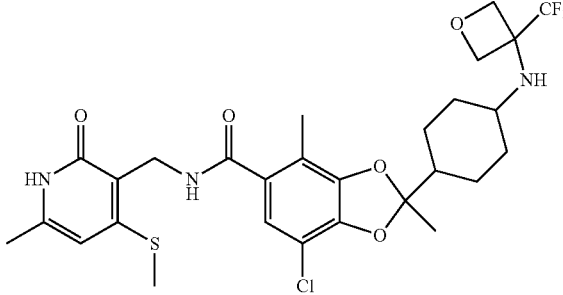<br>(single enantiomer; single geometric isomer)<br>Prepared from intermediate 1 and intermediate 5 (Peak 2) | LCMS [M + H]+ m/z: calc'd 616.19; found 616.3. ¹H NMR (400 MHz, Chloroform-d) δ 12.45-12.30 (m, 1H), 7.14 (t, J = 5.4 Hz, 1H), 6.91 (s, 1H), 6.04 (s, 1H), 4.75 (d, J = 7.3 Hz, 2H), 4.61 (s, 2H), 4.55-4.51 (m, 2H), 2.68 (t, J = 9.5 Hz, 1H), 2.49 (s, 3H), 2.32 (s, 3H), 2.27 (s, 3H), 1.92 (d, J = 6.4 Hz, 4H), 1.83 (t, J = 11.7 Hz, 1H), 1.61 (s, 3H), 1.35-1.12 (m, 6H). |
| 7 (Enantiomer 1) | 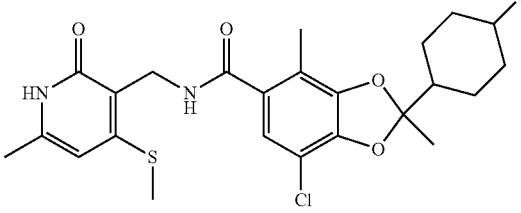<br>(single enantiomer; single geometric isomer)<br>Prepared from intermediate 1 and intermediate 7 (Peak 1) | LCMS [M + H]+ m/z: calc'd 568.2; found 568.3. ¹H NMR (400 MHz, Methanol-d₄) δ 6.93-6.84 (m, 1H), 6.27 (s, 1H), 4.48 (s, 2H), 3.67 (br t, J = 12.0 Hz, 4H), 2.52 (s, 3H), 2.29 (s, 3H), 2.26-2.19 (m, 1H), 2.18 (s, 3H), 2.02-1.81 (m, 5H), 1.61 (s, 3H), 1.34-1.21 (m, 2H), 1.13-1.00 (m, 2H). |
| 7 (Enantiomer 2) | 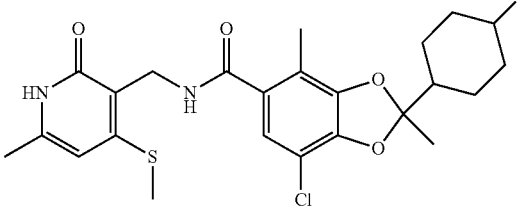<br>(single enantiomer; single geometric isomer)<br>Note: Prepared from intermediate 1 and intermediate 7 (Peak 2) | LCMS [M + H]+ m/z: calc'd 568.2; found 568.3. ¹H NMR (400 MHz, Methanol-d₄) δ 6.89 (s, 1H), 6.27 (s, 1H), 4.49 (s, 2H), 3.61 (t, J = 12.0 Hz, 4H), 2.53 (s, 3H), 2.29 (s, 3H), 2.23-2.08 (m, 4H), 2.03-1.78 (m, 5H), 1.61 (s, 3H), 1.35-1.22 (m, 2H), 1.12-0.99 (m, 2H). |

EXAMPLE 8

7-chloro-N-((4-chloro-6-methyl-2-oxo-1,2-dihydropyridin-3-yl)methyl)-2-(4-(3-cyclopropoxyazetidin-1-yl)cyclohexyl)-2,4-dimethylbenzo[d][1,3]dioxole-5-carboxamide

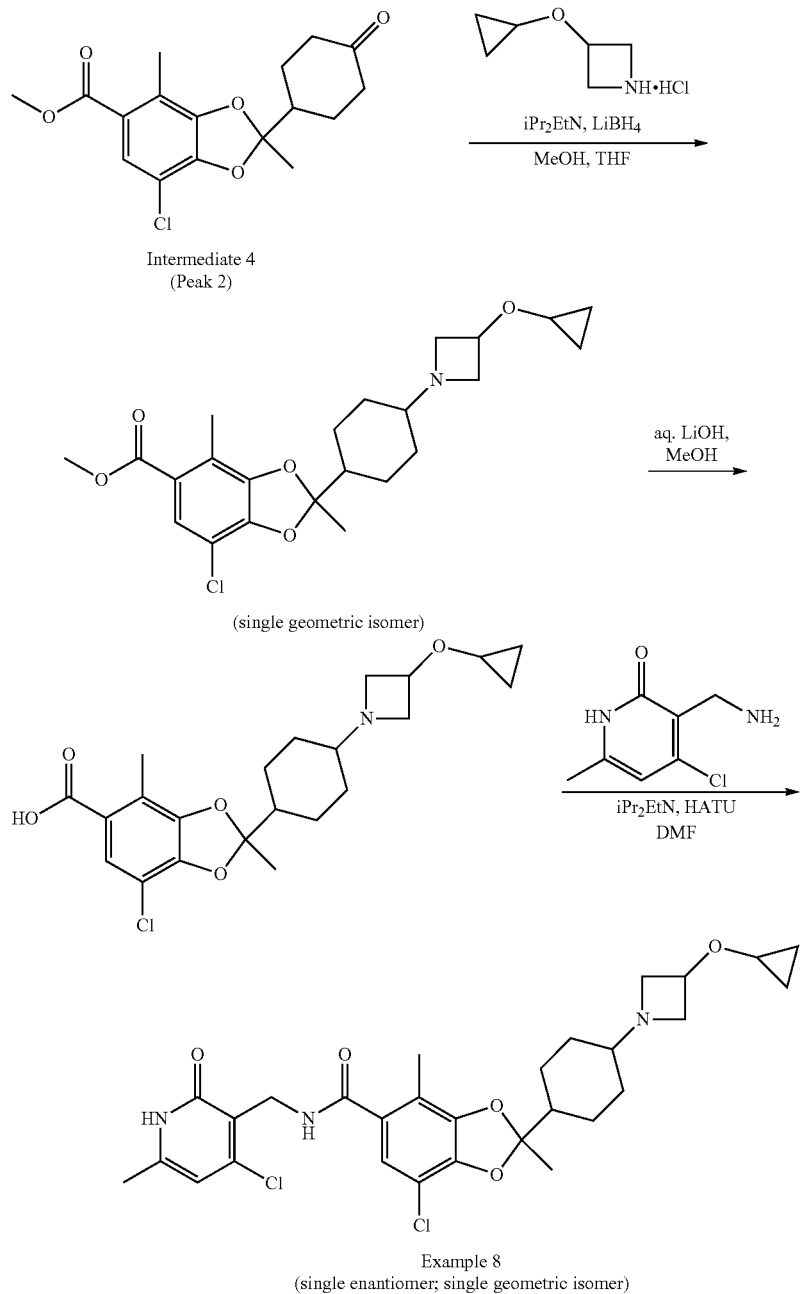

Example 8
(single enantiomer; single geometric isomer)

Step 1: Synthesis of methyl 7-chloro-2-(4-(3-cyclopropoxyazetidin-1-yl)cyclohexyl)-2,4-dimethylbenzo[d][1,3]dioxole-5-carboxylate A solution of 3-(cyclopropoxy)azetidine hydrochloride salt (1.9 g, 12.7 mmol) and N,N-diisopropylethylamine (2.7 mL, 15.5 mmol) in methanol (10 mL) was stirred at room temperature for 1 h before a solution of another solution of methyl 7-chloro-2,4-dimethyl-2-(4-oxocyclohexyl)-1,3-benzodioxole-5-carboxylate (Intermediate 4—Peak 2) (860 mg, 2.54 mmol) in tetrahydrofuran (30 mL) was added. The reaction mixture was stirred at room temperature for 1.5 h then cooled to −70° C. Lithium borohydride (120 mg, 5.51 mmol) was added and the reaction stirred at −70° C. for 30 min [or until complete consumption of the starting material was observed by TLC, ethyl acetate/methanol 5:1]. Next, the reaction was quenched with a saturated aqueous solution of ammonium chloride (100 mL) and the desired product was extracted with ethyl acetate (50 mL×2). The combined organic layers were washed with brine (30 mL), dried over sodium sulfate, filtered and concentrated to dryness under reduced pressure. The residue was purified by flash chromatography (silica gel, gradient 50 to 100% ethyl acetate in petroleum ether) to give title compound (760 mg, 65% yield, 95% purity) as a yellow oil. LCMS [M+H]$^+$ m/z: calc'd. 436.1; found 436.0.

Step 2: Synthesis of 7-chloro-2-(4-(3-cyclopropoxyazetidin-1-yl)cyclohexyl)-2,4-dimethylbenzo[d][1,3]dioxole-5-carboxylic acid To a solution of methyl 7-chloro-2-(4-(3-cyclopropoxyazetidin-l-yl)cyclohexyl)-2,4-dimethylbenzo[d][1,3]dioxole-5-carboxylate (760 mg, 1.74 mmol) in methanol (15 mL) and water (3 mL) was added lithium hydroxide hydrate (962 mg, 22.93 mmol). The reaction was stirred at 70° C. for 15 h. then concentrated under reduced pressure. Water (15mL) was added and the pH adjusted to 6 with a saturated aqueous citric acid solution at 0° C. The desired product was extracted with a 10:1 mixture of dichloromethane and isopropanol (30 mL×3). The combined organic layers were washed with brine (150 mL×2), dried over sodium sulfate, filtered and concentrated to dryness under reduced pressure to give the title compound (720 mg, crude) as a yellow solid, which was used in the next step without further purification. LCMS [M+H]$^+$ m/z: calc'd. 422.1; found 422.0.

Step 3: Synthesis of 7-chloro-N-((4-chloro-6-methyl-2-oxo-1,2-dihydropyridin-3-yl)methyl)-2-(4-(3-cyclopropoxyazetidin-1-yl)cyclohexyl)-2,4-dimethylbenzo[d][1,3]dioxole-5-carboxamide To a solution of 7-chloro-2-[4-[3-(cyclopropoxy)azetidin-1-yl]cyclohexyl]-2,4-dimethyl-1,3-benzodioxole-5-carboxylic acid (360 mg, 0.853 mmol) in N,N-dimethylformamide (4 mL) were added O-(7-azabenzotriazol-1-yl)-N,N,N',N'-tetramethyluronium hexafluorophosphate (500 mg, 1.31 mmol) and N,N-diisopropylethylamine (1 mL, 5.74 mmol). The mixture was stirred at 15° C. for 30 min before 3-(aminomethyl)-4-chloro-6-methyl-1H-pyridin-2-one hydrochloride salt (Intermediate 6) (250 mg, 1.2 mmol) was added. The reaction mixture was stirred at 15° C. for an additional 4 h then filtered. The filtrate was purified by preparative HPLC [Column: Waters Xbridge (150 mm×25 mm, 5 μm). Mobile phase A: water (0.05% ammonia hydroxide v/v/Mobile phase B: acetonitrile. Gradient (65 to 55% mobile phase A/35 to 65% mobile phase B, over 9.5 min). Column temperature: 30° C.] to give the title compound (209 mg, 42% yield) as a white solid. LCMS [M+H]$^+$ m/z: calc'd.576.2; found 576.2. $^1$H NMR (400 MHz, Methanol-d$_4$) δ 6.90 (s, 1H), 6.30 (s, 1H), 4.52 (s, 2H), 4.22 (quin, J=6.0 Hz, 1H), 3.61 (dd, J=6.4, 8.6 Hz, 2H), 3.31-3.25 (m, 1H), 2.99 (dd, J=6.3, 8.4 Hz, 2H), 2.28 (s, 3H), 2.20 (s, 3H), 2.12-2.04 (m, 1H), 1.99-1.85 (m, 5H), 1.62 (s, 3H), 1.33-1.24 (m, 2H), 1.06-0.95 (m, 2H), 0.56-0.51 (m, 2H), 0.51-0.44 (m, 2H).

TABLE 4

The following compounds were prepared in a similar manner as Example 8 using the appropriate starting material.

| Example | Structure | Analytical data |
|---|---|---|
| 9 | 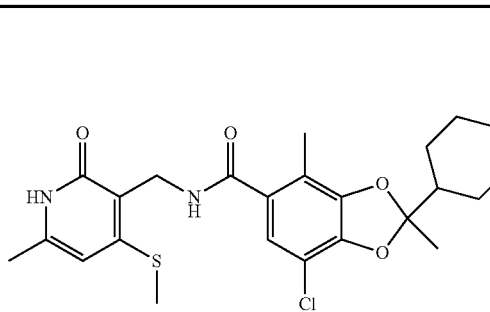 (single enantiomer; single geometric isomer) Prepared from intermediate 1 and intermediate 4 (Peak 2) | LCMS [M + H]$^+$ m/z: calc'd 588.2; found 588.2. $^1$H NMR (400 MHz, Methanol-d$_4$) δ 6.91 (s, 1H), 6.29 (s, 1H), 4.53 (s, 2H), 4.26-4.17 (m, 1H), 3.69-3.59 (m, 2H), 3.30-3.24 (m, 1H), 3.06-2.94 (m, 2H), 2.54 (s, 3H), 2.31 (s, 3H), 2.21 (s, 3H), 2.10-2.02 (m, 1H), 1.99-1.80 (m, 5H), 1.62 (s, 3H), 1.35-1.18 (m, 2H), 1.08-0.93 (m, 2H), 0.58-0.50 (m, 2H), 0.50-0.42 (m, 2H). |
| 10 | 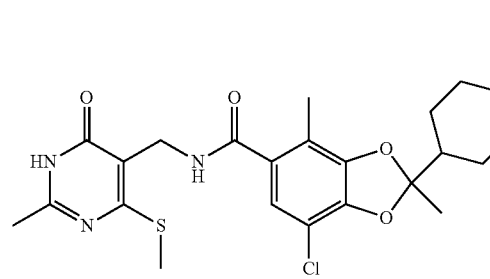 (single enantiomer; single geometric isomer) Prepared from intermediate 2 and intermediate 4 (Peak 2) | LCMS [M + H]$^+$ m/z: calc'd 599.2; found 599.1 $^1$H NMR (400 MHz, Methanol-d$_4$) δ 6.92 (s, 1H), 6.40 (t, J = 76 Hz, 1H), 4.73 (t, J = 8 Hz, 1H), 4.43 (s, 2H), 3.68-3.64 (m, 2H), 3.18-3.14 (m, 2H), 2.57 (s, 3H), 2.40 (s, 3H), 2.21 (s, 3H), 2.14-2.09 (m, 1H), 1.97-1.83 (m, 5H), 1.62 (s, 3H), 1.32-1.23 (m, 2H), 1.05-0.95 (m, 2H). |

TABLE 4-continued

The following compounds were prepared in a similar manner as Example 8 using the appropriate starting material.

| Example | Structure | Analytical data |
|---|---|---|
| 11 | 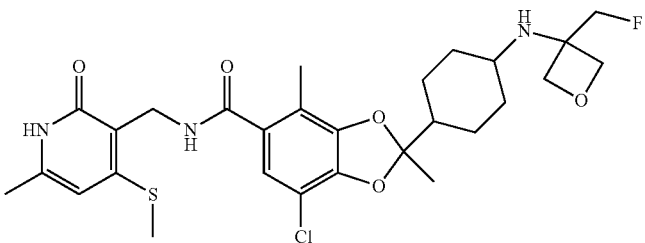 [SMILES: CSc1cc(C)[nH]c(=O)c1CNC(=O)c1cc(Cl)c2c(c1C)OC(C)(C1CCC(NC3(CF)COC3)CC1)O2]<br>(geometric isomer 1)<br>Prepared from intermediate 1 and intermediate 4 (Peak 2) | LCMS [M + H]$^+$ m/z: calc'd 580.2; found 580.2. $^1$H NMR (400 MHz, Methanol-d$_4$) δ 6.91 (s, 1H), 6.29 (s, 1H), 4.82-4.79 (m, 1H), 4.68 (s, 1H), 4.55 (dd, J = 4.0, 6.4 Hz, 2H), 4.52-4.46 (m, 4H), 2.63 (br t, J = 10.8 Hz, 1H), 2.55 (s, 3H), 2.31 (s, 3H), 2.21 (s, 3H), 1.94 (br d, J = 13.2 Hz, 2H), 1.89-1.80 (m, 3H), 1.62 (s, 3H), 1.31 (q, J = 12.0 Hz, 2H), 1.25-1.15 (m, 2H). |
| 11 | 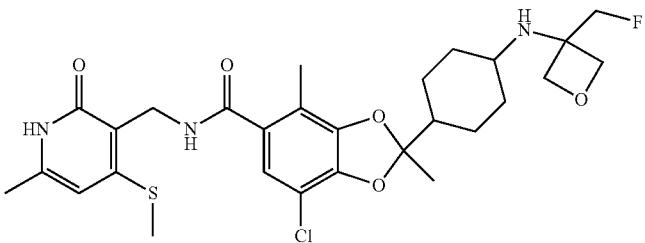 [SMILES: CSc1cc(C)[nH]c(=O)c1CNC(=O)c1cc(Cl)c2c(c1C)OC(C)(C1CCC(NC3(CF)COC3)CC1)O2]<br>(geometric isomer 2)<br>Prepared from intermediate 1 and intermediate 4 (Peak 2) | LCMS [M + H]$^+$ m/z: calc'd 580.2; found 580.1. $^1$H NMR (400 MHz, Methanol-d$_4$) δ 6.91 (s, 1H), 6.30 (s, 1H), 4.75 (s, 1H), 4.63 (s, 1H), 4.62-4.59 (m, 2H), 4.52-4.47 (m, 4H), 3.06 (br s, 1H), 2.55 (s, 3H), 2.31 (s, 3H), 2.22 (s, 3H), 1.91 (br d, J = 10.4 Hz, 1H), 1.68 (br d, J = 8.4 Hz, 4H), 1.65 (s, 5H), 1.61 (br s, 1H), 1.57 (br s, 1H). |
| 12 | 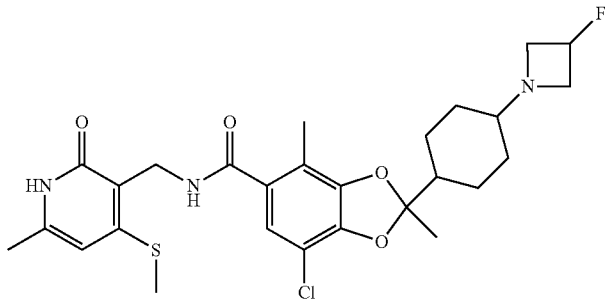 [SMILES: CSc1cc(C)[nH]c(=O)c1CNC(=O)c1cc(Cl)c2c(c1C)OC(C)(C1CCC(N3CC(F)C3)CC1)O2]<br>(single enantiomer; single geometric isomer)<br>Prepared from intermediate 1 and intermediate 4 (Peak 2) | LCMS [M + H]$^+$ m/z: calc'd 572.2; found 571.9. $^1$H NMR (400 MHz, Methanol-d$_4$) δ 6.89 (s, 1H), 6.27 (s, 1H), 4.96-5.23 (m, 1H), 4.48 (s, 2H), 3.54-3.69 (m, 2H), 3.18-3.30 (m, 2H), 2.52 (s, 3H), 2.29 (s, 3H), 2.19 (s, 3H), 2.06-2.15 (m, 1H), 1.80-1.98 (m, 5H), 1.61 (s, 3H), 1.19-1.32 (m, 2H), 0.93-1.05 (m, 2H). |
| 13 | 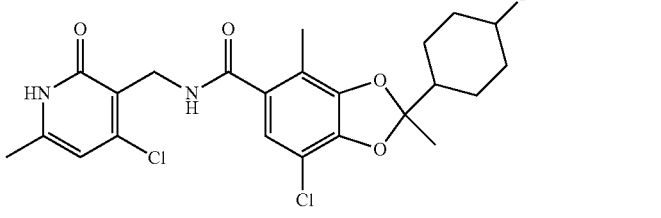<br>(single enantiomer; single geometric isomer)<br>Prepared from intermediate 6 and intermediate 4 (Peak 2) | LCMS [M + H]$^+$ m/z: calc'd 586.2; found 586.1. $^1$H NMR (400 MHz, Methanol-d$_4$) δ 6.90 (s, 1H), 6.40 (t, J = 76 Hz, 1H), 6.30 (s, 1H), 4.73 (t, J = 8 Hz, 1H), 4.53 (s, 2H), 3.68-3.64 (m, 2H), 3.18-3.14 (m, 2H), 2.28 (s, 3H), 2.20 (s, 3H), 2.15-2.08 (m, 1H), 1.97-1.83 (m, 5H), 1.63 (s, 3H), 1.35-1.23 (m, 2H), 1.05-0.90 (m, 2H). |

EXAMPLE 14

(R)-7-chloro-2,4-dimethyl-N-((6-methyl-4-(methylthio)-2-oxo-1,2-dihydropyridin-3-yl)methyl)-2-(1-(2,2,2-trifluoroethyl)piperidin-4-yl)benzo[d][1,3]dioxole-5-carboxamide and (S)-7-chloro-2,4-dimethyl-N-((6-methyl-4-(methylthio)-2-oxo-1,2-dihydropyridin-3-yl)methyl)-2-(1-(2,2,2-trifluoroethyl)piperidin-4-yl)benzo[d][1,3]dioxole-5-carboxamide

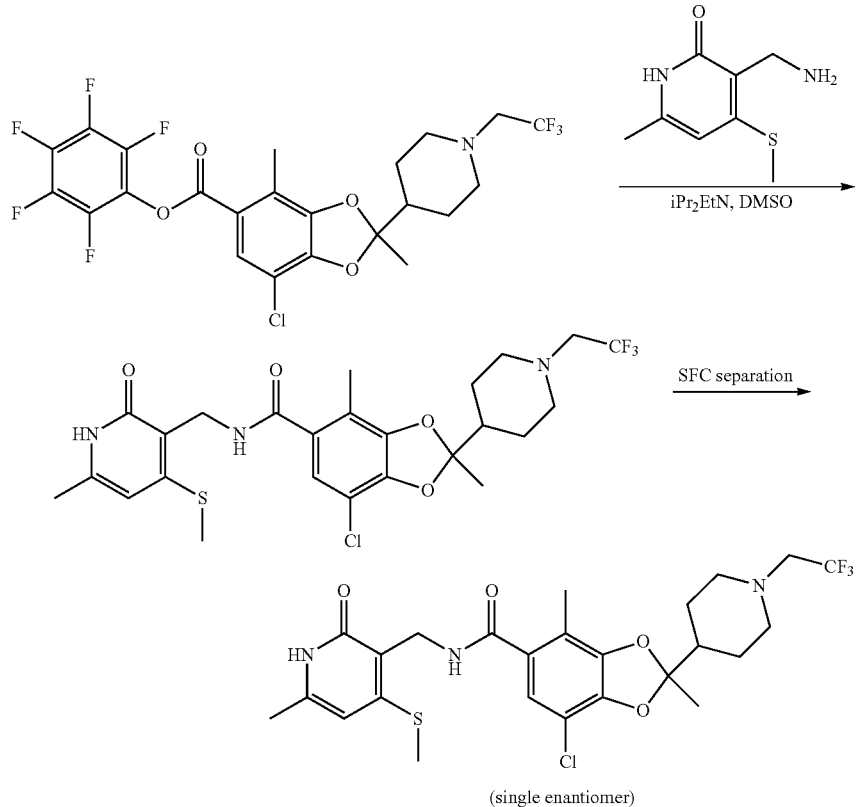

(single enantiomer)

Step 1: Synthesis of 7-chloro-2,4-dimethyl-N-((6-methyl-4-(methylthio)-2-oxo-1,2-dihydropyridin-3-yl)methyl)-2-(1-(2,2,2-trifluoroethyl)piperidin-4-yl)benzo[d][1,3]dioxole-5-carboxamide To a solution of 2,3,4,5,6-pentafluorophenyl 7-chloro-2,4-dimethyl-[(2-(2,2,2-trifluoroethyl)piperidin-4-yl]-2H-1,3-benzodioxole-5-carboxylate (Intermediate 8) (752 mg, 1.34 mmol) in dimethylsulfoxide (4 mL) were added 3-(aminomethyl)-6-methyl-4-(methylsulfanyl)-1,2-dihydropyridin-2-one (Intermediate 1) (740 mg, 4.02 mmol) and N,N-diisopropylethylamine (932 µL, 5.36 mmol). The reaction mixture was heated at 60° C. and after 1 h added onto a C18 column for purification. The desired product was purified twice by reverse phase flash chromatography (C18 column, gradient 0 to 100% acetonitrile in water with 0.1% of trifluoroacetic acid) to give the title compound (289 mg, 38% yield) as a racemic mixture as a gum.

Step 2: Separation of (R)-7-chloro-2,4-dimethyl-N-((6-methyl-4-(methylthio)-2-oxo-1,2-dihydropyridin-3-yl)methyl)-2-(1-(2,2,2-trifluoroethyl)piperidin-4-yl)benzo[d][1,3]dioxole-5-carboxamide and (S)-7-chloro-2,4-dimethyl-N-((6-methyl-4-(methylthio)-2-oxo-1,2-dihydropyridin-3-yl)methyl)-2-(1-(2,2,2-trifluoroethyl)piperidin-4-yl)benzo[d][1,3]dioxole-5-carboxamide The racemic mixture of 7-chloro-2,4-dimethyl-N-((6-methyl-4-(methylthio)-2-oxo-1,2-dihydropyridin-3-yl)methyl)-2-(1-(2,2,2-trifluoroethyl)piperidin-4-yl)benzo[d][1,3]dioxole-5-carboxamide (289 mg) was resolved by preparative SFC [Column: ChromegaChiral CC4 from ES Industries (250 mm×20 mm I.D.). Mobile phase A: $CO_2$/ Mobile phase B: 0.25% isopropylamine in methanol. Isocratic (55% mobile phase A and 45% mobile phase B). Flow rate: 80 g/min. Column temperature: 25° C.]SFC analytical method: Column: Chiralcel OX-H from Chiral Technologies (100 mm×4.6 mm I.D.). Mobile phase A: CO2/Mobile phase B: 0.1% isopropylamine in methanol. Isocratic (75% mobile phase A and 25% mobile phase B). Flow rate: 4 mL/min. Column temperature: 40° C. Example 16 (Enantiomer 1) (desired enantiomer/eutomer): Retention time=3.74 min (SFC analytical method). Recovery=90 mg, 12% yield, 99% ee (yellow solid). LCMS [M+H]$^+$ m/z: calc'd 560.2; found 560.2. $^1$H NMR (400 MHz, Methanol-$d_4$) δ 6.89 (s, 1H), 6.27 (s, 1H), 4.49 (s, 2H), 3.08-2.98 (m, 4H), 2.52 (s, 3H), 2.34 (br t, J=11.0 Hz, 2H), 2.29 (s, 3H), 2.20 (s, 3H), 1.93-1.84 (m, 1H), 1.83-1.76 (m, 2H), 1.62 (s, 3H), 1.60-1.47 (m, 2H). Example 16 (Enantiomer 2) (undesired enantiomer/distomer): Retention time=4.25 min (SFC analytical method). Recovery=101 mg g, 13% yield, 98% ee, (yellow solid). LCMS [M+H]$^+$ m/z: calc'd 560.2; found 560.2. $^1$H NMR (400 MHz, Methanol-$d_4$) δ 6.89 (s, 1H), 6.27 (s, 1H), 4.49 (s, 2H), 3.08-2.98 (m, 4H), 2.52 (s, 3H), 2.34 (br t, J=11.0 Hz, 2H), 2.29 (s, 3H), 2.20 (s, 3H), 1.93-1.84 (m, 1H), 1.83-1.76 (m, 2H), 1.62 (s, 3H), 1.60-1.47 (m, 2H).

EXAMPLE 15

7-chloro-N-((4-chloro-6-methyl-2-oxo-1,2-dihydro-pyridin-3-yl)methyl)-2-(4-(3-methoxyazetidin-1-yl)cyclohexyl)-2,4-dimethylbenzo[d][1,3]dioxole-5-carboxamide

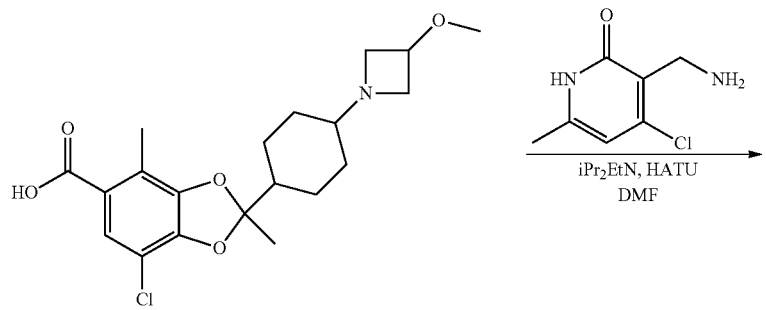

Intermediate 9
(single enantiomer; single geometric isomer)

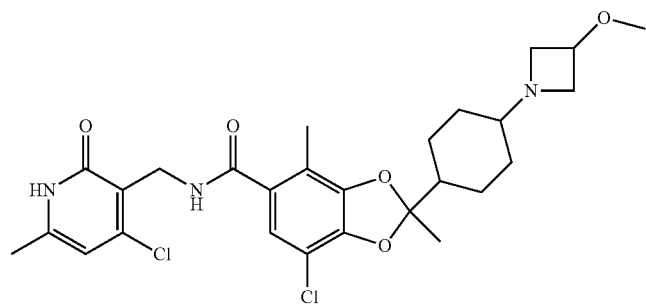

Example 15
(single enantiomer; single geometric isomer)

To a solution of 7-chloro-2-(4-(3-methoxyazetidin-1-yl)cyclohexyl)-2,4-dimethylbenzo[d][1,3]dioxole-5-carboxylic acid (900 mg, 2.27 mmol) in N,N-dimethylformamide (5 mL) were added O-(7-azabenzotriazol-1-yl)-N,N,N',N'-tetramethyluronium hexafluorophosphate (1.04 g, 2.73 mmol) and N,N-diisopropylethylamine (2.38 mL, 13.6 mmol). The mixture was stirred at 25° C. for 30 min before 3-(aminomethyl)-4-chloro-6-methyl-1H-pyridin-2-one hydrochloride salt (Intermediate 6) (710 mg, 3.4 mmol) was added. The reaction mixture was stirred at room temperature for an additional 1.5 h then filtered. The filtrate was purified by preparative HPLC twice [Column: YMC-Actus Triart C18 (100 mm×30 mm, 5 μm). Mobile phase A: water (0.05% hydrochloric acid)/Mobile phase B: acetonitrile. Gradient (85 to 55% mobile phase A/15 to 45% mobile phase B, over 10 min). Column temperature: 30° C. and Column: Xtimate C18 (150 mm×25 mm, 5 μm). Mobile phase A: water (0.05% ammonia hydroxide v/v)/Mobile phase B: acetonitrile. Gradient (69 to 39% mobile phase A/31 to 61% mobile phase B, over 7 min). Column temperature: 30° C.] to give the title compound (533 mg, 43% yield, >99% purity) as a white solid. LCMS [M+H]$^+$m/z: calc'd 550.2; found 550.1. $^1$H NMR (400 MHz, Chloroform-d) δ 11.97 (br, 1H), 7.06-7.03 (m, 1H), 6.88 (s, 1H), 6.19 (s, 1H), 4.65 (d, J=6.0 Hz, 2H), 4.05-4.01 (m, 1H), 3.66-3.62 (m, 2H), 3.25 (s, 3H), 2.93-2.90 (m, 2H), 2.28 (s, 3H), 2.25 (s, 3H), 1.93-1.81 (m, 6H), 1.60 (s, 3H), 1.25-1.02 (m, 4H).

EXAMPLE 16

(R)-7-chloro-N-((4-chloro-6-methyl-2-oxo-1,2-dihydropyridin-3-yl)methyl)-2,4-dimethyl-2-(1-(2,2,2-trifluoroethyl)piperidin-4-yl)benzo[d][1,3]dioxole-5-carboxamide and (S)-7-chloro-N-((4-chloro-6-methyl-2-oxo-1,2-dihydropyridin-3-yl)methyl)-2,4-dimethyl-2-(1-(2,2,2-trifluoroethyl)piperidin-4-yl)benzo[d][1,3]dioxole-5-carboxamide

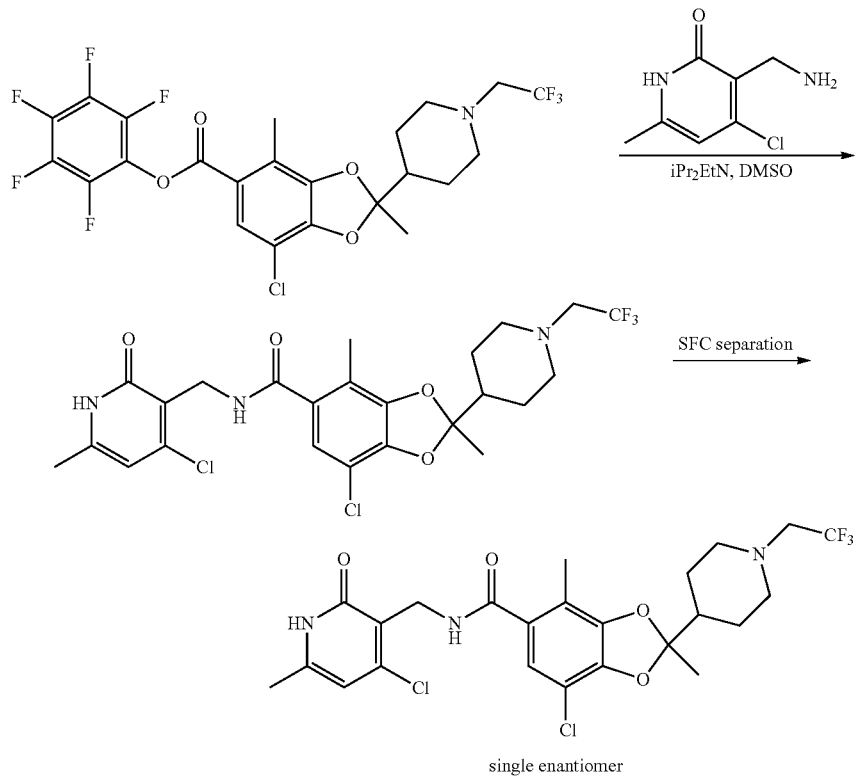

single enantiomer

Step 1: Synthesis of 7-chloro-N-((4-chloro-6-methyl-2-oxo-1,2-dihydropyridin-3-yl)methyl)-2,4-dimethyl-2-(1-(2,2,2-trifluoroethyl)piperidin-4-yl)benzo[d][1,3]dioxole-5-carboxamide To a solution of 2,3,4,5,6-pentafluorophenyl 7-chloro-2,4-dimethyl-[(1-(2,2,2-trifluoroethyl)piperidin-4-yl]-2H-1,3-benzodioxole-5-carboxylate (Intermediate 8) (188 mg, 0.3358 mmol) in dimethylsulfoxide (1 mL) were added 3-(aminomethyl)-4-chloro-6-methyl-1,2-dihydropyridin-2-one hydrochloride salt (Intermediate 6) (70.2 mg, 0.336 mmol) and N,N-diisopropylethylamine (233 μL, 1.34 mmol). The reaction mixture was heated at 60° C. and after 1 h added onto a C18 column for purification. The desired product was purified twice by reverse phase flash chromatography (C18 column, gradient 0 to 100% acetonitrile in water with 0.1% of trifluoroacetic acid) to give the title compound (180 mg, 98% yield) as a racemic mixture as a gum.

Step 2: Separation of (R)-7-chloro-N-((4-chloro-6-methyl-2-oxo-1,2-dihydropyridin-3-yl)methyl)-2,4-dimethyl-2-(1-(2,2,2-trifluoroethyl)piperidin-4-yl)benzo[d][1,3]dioxole-5-carboxamide and (S)-7-chloro-N-((4-chloro-6-methyl-2-oxo-1,2-dihydropyridin-3-yl)methyl)-2,4-dimethyl-2-(1-(2,2,2-trifluoroethyl)piperidin-4-yl)benzo[d][1,3]dioxole-5-carboxamide The racemic mixture of 7-chloro-N-((4-chloro-6-methyl-2-oxo-1,2-dihydropyridin-3-yl)methyl)-2,4-dimethyl-2-(1-(2,2,2-trifluoroethyl)piperidin-4-yl)benzo[d][1,3]dioxole-5-carboxamide (180 mg) was resolved by preparative SFC [Column: ChromegaChiral CC4 from ES Industries (250 mm×20 mm I.D.). Mobile phase A: $CO_2$/Mobile phase B: 0.25% isopropylamine in methanol. Isocratic (65% mobile phase A and 35% mobile phase B). Flow rate: 80 g/min. Column temperature: 25° C.]. SFC analytical method: Column: Chiralcel OZ-H from Chiral Technologies (100 mm×4.6 mm I.D., xxμm). Mobile phase A: $CO_2$/Mobile phase B: 0.1% isopropylamine in methanol. Isocratic (65% mobile phase A and 35% mobile phase B). Flow rate: 4 mL/min. Column temperature: 40° C. Example 17 (Enantiomer 1) (desired enantiomer/eutomer): Retention time=0.73 min (SFC analytical method). Recovery=61 mg, 33% yield,100% ee (yellow solid). Example 17 (Enantiomer 2) (undesired enantiomer/distomer): Retention time=0.98 min (SFC analytical method). Recovery=63 mg, 34% yield, 97 ee, (yellow solid). LCMS [M+H]+ m/z: calc'd 548.1; found 548.2. $^1$H NMR (400 MHz, Methanol-$d_4$) δ 6.89 (s, 1H), 6.29 (s, 1H), 4.52 (s, 2H), 3.04 (q, J=9.8 Hz, 4H), 2.35 (br t, J=11.0 Hz, H), 2.27 (s, 3H), 2.19 (s, 3H), 1.95-1.85 (m, 1H), 1.85-1.75 (m, 2H), 1.63 (s, 3H), 1.62-1.50 (m, 2H).

EXAMPLE 17

7-chloro-2-(4-(3-methoxyazetidin-1-yl)cyclohexyl)-2,4-dimethyl-N-((6-methyl-4-(methylthio)-2-oxo-1,2-dihydropyridin-3-yl)methyl)benzo[d][1,3]dioxole-5-carboxamide

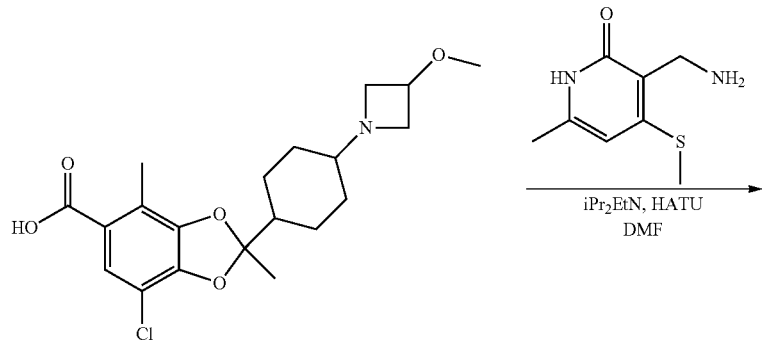

Intermediate 9
(single enantiomer; single geometric isomer)

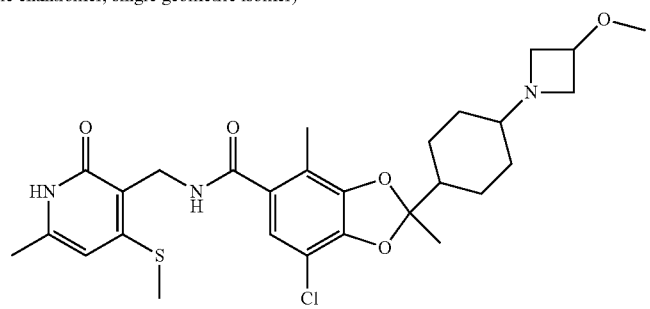

Example 17
(single enantiomer; single geometric isomer)

To a solution of 7-chloro-2-(4-(3-methoxyazetidin-1-yl)cyclohexyl)-2,4-dimethylbenzo[d][1,3]dioxole-5-carboxylic acid (Intermediate 9 - single enantiomer and geometric isomer) (5 g, 12.63 mmol) in N,N-dimethylformamide (50 mL) were added O-7-azabenzotriazol-1-yl)-N,N,N',N'-tetramethyluronium hexafluorophosphate (5.7 g, 14.99 mmol) and N,N-diisopropylethylamine (11 mL, 63.15 mmol). The mixture was stirred at 20° C. for 30 min before 3-(aminomethyl)-6-methyl-4-(methylthio)pyridin-2(1H)-one hydrochloride salt (Intermediate 1) (4.2 g, 19.03 mmol) was added. The reaction mixture was stirred at room temperature for an additional 1.5 h then filtered. The filtrate was purified by preparative HPLC [Column: Phenomenex Gemini C18 (250 mm×50 mm, 10 μm). Mobile phase A: water (0.04% ammonia hydroxide v/v and 10 mM ammonium bicarbonate)/Mobile phase B: acetonitrile. Gradient (75 to 44% mobile phase A/25 to 56% mobile phase B, over 23 min). Column temperature: 30° C.] to give the title compound (4.4 g, 60% yield, 96% purity as a white solid. LCMS [M+H]+ m/z: calc'd.562.2; found 562.2. $^1$H NMR (400 MHz, Methanol-$d_4$) δ 6.91 (s, 1H), 6.29 (s, 1H), 4.50 (s, 2H), 4.01 (quin, J=6 Hz, 1H), 3.58 (dd, J=8.8, 6.4 Hz, 2H), 3.26 (s, 3H), 2.92-3.02 (m, 2H), 2.54 (s, 3H), 2.31 (s, 3H), 2.21 (s, 3H), 2.01-2.11 (m, 1H), 1.79-2.00 (m, 5H), 1.62 (s, 3H), 1.19-1.34 (m, 2H), 0.91-1.08 (m, 2H).

EZH2 Assays $IC_{50}$ Measurements for Inhibitors using EZH2

EZH2 biochemical assay ($IC_{50}$): Compound potencies were assessed through incorporation of $^3$H-SAM into a biotinylated H3 peptide. Specifically, 30 pM PRC2 containing wt EZH2 (pentameric complex prepared in-house) was pre-incubated with 450 nM SAM, 450 nM $^3$H-SAM, 2 μM H3K27me3 activating peptide (H$_2$N-RKQLATKAAR(Kme3)SAPATGGVKKP-amide) and compounds (as 10 point duplicate dose response titrations in DMSO, final assay 0.8% DMSO (v/v)) for 3-5 h in 50 mM Tris (pH 8.5), 1 mM DTT, 0.07 mM Brij-35, 0.1% BSA, and 0.8% DMSO in a total volume of 12.5 μl. Reaction was initiated with biotinylated H3 substrate peptide (H$_2$N-RKQLATKAAR(Kme1)SAPATGGVKKP-NTPEGBiot) as a 2 μM stock in 12.5 μl of buffer and allowed to react at room temperature for 18-22 h. Quenching was accomplished by addition of 20 μl of STOP solution (50 mM Tris (pH 8.5), 200 mM EDTA, 2 mM SAH). 35 μl of the quenched solution was transferred to streptavidin coated FlashPlates (PerkinElmer), incubated 1-2 h, washed, and read in a TopCount Reader (PerkinElmer). $IC_{50}$s were calculated in Genedata Screener using non-linear least square four parameter fits, where the four parameters were $IC_{50}$, Hill slope, pre-transitional baseline (0% INH), and post-transitional baseline (100% INH).

EC$_{50}$ Measurements for Inhibitors in HeLa Cell Assays

H3K27me3 Alpha Hela Assay (AlphaLISA). Ten different doses of each test compound (in a series of 3-fold dilutions) were plated in duplicate 384-well tissue culture treated plates (Catalog #6007680; Perkin Elmer, Waltham, Mass.). Hela cells grown in culture were trypsinized and counted using a Countess® cell counter (Catalog #C10281; Life Technologies, Grand Island, N.Y.). Cell were diluted to 67,000 cells per mL in10% DMEM (Catalog #10569-010 Life Technologies, Grand Island, N.Y.) and 15 µL (1,000 cells) were plated into each well using the Biotek Micro-Flo™ Select Dispenser (BioTek Instruments, Inc. Vermont, USA),) of the 384-well plate. Plates were incubated at 37° C./5% CO$_2$ for 72 hrs. One of the duplicate plates was processed for HeLa assay and the other for viability. 5 µL of Cell-Histone Lysis buffer (1×) (Catalog #AL009F1 Perkin Elmer; Waltham, Mass.) per well was added to the plate processed for AlphaLISA and the plate was incubated at RT for 30 minutes on a plate shaker with low speed (Model# 4625-Q Thermo Scientific; Waltham, Mass.). Then, 10 µL per well Histone Extraction buffer (catalog #AL009F2; Perkin Elmer; Waltham, Mass.) was added and the plate further incubated at RT for 20 min on plate shaker with low speed. Next, 10 µL of 5× mix of anti-K27me3 acceptor beads plus Biotinylated anti-Histone H3 (C-ter) Antibody (diluted to 3 nM final) (Catalog #AL118 Perkin Elmer; Waltham, Mass.) was added in each well. Dilution of the acceptor beads and anti-Histone H3 was done in 1× Histone Detection buffer (Catalog #AL009F3 Perkin Elmer; Waltham, Mass.) which was produced by diluting the 10× stock provided. The plate was sealed with an aluminum plate sealer and incubated at 23° C. for 60 min. Next, 10 µL 5× solution of Streptavidin Donor beads were added (Catalog #6760002 Perkin Elmer; Waltham, Mass.) (20 µg/mL final in 1× Histone Detection Buffer), =plate was sealed with Aluminum plate sealer and incubated at 23° C. for 30 min. The plates were then read using an EnVision-Alpha Reader (model #2104 Perkin Elmer; Waltham, Mass.).

Cell viability was assayed by adding 15 µL of Cell Titer Glo ((Catalog #G9241 Promega Madison, Wis.) to each well with cells with media. The plates were incubated at RT for 15-20 minutes on a plate shaker at low speed. The plates were then read using an EnVision-Alpha Reader (model #2104 Perkin Elmer; Waltham, Mass.).

GI$_{50}$ Measurements for Inhibitors in Karpas-422 Viability Assays

Karpas-422 cell lines were obtained from DSMZ (Braunschweig, Germany) and were grown in RPMI-1640 media. All media contained 10% fetal bovine serum (FBS) and 1% penicillin/streptomycin (Invitrogen). 20K cells per well were plated onto 96 well compound coated plates. Cells were split and seeded at original plating density (based on the DMSO well counts) every 4 days into plates containing fresh EZH2 inhibitors. Relative cell numbers were assessed by Cell Titer-Glo luminescent cell viability assay (Promega) on Day 8. GraphPad Prism 5 was used for curve fitting and GI$_{50}$ values were reported. Data is shown in Table 5.

TABLE 5

| Example | EZH2 IC$_{50}$ (pM) | HeLa EC$_{50}$ (nM) | Karpas-422 GI$_{50}$ (nM) |
|---|---|---|---|
| 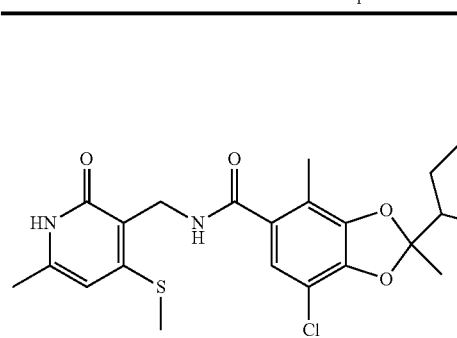 Example 1 (single enantiomer, single geometric isomer) | 91 | 0.52 | 3.9 |
| 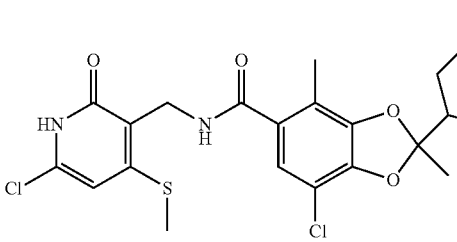 Example 2 | 1,500 | 15 | 250 |

TABLE 5-continued

| Example | EZH2 IC$_{50}$ (pM) | HeLa EC$_{50}$ (nM) | Karpas-422 GI$_{50}$ (nM) |
|---|---|---|---|
| (single enantiomer; single geometric isomer) Example 3 | 370 | 2.4 | 29 |
| Example 4 (R enantiomer; trans geometric isomer) | 38 | 0.51 | 4.0 |
| Example 5 (R enantiomer; trans geometric isomer) | 54 | 3.6 | 22 |
| Example 6-Enantiomer 1 (single enantiomer; single geometric isomer) | 1,800 | 39 | 720 |

TABLE 5-continued
| Example | EZH2 IC$_{50}$ (pM) | HeLa EC$_{50}$ (nM) | Karpas-422 GI$_{50}$ (nM) |
|---|---|---|---|
| 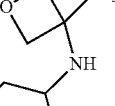<br>Example 6-Enantiomer 2<br>(single enantiomer; single geometric isomer) | 140 | 4.2 | 53 |
| 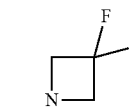<br>Example 7-Enantiomer 1<br>(single enantiomer; single geometric isomer) | 8,600 | | |
| 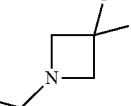<br>Example 7-Enantiomer 2<br>(single enantiomer; single geometric isomer) | 120 | | 12 |
| 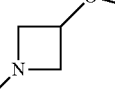<br>Example 8<br>(single enantiomer; single geometric isomer) | 39 | 0.52 | 5.0 |

TABLE 5-continued
| Example | EZH2 IC$_{50}$ (pM) | HeLa EC$_{50}$ (nM) | Karpas-422 GI$_{50}$ (nM) |
|---|---|---|---|
| 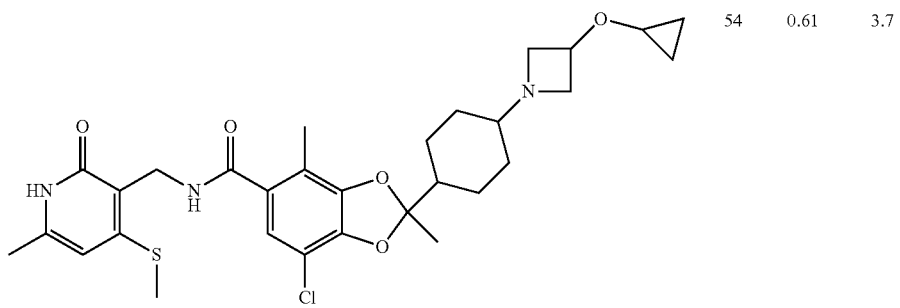<br>Example 9<br>(single enantiomer; single geometric isomer) | 54 | 0.61 | 3.7 |
| 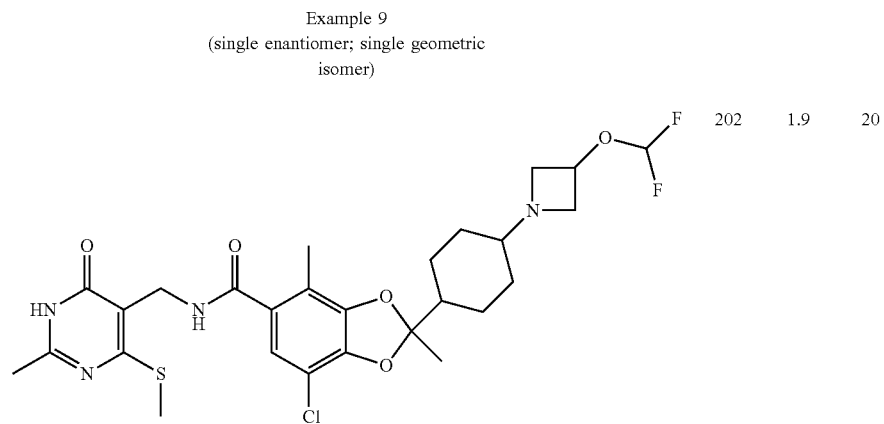<br>Example 10<br>(single enantiomer; single geometric isomer) | 202 | 1.9 | 20 |
| 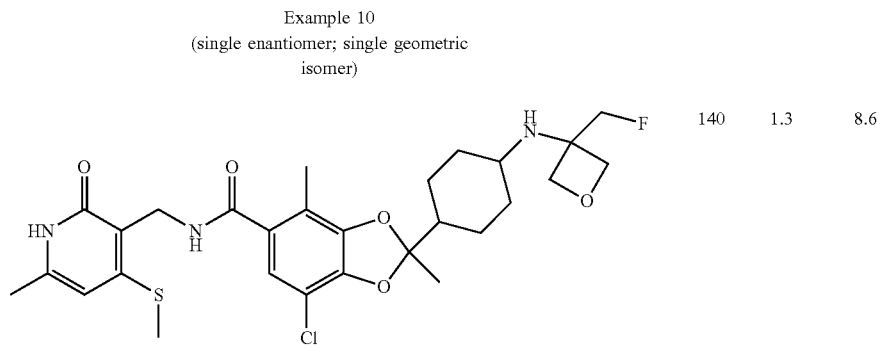<br>Example 11<br>(single enantiomer; geometric isomer 1) | 140 | 1.3 | 8.6 |
| 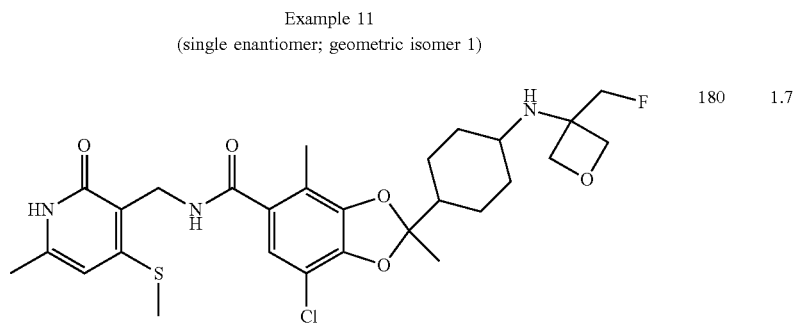<br>Example 11<br>(single enantiomer; geometric isomer 2) | 180 | 1.7 | |

TABLE 5-continued
| Example | EZH2 IC$_{50}$ (pM) | HeLa EC$_{50}$ (nM) | Karpas-422 GI$_{50}$ (nM) |
|---|---|---|---|
| 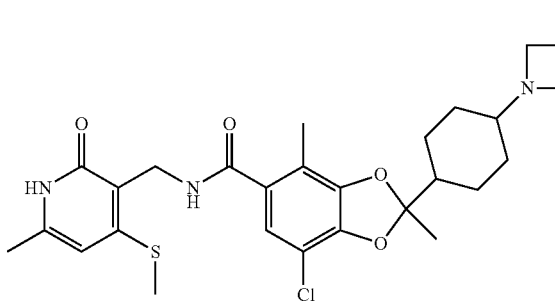<br>Example 12<br>(single enantiomer; single geometric isomer) | 92 | 0.59 | 4.4 |
| 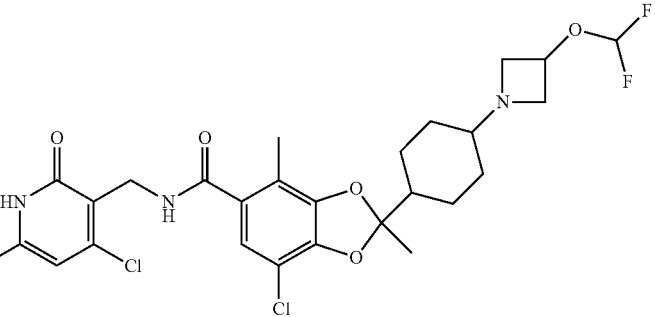<br>Example 13<br>(single enantiomer; single geometric isomer) | 84 | 0.81 | 9.7 |
| 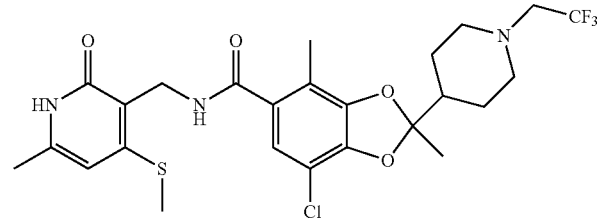 [SMILES: CSc1cc(C)[nH]c(=O)c1CNC(=O)c1cc(Cl)c2c(c1C)OC(C)(C1CCN(CC(F)(F)F)CC1)O2]<br>Example 14-Enantiomer 1<br>(single enantiomer; single geometric isomer) | 37 | 1.4 | |
| 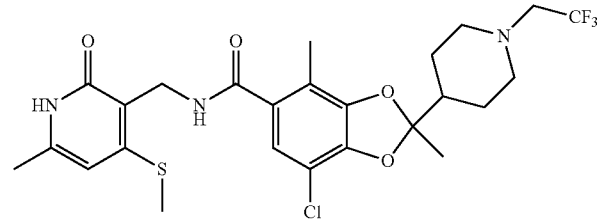 [SMILES: CSc1cc(C)[nH]c(=O)c1CNC(=O)c1cc(Cl)c2c(c1C)OC(C)(C1CCN(CC(F)(F)F)CC1)O2]<br>Example 14-Enantiomer 2<br>(single enantiomer) | 7,000 | 210 | |

TABLE 5-continued

| Example | EZH2 IC$_{50}$ (pM) | HeLa EC$_{50}$ (nM) | Karpas-422 GI$_{50}$ (nM) |
|---|---|---|---|
| 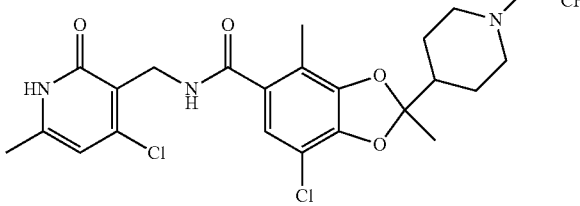<br>Example 16-Enantiomer 1<br>(single enantiomer) | 310 | 22 | |
| 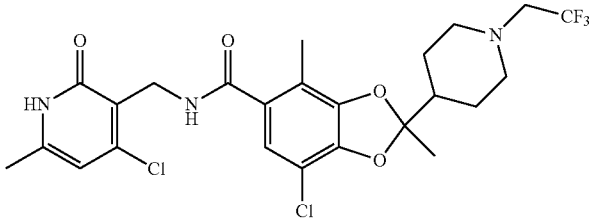 [SMILES: Cc1cc(Cl)c(CNC(=O)c2cc(Cl)c3c(c2C)OC(C)(C2CCN(CC(F)(F)F)CC2)O3)c(=O)[nH]1]<br>Example 16-Enantiomer 2<br>(single enantiomer) | >10,000 | >300 | |
| 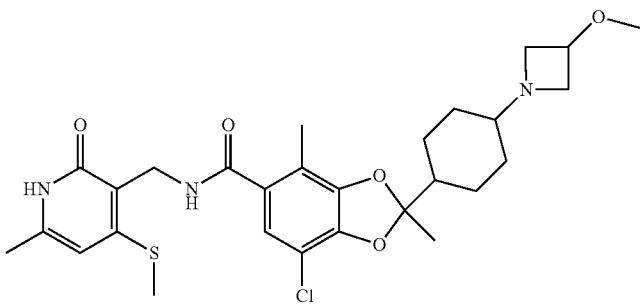<br>Example 17<br>(single enantiomer; single geometric isomer) | 43 | 0.33 | 3.5 |

Residence Time Measurements

EZH2 residence time assay: Compound residence times were assessed by monitoring the recovery of enzyme activity following a 100-fold dilution of pre-formed enzyme-inhibitor complex (dilution reaction), and comparing it to the activity of an undiluted control with the same final concentrations of all reagents (control reaction). Enzyme activity was measured by incorporation of $^3$H-SAM into a biotinylated H3 peptide. For the dilution reaction, 20 nM PRC2 containing wt EZH2 (pentameric complex prepared in-house) was pre-incubated with 1 μM activating peptide (H$_2$N-RKQLATKAAR(Kme3)SAPATGGVKKP-amide) and compound at 600 times its K$_i$ for 2 h in 40 μL of buffer (50 mM Tris pH 8.5, 4 mM DTT, 1 mM MgCl$_2$, 0.07 mM Brij-35, and 0.1 mg/mL BSA), then diluted 100-fold and the reaction initiated by transferring 1.4 μL to a 138.6 μL volume of buffer containing 1 μM activating peptide, 5.05 μM substrate peptide (H$_2$N-RKQLAT-KAARKSAPATGGVKKP-NTPEGbiot), 1.01 μM SAM, and 1.01 μM $^3$H-SAM. For the control reaction, 0.202 nM PRC2 was pre-incubated with 1 μM activating peptide, 1.01 μM SAM, 1.01 μM $^3$H-SAM, and compound at 6.06 times its Ki for 2 h in 138.6 μL of buffer, then the reaction was initiated by the addition of 1.4 μL 500 μM substrate peptide in water. Reactions were quenched at various time points spanning up to 10 hours, by transferring 8μL aliquots from the reaction vessel to a plate containing 8μL per well of STOP solution (50 mM Tris pH 8.5, 200 mM EDTA, 2 mM SAH). After the last time point, 12 μL of the quenched solutions were transferred to a streptavidin coated FlashPlate (PerkinElmer) containing 40 μL per well of STOP solution, incubated 1-8 h, washed, and read in a TopCount plate reader (PerkinElmer).

A custom script was used to fit control reaction progress data to a straight line and dilution reaction progress data:

$$y = v_s t + \frac{v_i - v_s}{k_{obs}}\left(1 - e^{-k_{obs}t}\right) + \text{background}$$

Where y is the product formed, t is the reaction time, v$_i$ is the initial velocity, v$_s$ is the steady state velocity, and k$_{obs}$ is the rate constant for the transition from the initial velocity phase of the curve to the steady state velocity phase of the curve. In fitting the dilution reaction progress data, $v_s$ was constrained to the slope of the line fitted to the control reaction progress data. The fitted value of $k_{obs}$ was then transformed into residence time:

$$\tau = \frac{[EI] - \frac{1}{K_i}[E][I]}{k_{obs}[EI]}$$

Where $\tau$ is residence time, $K_i$ is the inhibition constant, [EI] is the calculated equilibrium concentration of enzyme-inhibitor complex, [E] is the calculated equilibrium concentration of free enzyme, and [I] is the calculated equilibrium concentration of free inhibitor.

Cellular Permeability Measurements for Inhibitors in MDCK Assay

Cell culture: MDCK II cells (obtained from Piet Borst at the Netherlands Cancer Institute) were seeded onto polyethylene membranes (PET) in 96-well BD insert systems at 2.5×105 cells/mL until to 4-7 days for confluent cell monolayer formation.

Experimental procedure: Test and reference compounds (nadolol, metoprolol and digoxin) were diluted with transport buffer (HBSS with 10mM Hepes, pH7.4) from stock solution to a concentration of 2 µM (<1% DMSO) and applied to the apical (A) or basolateral (B) side of the cell monolayer. Permeation of the test compounds from A to B direction or B to A direction was determined in duplicate with P-gp inhibitor (GF120918, 10 µM). Digoxin was tested at 10 µM from A to B direction or B to A direction with/without P-gp inhibitor (GF120918, 10 µM) as well, while nadolol and metoprolol were tested at 2 µM in A to B direction without P-gp inhibitor (GF120918, 10 µM) in duplicate. The plate was incubated for 2.5 hours in $CO_2$ incubator at 37±1° C., with 5% $CO_2$ at saturated humidity without shaking. In addition, the efflux ratio of each compound was also determined. Test and reference compounds were quantified by LC/MS/MS analysis based on the peak area ratio of analyte/IS. After transport assay, Lucifer yellow rejection assay are applied to determine the cell monolayer integrity. Buffers are removed from both apical and basolateral chambers, followed by the addition of 75 µL of 100 µM lucifer yellow in transport buffer and 250 µL transport buffer in apical and basolateral chambers, respectively. The plate is incubated for 30 minutes at 37° C. with 5% $CO_2$ and 95% relative humidity without shaking. After 30 minutes incubation, 20 µL of lucifer yellow samples are taken from the apical sides, followed by the addition of 60 µL of Transport Buffer. And then 80 µL of lucifer yellow samples are taken from the basolateral sides. The relative fluorescence unit (RFU) of lucifer yellow is measured at 425/528 nm (excitation/emission) with a Molecular Device M2e plate reader.

Data analysis: The apparent permeability coefficient Papp (cm/s) was calculated using the equation:

$P_{app} = (dC_r/dt) \times V_r/(A \times C_0)$

Where $dC_r/dt$ is the cumulative concentration of compound in the receiver chamber as a function of time (µM/s); $V_r$ is the solution volume in the receiver chamber (0.075 mL on the apical side, 0.25 mL on the basolateral side); A is the surface area for the transport, i.e. 0.0804 cm2 for the area of the monolayer; $C_0$ is the initial concentration in the donor chamber (µM).

The efflux ratio was calculated using the equation:

Efflux Ratio=$P_{app}(BA)/P_{app}(AB)$

Percent recovery was calculated using the equation:

% Recovery=$100 \times [(V_r \times C_r) + (V_d \times C_d)]/(V_d \times C_0)$

Where $V_d$ is the volume in the donor chambers (0.075 mL on the apical side, 0.25 mL on the basolateral side); $C_d$ and $C_r$ are the final concentrations of transport compound in donor and receiver chambers, respectively.

Percent of lucifer yellow in basolateral well is calculated using the equation:

$$\% \text{ Lucifer Yellow} = \frac{V_{Basolateral} \times RFU_{Basolateral}}{V_{Apical} \times RFU_{Apical} + V_{Basolateral} \times RFU_{Basolateral}} \times 100$$

where $RFU_{Apical}$ and $RFU_{Basolateral}$ are the relative fluorescence unit values of lucifer yellow in the apical and basolateral wells, respectively; $V_{Apical}$ and $V_{Basolateral}$ are the volume of apical and basolateral wells (0.075 mL and 0.25 mL), respectively. Percent lucifer yellow should be less than 2. Data is shown in Table 6.

TABLE 6

| Example | EZH2 residence time (hours) | Cellular permeability ($10^{-6}$ cm/s)/ Efflux ratio |
|---|---|---|
| Example 1 | >100 | 5.6/0.79 |

TABLE 6-continued
| Example | EZH2 residence time (hours) | Cellular permeability (10⁻⁶ cm/s)/ Efflux ratio |
|---|---|---|
| (single enantiomer, single geometric isomer) 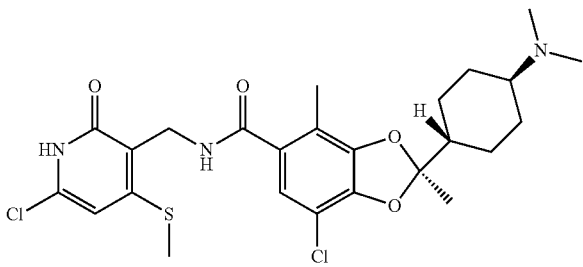 [SMILES: CSc1cc(Cl)[nH]c(=O)c1CNC(=O)c1cc(Cl)c2c(c1C)O[C@@](C)([C@H]1CC[C@H](N(C)C)CC1)O2] Example 3 | | 3.7/1.2 |
| 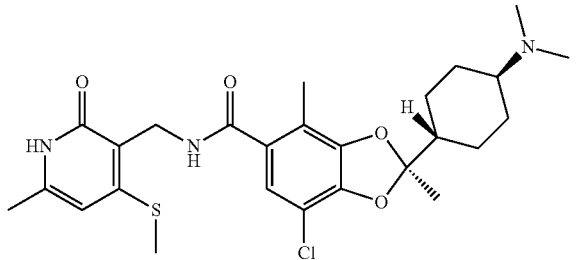 Example 4 (R enantiomer; trans geometric isomer) | | 0.62/2.3 |
| 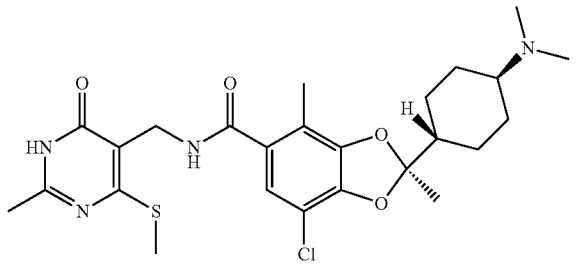 Example 5 (R enantiomer; trans geometric isomer) | | 1.1/3.6 |
| 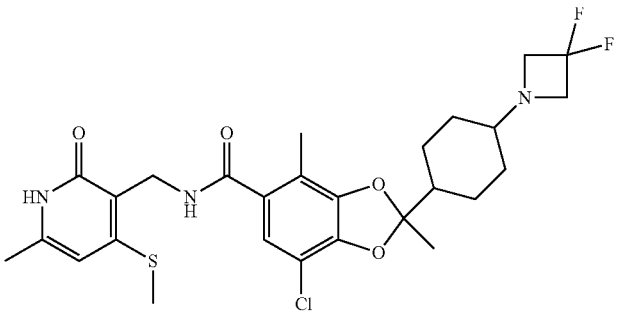 [SMILES: CSc1cc(C)[nH]c(=O)c1CNC(=O)c1cc(Cl)c2c(c1C)OC(C)(C1CCC(N3CC(F)(F)C3)CC1)O2] Example 7-Enantiomer 2 (single enantiomer; single geometric isomer) | 33 | 12/0.71 |

TABLE 6-continued
| Example | EZH2 residence time (hours) | Cellular permeability ($10^{-6}$ cm/s)/ Efflux ratio |
|---|---|---|
| 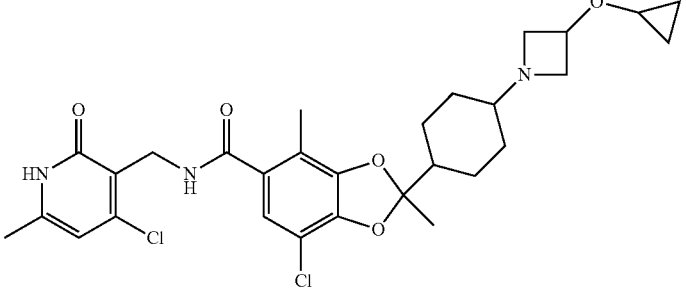<br>Example 8<br>(single enantiomer; single geometric isomer) | >100 | 6.1/0.9 |
| 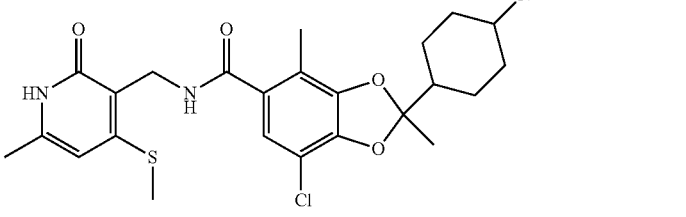<br>Example 9<br>(single enantiomer; single geometric isomer) | >100 | 3.8/1.4 |
| 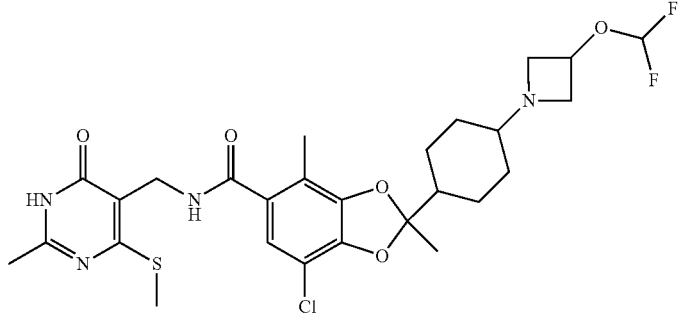 [SMILES: CSc1nc(C)[nH]c(=O)c1CNC(=O)c1cc(Cl)c2c(c1C)OC(C)(C1CCC(N3CC(OC(F)F)C3)CC1)O2]<br>Example 10<br>(single enantiomer; single geometric isomer) | 37 | 6.5/0.69 |
| 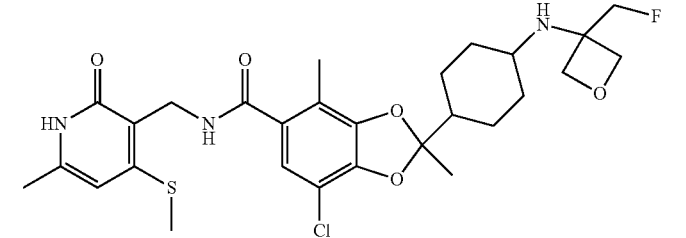 [SMILES: CSc1cc(C)[nH]c(=O)c1CNC(=O)c1cc(Cl)c2c(c1C)OC(C)(C1CCC(NC3(CF)COC3)CC1)O2]<br>Example 11<br>(single enantiomer; geometric isomer 1) | | 5.3/1.3 |

TABLE 6-continued
| Example | EZH2 residence time (hours) | Cellular permeability ($10^{-6}$ cm/s)/ Efflux ratio |
|---|---|---|
| 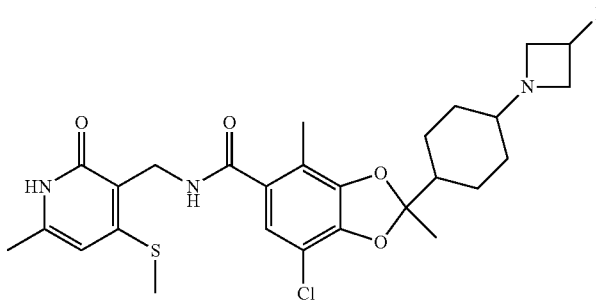<br>Example 12<br>(single enantiomer; single geometric isomer) | >100 | 6.3/1.2 |
| 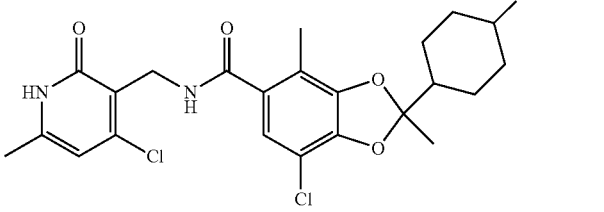<br>Example 13<br>(single enantiomer; single geometric isomer) | 48 | 8.9/0.64 |
| 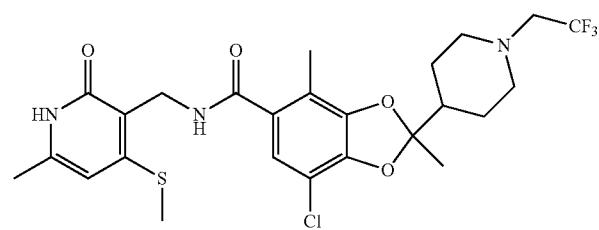 [SMILES: CSc1cc(C)[nH]c(=O)c1CNC(=O)c1cc(Cl)c2c(c1C)OC(C)(C1CCN(CC(F)(F)F)CC1)O2]<br>Example 14-Enantiomer 2<br>(single enantiomer) | | 13/0.56 |
| 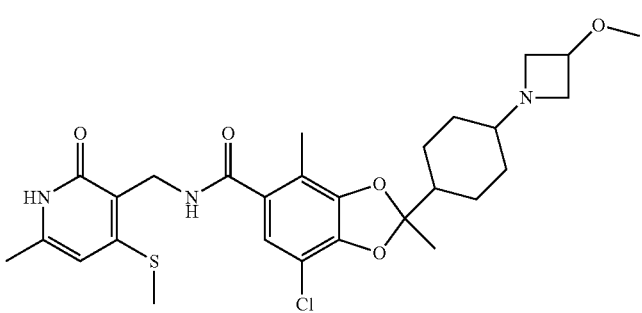<br>Example 17<br>(single enantiomer; single geometric isomer) | >100 | 2.5/1.8 |

The invention claimed is:

1. A method for treating cancer in a subject, comprising administering to the subject an effective amount of a compound of the Formula I:

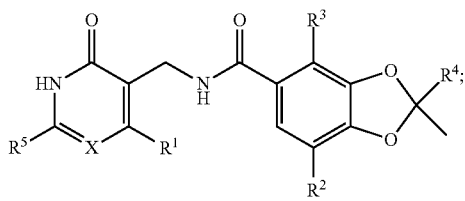

or a pharmaceutically acceptable salt thereof, wherein:

$R_1$ is halo, —S($C_1$-$C_4$)alkyl, —S($C_3$-$C_7$)cycloalkyl, or —S[halo($C_1$-$C_4$)alkyl];

X is CH or N;

$R^2$ is hydrogen, halo, ($C_1$-$C_4$)alkyl, or halo($C_1$-$C_4$)alkyl;

$R^3$ is halo, ($C_1$-$C_4$)alkyl, or halo($C_1$-$C_4$)alkyl;

$R^4$ is ($C_3$-$C_7$)cycloalkyl or 4-7 membered heterocyclyl, each of which are optionally substituted with 1 to 3 groups selected from halo, ($C_1$-$C_4$)alkyl, halo($C_1$-$C_4$)alkyl, ($C_1$-$C_4$)alkoxy, halo($C_1$-$C_4$)alkoxy, and —$NR^aR^b$;

$R^a$ is hydrogen, ($C_1$-$C_4$)alkyl, or halo($C_1$-$C_4$)alkyl;

$R^b$ is ($C_1$-$C_4$)alkyl, halo($C_1$-$C_4$)alkyl, or 4-7 membered heterocyclyl, wherein said heterocyclyl is optionally substituted with 1 to 3 groups selected from halo, ($C_1$-$C_4$)alkyl, halo($C_1$-$c_4$) alkyl, ($C_1$-$C_4$)alkoxy, and halo($C_1$-$C_4$)alkoxy; or $R^a$ and $R^b$ together with the nitrogen atom to which they are attached form a 4-7 membered heterocyclyl optionally substituted with 1 to 3 groups selected from halo, ($C_1$-$C_4$)alkyl, halo($C_1$-$C_4$) alkyl, and —$OR^c$;

$R^c$ is ($C_1$-$C_4$)alkyl, halo($C_1$-$C_4$)alkyl, or ($C_3$-$C_7$)cycloalkyl; and $R^5$ is halo, ($C_1$-$C_4$)alkyl, or halo($C_1$-$C_4$)alkyl.

2. The method of claim 1, wherein:

$R^1$ is halo or —S($C_1$-$C_4$)alkyl;

$R^2$ is halo;

$R^3$ is ($C_1$-$C_4$)alkyl;

$R^4$ is ($C_3$-$C_7$)cycloalkyl or ($C_4$-$C_7$)heterocyclyl, each of which are optionally substituted with 1 to 2 groups selected from halo($C_1$-$C_4$)alkyl and —$NR^aR^b$;

$R^a$ is hydrogen or ($C_1$-$C_4$)alkyl;

$R^b$ is ($C_1$-$C_4$)alkyl or ($C_4$-$C_7$)heterocyclyl, wherein said heterocyclyl is optionally substituted with halo($C_1$-$C_4$)alkyl; or $R^a$ and $R^b$ together with the nitrogen atom to which they are attached form a 4-7 membered nitrogen containing heterocyclyl optionally substituted with 1 to 3 groups selected from halo and —$OR^c$;

$R^c$ is ($C_1$-$C_4$)alkyl, halo($C_1$-$C_4$)alkyl, or ($C_3$-$C_7$)cycloalkyl; and $R^5$ is halo or ($C_1$-$C_4$)alkyl.

3. The method of claim 1, wherein the compound is of the Formula II:

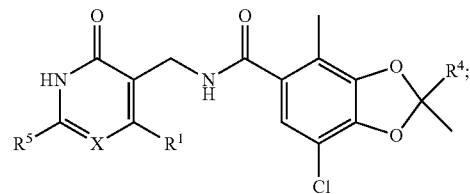

or a pharmaceutically acceptable salt thereof.

4. The method of claim 1, wherein $R^1$ is chloro.

5. The method of claim 1, wherein $R^1$ is —$SCH_3$.

6. The method of claim 1, wherein $R^4$ is cyclohexyl or piperidinyl, each of which are optionally substituted with 1 to 2 groups selected from halo($C_1$-$C_4$)alkyl and —$NR^aR^b$.

7. The method of claim 1, wherein the compound is of the Formula III:

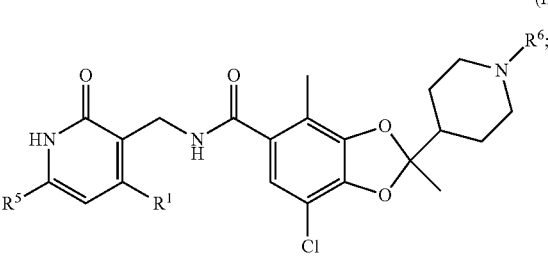

or a pharmaceutically acceptable salt thereof, wherein $R^6$ is halo($C_1$-$C_4$)alkyl.

8. The method of claim 1, wherein the compound is of the Formula IV:

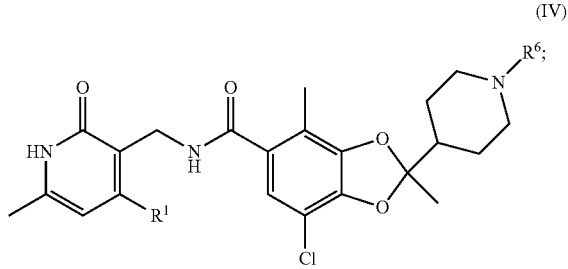

or a pharmaceutically acceptable salt thereof.

9. The method of claim 1, wherein the compound is of the Formula (V):

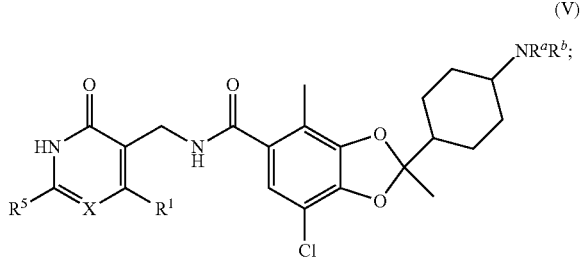

or a pharmaceutically acceptable salt thereof.

10. The method of claim 1, wherein the compound is of the Formula:

(VI)

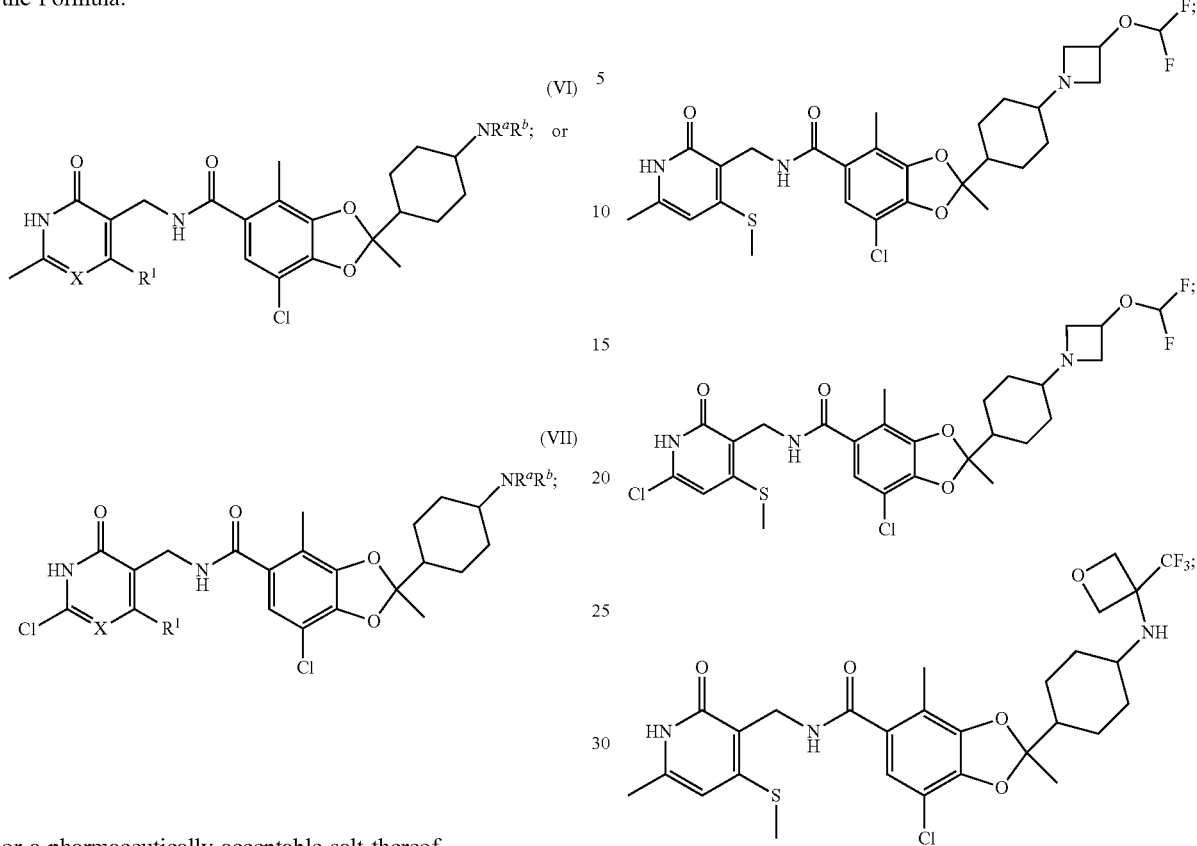

or a pharmaceutically acceptable salt thereof.

11. The method of claim 1, wherein the compound is of the Formula:

(VII)

or a pharmaceutically acceptable salt thereof.

12. The method of claim 1, wherein $R^b$ is $(C_1\text{-}C_4)$alkyl or oxetanyl, wherein said oxetanyl is optionally substituted with halo$(C_1\text{-}C_4)$alkyl; or $R^a$ and $R^b$ together with the nitrogen atom to which they are attached form an azetidinyl optionally substituted with halo or —$OR^c$.

13. The method of claim 1, wherein $R^a$ is hydrogen or methyl; and $R^b$ is methyl or oxatanyl, wherein said oxetanyl is optionally substituted with —$CH_2F$ or —$CF_3$.

14. The method of claim 1, wherein $R^a$ and $R^b$ together with the nitrogen atom to which they are attached form an azetidinyl optionally substituted with 1 to 2 fluoro or —$OR^c$; and $R^c$ is —$CH_3$, —$CHF_2$, or cyclopropyl.

15. The method of claim 1, wherein the compound is of the Formula:

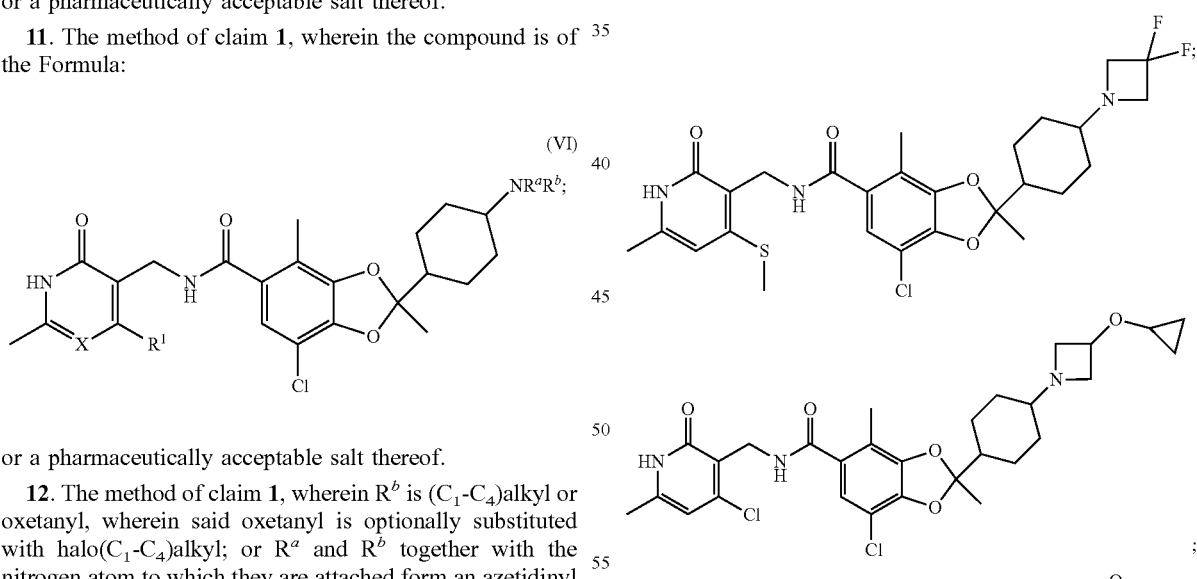

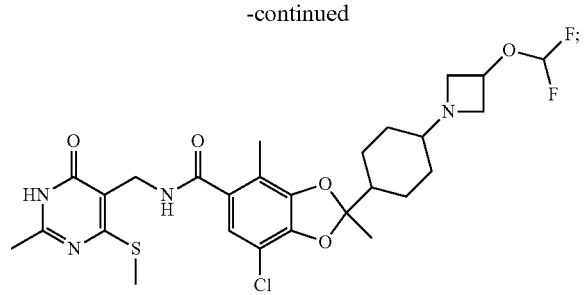
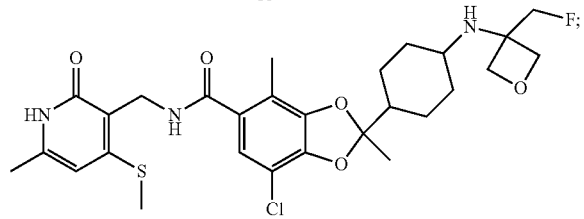
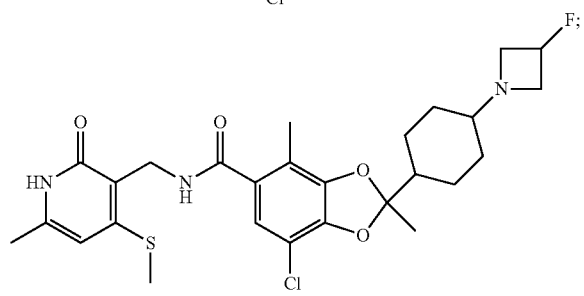
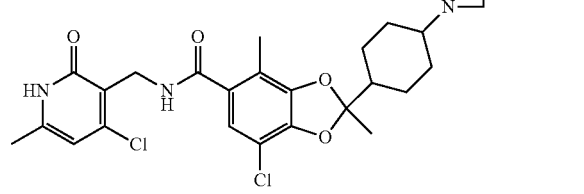
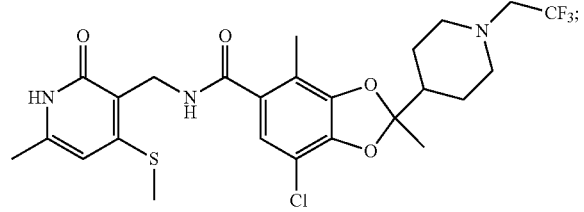
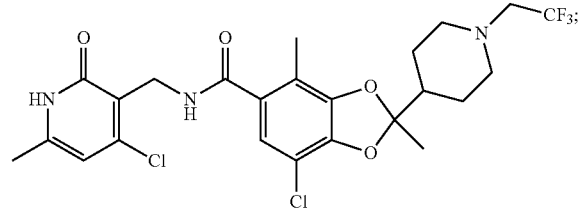
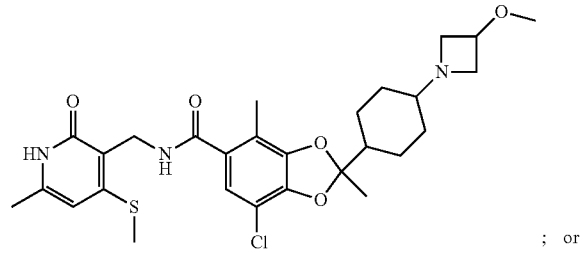

; or

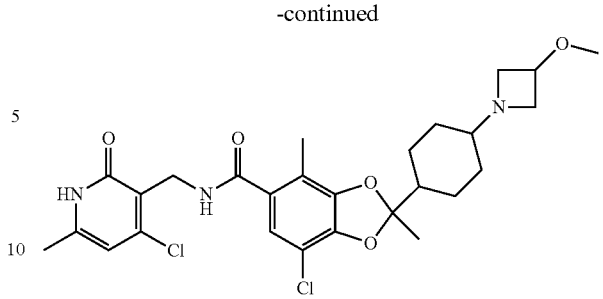

;

or a pharmaceutically acceptable salt thereof.

16. The method of claim 1, wherein the group

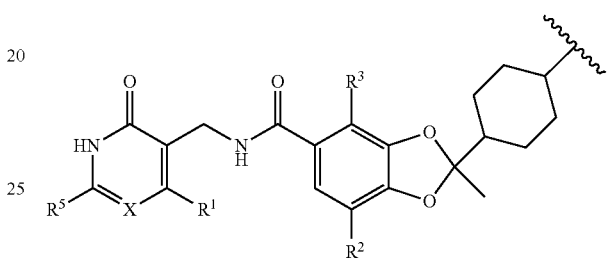

and NR$^a$R$^b$ are oriented trans about the cyclohexyl.

17. The method of claim 1, wherein the group

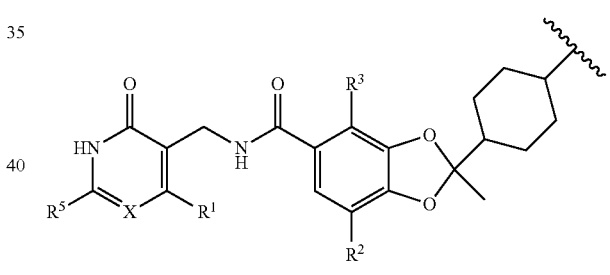

and NR$^a$R$^b$ are oriented cis about the cyclohexyl.

18. The method of claim 1, wherein the stereochemical configuration of the chiral center of the 1,3-dioxolanyl is R.

19. The method of claim 1, wherein the stereochemical configuration of the chiral center of the 1,3-dioxolanyl is S.

20. The method of claim 1, wherein the compound is of the Formula:

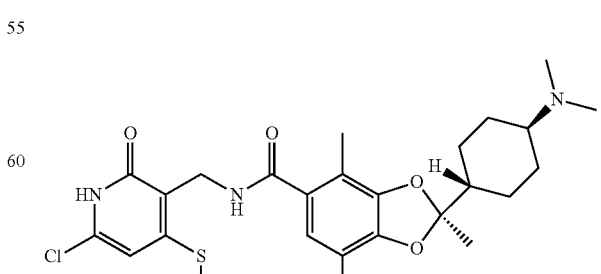

;

-continued

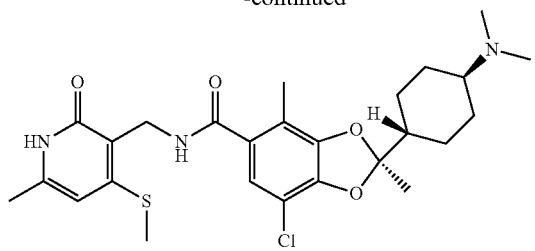

; or

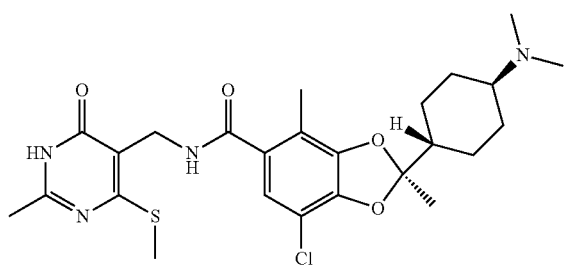

;

or a pharmaceutically acceptable salt thereof.

21. The method of claim 1, wherein the cancer is selected from breast cancer, prostate cancer, colon cancer, kidney cancer, brain cancer, bladder cancer, urethral cancer, skin cancer, gastric cancer, endometrial cancer, pancreatic cancer, bronchial cancer, esophageal cancer, soft tissue sarcoma, bone cancer, lymphoma, leukemia, lung cancer, ovarian cancer, and liver cancer.

22. A method for treating cancer in a subject, comprising administering to the subject an effective amount of a compound having the formula:

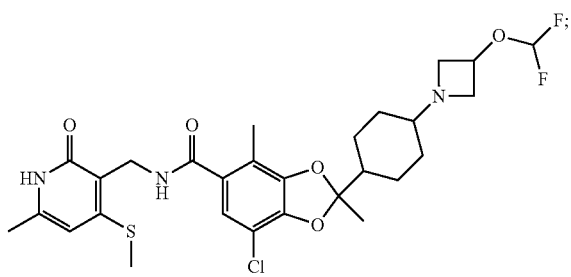 [SMILES: CSc1cc(C)[nH]c(=O)c1CNC(=O)c1cc(Cl)c2c(c1C)OC(C)(C1CCC(N3CC(OC(F)F)C3)CC1)O2]

or a pharmaceutically acceptable salt thereof.

23. The method of claim 22, wherein the cancer is selected from breast cancer, prostate cancer, colon cancer, kidney cancer, brain cancer, bladder cancer, urethral cancer, skin cancer, gastric cancer, endometrial cancer, pancreatic cancer, bronchial cancer, esophageal cancer, soft tissue sarcoma, bone cancer, lymphoma, leukemia, lung cancer, ovarian cancer, and liver cancer.

24. A method for treating cancer in a subject, comprising administering to the subject an effective amount of a compound having the formula:

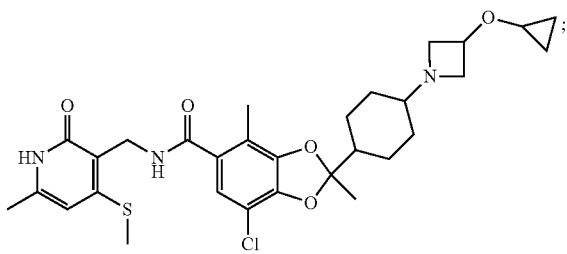 [SMILES: CSc1cc(C)[nH]c(=O)c1CNC(=O)c1cc(Cl)c2c(c1C)OC(C)(C1CCC(N3CC(OC4CC4)C3)CC1)O2]

or a pharmaceutically acceptable salt thereof.

25. The method of claim 24, wherein the cancer is selected from breast cancer, prostate cancer, colon cancer, kidney cancer, brain cancer, bladder cancer, urethral cancer, skin cancer, gastric cancer, endometrial cancer, pancreatic cancer, bronchial cancer, esophageal cancer, soft tissue sarcoma, bone cancer, lymphoma, leukemia, lung cancer, ovarian cancer, and liver cancer.

26. A method for treating cancer in a subject, comprising administering to the subject an effective amount of a compound having the formula:

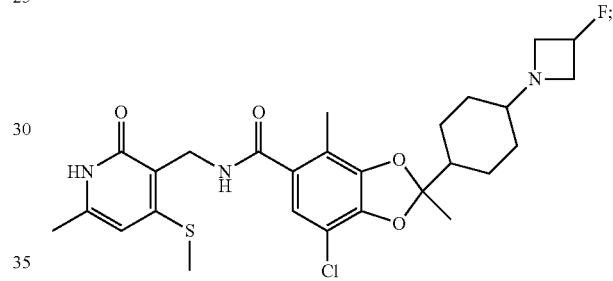

or a pharmaceutically acceptable salt thereof.

27. The method of claim 26, wherein the cancer is selected from breast cancer, prostate cancer, colon cancer, kidney cancer, brain cancer, bladder cancer, urethral cancer, skin cancer, gastric cancer, endometrial cancer, pancreatic cancer, bronchial cancer, esophageal cancer, soft tissue sarcoma, bone cancer, lymphoma, leukemia, lung cancer, ovarian cancer, and liver cancer.

28. A method for treating cancer in a subject, comprising administering to the subject an effective amount of a compound having the formula:

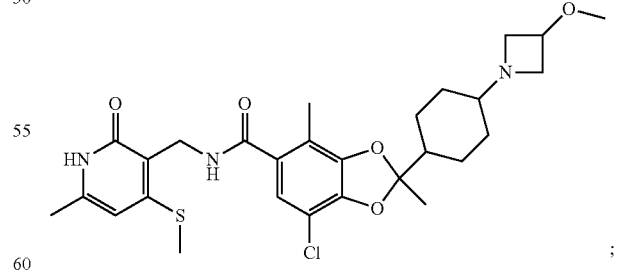

;

or a pharmaceutically acceptable salt thereof.

29. The method of claim 28, wherein the cancer is selected from breast cancer, prostate cancer, colon cancer, kidney cancer, brain cancer, bladder cancer, urethral cancer, skin cancer, gastric cancer, endometrial cancer, pancreatic cancer, bronchial cancer, esophageal cancer, soft tissue sarcoma, bone cancer, lymphoma, leukemia, lung cancer, ovarian cancer, and liver cancer.

30. The method of claim 21, wherein the cancer is selected from Cancer in melanoma, renal cell carcinoma, glioblastoma multiforme, medulloblastoma, Ewing's sarcoma, cholangiocarcinoma, multiple myeloma, mesothelioma, diffuse large B-cell lymphoma, follicular lymphoma, mantle cell lymphoma, marginal zone B-cell lymphoma, Burkitt's lymphoma, T-cell lymphoma, small cell lung cancer, non-small cell lung cancer, and squamous cell carcinoma.

31. The method of claim 23, wherein the cancer is selected from Cancer in melanoma, renal cell carcinoma, glioblastoma multiforme, medulloblastoma, Ewing's sarcoma, cholangiocarcinoma, multiple myeloma, mesothelioma, diffuse large B-cell lymphoma, follicular lymphoma, mantle cell lymphoma, marginal zone B-cell lymphoma, Burkitt's lymphoma, T-cell lymphoma, small cell lung cancer, non-small cell lung cancer, and squamous cell carcinoma.

32. The method of claim 25, wherein the cancer is selected from Cancer in melanoma, renal cell carcinoma, glioblastoma multiforme, medulloblastoma, Ewing's sarcoma, cholangiocarcinoma, multiple myeloma, mesothelioma, diffuse large B-cell lymphoma, follicular lymphoma, mantle cell lymphoma, marginal zone B-cell lymphoma, Burkitt's lymphoma, T-cell lymphoma, small cell lung cancer, non-small cell lung cancer, and squamous cell carcinoma.

33. The method of claim 27, wherein the cancer is selected from Cancer in melanoma, renal cell carcinoma, glioblastoma multiforme, medulloblastoma, Ewing's sarcoma, cholangiocarcinoma, multiple myeloma, mesothelioma, diffuse large B-cell lymphoma, follicular lymphoma, mantle cell lymphoma, marginal zone B-cell lymphoma, Burkitt's lymphoma, T-cell lymphoma, small cell lung cancer, non-small cell lung cancer, and squamous cell carcinoma.

34. The method of claim 29, wherein the cancer is selected from Cancer in melanoma, renal cell carcinoma, glioblastoma multiforme, medulloblastoma, Ewing's sarcoma, cholangiocarcinoma, multiple myeloma, mesothelioma, diffuse large B-cell lymphoma, follicular lymphoma, mantle cell lymphoma, marginal zone B-cell lymphoma, Burkitt's lymphoma, T-cell lymphoma, small cell lung cancer, non-small cell lung cancer, and squamous cell carcinoma.

* * * * *

UNITED STATES PATENT AND TRADEMARK OFFICE
CERTIFICATE OF CORRECTION

PATENT NO. : 11,274,095 B2
APPLICATION NO. : 16/856454
DATED : March 15, 2022
INVENTOR(S) : Alexandre Côté et al.

Page 1 of 1

It is certified that error appears in the above-identified patent and that said Letters Patent is hereby corrected as shown below:

In the Claims

Column 77, Claim 1, Line 19, please replace "$R_1$ is halo, -S($C_1$-$C_4$)alkyl," with --$R^1$ is halo, -S($C_1$-$C_4$)alkyl,--;
Line 30, please replace "$R^1$ is hydrogen," with --$R^a$ is hydrogen,--;
Line 35, please replace "($C_1$-$C_4$)alkyl, halo($C_1$-$c_4$) alkyl, ($C_1$-$C_4$)alkoxy, and" with --($C_1$-$C_4$)alkyl, halo($C_1$-$C_4$) alkyl, ($C_1$-$C_4$)alkoxy, and--.

Signed and Sealed this
Third Day of January, 2023

Katherine Kelly Vidal
*Director of the United States Patent and Trademark Office*